United States Patent
Gjerde et al.

(10) Patent No.: US 8,148,168 B2
(45) Date of Patent: *Apr. 3, 2012

(54) METHOD AND DEVICE FOR SAMPLE PREPARATION

(75) Inventors: Douglas T. Gjerde, Saratoga, CA (US); Allen Burge, Sunnyvale, CA (US); Ronald Jones, Morgan Hill, CA (US); Mark Abel, San Jose, CA (US)

(73) Assignee: PhyNexus, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/837,141

(22) Filed: Jul. 15, 2010

(65) Prior Publication Data

US 2011/0038769 A1    Feb. 17, 2011

Related U.S. Application Data

(63) Continuation of application No. 12/730,160, filed on Mar. 23, 2010, now Pat. No. 7,875,462, which is a continuation of application No. 11/285,531, filed on Nov. 21, 2005, now Pat. No. 7,722,820, which is a continuation-in-part of application No. 10/754,352, filed on Jan. 8, 2004, now abandoned, which is a continuation-in-part of application No. 10/620,155, filed on Jul. 14, 2003, now Pat. No. 7,482,169.

(51) Int. Cl.
    *G01N 1/18* (2006.01)
(52) U.S. Cl. ........ 436/178; 422/513; 422/535; 422/534; 422/527; 422/524; 436/177
(58) Field of Classification Search ................. 436/177, 436/178; 422/100, 101, 501, 513, 527, 535, 422/534, 524; 210/636, 638, 656
See application file for complete search history.

(56) References Cited

U.S. PATENT DOCUMENTS

| | | | | |
|---|---|---|---|---|
| 5,437,979 A * | 8/1995 | Rampal et al. | ............... | 435/6.16 |
| 5,512,168 A * | 4/1996 | Fetner et al. | ............... | 210/198.2 |
| 5,556,598 A * | 9/1996 | Raybuck et al. | ............... | 422/525 |
| 5,595,653 A * | 1/1997 | Good et al. | ............... | 210/289 |
| 5,833,927 A * | 11/1998 | Raybuck et al. | ............... | 422/513 |
| 6,045,757 A * | 4/2000 | Moriarty et al. | ............... | 422/513 |
| 6,048,457 A * | 4/2000 | Kopaciewicz et al. | ..... | 210/321.6 |
| 6,117,394 A * | 9/2000 | Smith | ............... | 422/513 |
| 6,200,474 B1 * | 3/2001 | Kopaciewicz et al. | ..... | 210/321.6 |
| 6,416,716 B1 * | 7/2002 | Shukla et al. | ............... | 422/527 |
| 6,482,362 B1 * | 11/2002 | Smith | ............... | 422/513 |
| 6,566,145 B2 * | 5/2003 | Brewer | ............... | 436/178 |
| 6,770,246 B1 * | 8/2004 | Husek | ............... | 422/69 |
| 7,482,169 B2 * | 1/2009 | Gjerde et al. | ............... | 436/178 |
| 7,722,820 B2 * | 5/2010 | Gjerde et al. | ............... | 422/101 |
| 2002/0110495 A1 * | 8/2002 | Hunt et al. | ............... | 422/101 |
| 2003/0007897 A1 * | 1/2003 | Creasey | ............... | 422/100 |
| 2003/0178370 A1 * | 9/2003 | Fisk et al. | ............... | 210/656 |
| 2004/0072375 A1 * | 4/2004 | Gjerde et al. | ............... | 436/541 |

* cited by examiner

*Primary Examiner* — Robert J Hill, Jr.
*Assistant Examiner* — Dwan A Gerido
(74) *Attorney, Agent, or Firm* — Sue S. Kalman

(57) ABSTRACT

The invention provides extraction columns for the purification of an analyte (e.g., a biological macromolecule, such as a peptide, protein or nucleic acid) from a sample solution, as well as methods for making and using such columns. The columns typically include a bed of extraction media positioned in the column, often between two frits. In some embodiments, the extraction columns employ modified pipette tips as column bodies. In some embodiments, the extraction columns are comprised of frits having a low pore. In some embodiments, the frits of the extraction columns have a pore volume of less than one microliter or less than 10% of the interstitial volume of the bed of extraction media.

22 Claims, 20 Drawing Sheets

METHOD AND DEVICE FOR SAMPLE PREPARATION

CROSS REFERENCE TO RELATED APPLICATIONS

The present application is a continuation of U.S. patent application Ser. No. 12/730,160, filed Mar. 23, 2010, now U.S. Pat. No. 7,875,462, which is a continuation of U.S. patent application Ser. No. 11/285,531, filed Nov. 21, 2005, now U.S. Pat. No. 7,722,820 which is a Continuation-in-Part of U.S. patent application Ser. No. 10/754,352 filed Jan. 8, 2004, now abandoned, which is a Continuation-in-Part of U.S. patent application Ser. No. 10/620,155 filed Jul. 14, 2003, now U.S. Pat. No. 7,482,169, the disclosures of which are incorporated herein by reference in their entirety for all purposes.

FIELD OF THE INVENTION

This invention relates to methods and devices for sample preparation, such as separating (i.e., extracting or purifying) an analyte from a sample solution. The analytes can include biomolecules, particularly biological macromolecules such as proteins and peptides. The device and method of this invention are particularly useful in proteomics for sample preparation and analysis with analytical technologies employing biochips, mass spectrometry and other instrumentation.

BACKGROUND OF THE INVENTION

Solid phase extraction is a powerful technology for purifying and concentrating analytes, including biomolecules. For example, it is one of the primary tools used for preparing protein samples prior to analysis by any of a variety of analytical techniques, including mass spectrometry, surface plasmon resonance, nuclear magnetic resonance, x-ray crystallography, and the like. With these techniques, typically only a small volume of sample is required. However, it is often critical that interfering contaminants be removed from the sample and that the analyte of interest is present at some minimum concentration. Thus, sample preparation methods are needed the permit the purification and concentration of small volume samples with minimal sample loss.

The subject invention involves methods and devices for extracting an analyte from a sample solution using a packed bed of extraction media, e.g., a bed of gel-type beads derivatized with a group having an affinity for an analyte of interest. These methods, and the related devices and reagents, will be of particular interest to the life scientist, since they provide a powerful technology for purifying, concentrating and analyzing biomolecules and other analytes of interest. However, the methods, devices and reagents are not limited to use in the biological sciences, and can find wide application in a variety of preparative and analytical contexts.

DESCRIPTION OF SPECIFIC EMBODIMENTS OF THE INVENTION

Figure 1:
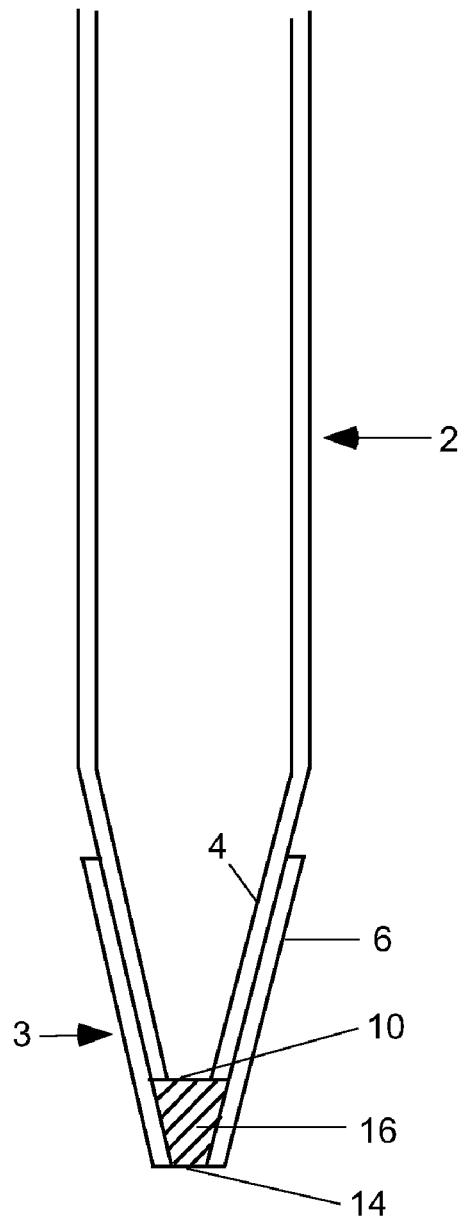
FIG. 1 depicts an embodiment of the invention where the extraction column body is constructed from a tapered pipette tip.

This invention relates to methods and devices for extracting an analyte from a sample solution. The analytes can include biomolecules, particularly biological macromolecules such as proteins and peptides, polynucleotides, lipids and polysaccharides. The device and method of this invention are particularly useful in proteomics for sample preparation and analysis with analytical technologies employing biochips, mass spectrometry and other instrumentation. The extraction process generally results in the enrichment, concentration, and/or purification of an analyte or analytes of interest.

In U.S. patent application Ser. No. 10/620,155, incorporated by reference herein in its entirety, methods and devices for performing low dead column extractions are described. The instant specification, inter alia, expands upon the concepts described in that application.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.
Definitions In describing and claiming the present invention, the following terminology will be used in accordance with the definitions set out below.

The term "bed volume" as used herein is defined as the volume of a bed of extraction media in an extraction column. Depending on how densely the bed is packed, the volume of the extraction media in the column bed is typically about one third to two thirds of the total bed volume; well packed beds have less space between the beads and hence generally have lower interstital volumes.

The term "interstitial volume" of the bed refers to the volume of the bed of extraction media that is accessible to solvent, e.g., aqueous sample solutions, wash solutions and desorption solvents. For example, in the case where the extraction media is a chromatography bead (e.g., agarose or sepharose), the interstitial volume of the bed constitutes the solvent accessible volume between the beads, as well as any solvent accessible internal regions of the bead, e.g., solvent accessible pores. The interstitial volume of the bed represents the minimum volume of liquid required to saturate the column bed.

The term "dead volume" as used herein with respect to a column is defined as the interstitial volume of the extraction bed, tubes, membrane or frits, and passageways in a column. Some preferred embodiments of the invention involve the use of low dead volume columns, as described in more detail in U.S. patent application Ser. No. 10/620,155.

The term "elution volume" as used herein is defined as the volume of desorption or elution liquid into which the analytes are desorbed and collected. The terms "desorption solvent," "elution liquid" and the like are used interchangeably herein.

The term "enrichment factor" as used herein is defined as the ratio of the sample volume divided by the elution volume, assuming that there is no contribution of liquid coming from the dead volume. To the extent that the dead volume either dilutes the analytes or prevents complete adsorption, the enrichment factor is reduced.

The terms "extraction column" and "extraction tip" as used herein are defined as a column device used in combination with a pump, the column device containing a bed of solid phase extraction material, i.e., extraction media.

The term "frit" as used herein are defined as porous material for holding the extraction media in place in a column. An extraction media chamber is typically defined by a top and bottom frit positioned in an extraction column. In preferred embodiments of the invention the frit is a thin, low pore volume filter, e.g., a membrane screen.

The term "lower column body" as used herein is defined as the column bed and bottom membrane screen of a column.

The term "membrane screen" as used herein is defined as a woven or non-woven fabric or screen for holding the column packing in place in the column bed, the membranes having a low dead volume. The membranes are of sufficient strength to withstand packing and use of the column bed and of sufficient porosity to allow passage of liquids through the column bed. The membrane is thin enough so that it can be sealed around the perimeter or circumference of the membrane screen so that the liquids flow through the screen.

The term "sample volume", as used herein is defined as the volume of the liquid of the original sample solution from which the analytes are separated or purified.

The term "upper column body", as used herein is defined as the chamber and top membrane screen of a column.

The term "biomolecule" as used herein refers to biomolecule derived from a biological system. The term includes biological macromolecules, such as a proteins, peptides, and nucleic acids.

The term "protein chip" is defined as a small plate or surface upon which an array of separated, discrete protein samples are to be deposited or have been deposited. These protein samples are typically small and are sometimes referred to as "dots." In general, a chip bearing an array of discrete proteins is designed to be contacted with a sample having one or more biomolecules which may or may not have the capability of binding to the surface of one or more of the dots, and the occurrence or absence of such binding on each dot is subsequently determined. A reference that describes the general types and functions of protein chips is Gavin MacBeath, *Nature Genetics Supplement,* 32:526 (2002).

Extraction Columns

In accordance with the present invention there may be employed conventional chemistry, biological and analytical techniques within the skill of the art. Such techniques are explained fully in the literature. See, e.g. *Chromatography,* $5^{th}$ edition, PART A: FUNDAMENTALS AND TECHNIQUES, editor: E. Heftmann, Elsevier Science Publishing Company, New York (1992); ADVANCED CHROMATOGRAPHIC AND ELECTROMIGRATION METHODS IN BIOSCIENCES, editor: Z. Deyl, Elsevier Science BV, Amsterdam, The Netherlands, (1998); CHROMATOGRAPHY TODAY, Colin F. Poole and Salwa K. Poole, and Elsevier Science Publishing Company, New York, (1991).

In some embodiments of the subject invention the packed bed of extraction media is contained in a column, e.g., a low dead volume column. Non-limiting examples of suitable columns, particularly low dead volume columns, are presented herein. It is to be understood that the subject invention is not to be construed as limited to the use of extraction beds in low dead volume columns, or in columns in general. For example, the invention is equally applicable to use with a packed bed of extraction media as a component of a multi-well plate.

Column Body

The column body is a tube having two open ends connected by an open channel, sometimes referred to as a through passageway. The tube can be in any shape, including but not limited to cylindrical or frustoconical, and of any dimensions consistent with the function of the column as described herein. In some preferred embodiments of the invention the column body takes the form of a pipette tip, a syringe, a luer adapter or similar tubular bodies. In embodiments where the column body is a pipette tip, the end of the tip wherein the bed of extraction media is placed can take any of a number of geometries, e.g., it can be tapered or cylindrical. In some case a cylindrical channel of relatively constant radius can be preferable to a tapered tip, for a variety of reason, e.g., solution flows through the bed at a uniform rate, rather than varying as a function of a variable channel diameter.

In some embodiments, one of the open ends of the column, sometimes referred to herein as the open upper end of the column, is adapted for attachment to a pump, either directly or indirectly. In some embodiments of the invention the upper open end is operatively attached to a pump, whereby the pump can be used for aspirating (i.e., drawing) a fluid into the extraction column through the open lower end of the column, and optionally for discharging (i.e., expelling) fluid out through the open lower end of the column. Thus, it is a feature certain embodiments of the present invention that fluid enters and exits the extraction column through the same open end of the column, typically the open lower end. This is in contradistinction with the operation of some extraction columns, where fluid enters the column through one open end and exits through the other end after traveling through an extraction media, i.e., similar to conventional column chromatography. The fluid can be a liquid, such as a sample solution, wash solution or desorption solvent.

In other embodiments of the present invention, fluid enters the column through one end and exits through the other. In some embodiments, the invention provides extraction methods that involve a hybrid approach; that is, one or more fluids enter the column through one end and exit through the other, and one more fluids enter and exit the column through the same open end of the column, e.g., the lower end. Thus, for example, in some methods the sample solution and/or wash solution are introduced through the top of the column and exit through the bottom end, while the desorption solution enters and exits through the bottom opening of the column. Aspiration and discharge of solution through the same end of the column can be particularly advantageous in procedures designed to minimize sample loss, particularly when small volumes of liquid are used. A good example would be a procedure that employs a very small volume of desorption solvent, e.g., a procedure involving a high enrichment factor.

The column body can be can be composed of any material that is sufficiently non-porous that it can retain fluid and that is compatible with the solutions, media, pumps and analytes used. A material should be employed that does not substantially react with substances it will contact during use of the extraction column, e.g., the sample solutions, the analyte of interest, the extraction media and desorption solvent. A wide range of suitable materials are available and known to one of skill in the art, and the choice is one of design. Various plastics make ideal column body materials, but other materials such as glass, ceramics or metals could be used in some embodiments of the invention. Some examples of preferred materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials. Some specific examples of suitable column bodies are provided in the Examples.

Extraction Media

The extraction media used in the column is preferably a form of water-insoluble particle (e.g., a porous or non-porous bead) that has an affinity for an analyte of interest. Typically the analyte of interest is a protein, peptide or nucleic acid. The extraction processes can be affinity, size exclusion, reverse phase, normal phase, ion exchange, hydrophobic interaction chromatography, or hydrophilic interaction chromatography agents. In general, the term "extraction media" is used in a broad sense to encompass any media capable of effecting separation, either partial or complete, of an analyte from another. Thus, the terms "separation column" and "extraction column" can be used interchangeably. The term "analyte" can refer to any compound of interest, e.g., to be analyzed or simply removed from a solution.

The bed volume of the extraction media used in the extraction columns of the invention is typically small, typically in the range of 0.1-1000 µL, preferably in the range of 0.1-100 µL, e.g., in a range having a lower limit of 0.1, 0.5, 1, 1.5, 2, 2.5, 3, 5 or 10 µL; and an upper limit of 5, 10, 15, 20, 30, 40 50, 60, 70, 80, 90, 100, 150, 200, 300, 400 or 500 µL. The low bed volume contributes to a low interstitial volume of the bed, reducing the dead volume of the column, thereby facilitating the recovery of analyte in a small volume of desorption solvent.

The low bed volumes employed in certain embodiments allow for the use of relatively small amounts of extraction media, e.g., soft, gel-type beads. For example, some embodiments of the invention employ a bed of extraction media having a dry weight of less than 1 gram (e.g., in the range of 0.001-1 g, 0.005-1 g, 0.01-1 g or 0.02-1 g), less than 100 mg (e.g., in the range of 0.1-100 mg, 0.5-100 mg, 1-100 mg 2-100 mg, or 10-100 mg), less than 10 mg (e.g., in the range of 0.1-10 mg, 0.5-10 mg, 1-10 mg or 2-10 mg), less than 2 mg (e.g., in the range of 0.1-2 mg, 0.5-2 mg or 1-2 mg), or less than 1 mg (e.g., in the range of 0.1-1 mg or 0.5-1 mg).

Many of the extraction media types suitable for use in the invention are selected from a variety of classes of chromatography media. It has been found that many of these chromatography media types and the associated chemistries are suited for use as solid phase extraction media in the devices and methods of this invention.

Thus, examples of suitable extraction media include resin beads used for extraction and/or chromatography. Preferred resins include gel resins, pellicular resins, and macroporous resins.

The term "gel resin" refers to a resin comprising low-crosslinked bead materials that can swell in a solvent, e.g., upon hydration. Crosslinking refers to the physical linking of the polymer chains that form the beads. The physical linking is normally accomplished through a crosslinking monomer that contains bi-polymerizing functionality so that during the polymerization process, the molecule can be incorporated into two different polymer chains. The degree of crosslinking for a particular material can range from 0.1 to 30%, with 0.5 to 10% normally used. 1 to 5% crosslinking is most common. A lower degree of crosslinking renders the bead more permeable to solvent, thus making the functional sites within the bead more accessible to analyte. However, a low crosslinked bead can be deformed easily, and should only be used if the flow of eluent through the bed is slow enough or gentle enough to prevent closing the interstitial spaces between the beads, which could then lead to catastrophic collapse of the bed. Higher crosslinked materials swell less and may prevent access of the analytes and desorption materials to the interior functional groups within the bead. Generally, it is desirable to use as low a level of crosslinking as possible, so long is it is sufficient to withstand collapse of the bed. This means that in conventional gel-packed columns, slow flow rates may have to be used. In the present invention the back pressure is very low, and high liquid flow rates can be used without collapsing the bed. Surprisingly, using these high solvent velocities does not appear to reduce the capacity or usefulness of the bead materials. Common gel resins include agarose, sepharose, polystyrene, polyacrylate, cellulose and other substrates. Gel resins can be non-porous or micro-porous beads.

The low back pressure associated with certain columns of the invention results in some cases in the columns exhibiting characteristics not normally associated with conventional packed columns. For example, in some cases it has been observed that below a certain threshold pressure solvent does not flow through the column. This threshold pressure can be thought of as a "bubble point." In conventional columns, the flow rate through the column generally increases from zero as a smooth function of the pressure at which the solvent is being pushed through the column. With many of the columns of the invention, a progressively increasing pressure will not result in any flow through the column until the threshold pressure is achieved. Once the threshold pressure is reached, the flow will start at a rate significantly greater than zero, i.e., there is no smooth increase in flow rate with pressure, but instead a sudden jump from zero to a relatively fast flow rate. Once the threshold pressure has been exceeded flow commences, the flow rate typically increases relatively smoothly with increasing pressure, as would be the case with conventional columns.

The term "pellicular resins" refers to materials in which the functional groups are on the surface of the bead or in a thin layer on the surface of the bead. The interior of the bead is solid, usually highly crosslinked, and usually inaccessible to the solvent and analytes. Pellicular resins generally have lower capacities than gel and macroporous resins.

The term "macroporous resin" refers to highly crosslinked resins having high surface area due to a physical porous structure that formed during the polymerization process. Generally an inert material (such as a solid or a liquid that does not solvate the polymer that is formed) is polymerized with the bead and then later washed out, leaving a porous structure. Crosslinking of macroporous materials range from 5% to 90% with perhaps a 25 to 55% crosslinking the most common materials. Macroporous resins behave similar to pellicular resins except that in effect much more surface area is available for interaction of analyte with resin functional groups.

Examples of resins beads include polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection. Silica beads are also suitable.

Soft gel resin beads, such as agarose and sepharose based beads, are found to work surprisingly well in columns and methods of this invention. In conventional chromatography fast flow rates can result in bead compression, which results in increased back pressure and adversely impacts the ability to use these gels with faster flow rates. In the present invention relatively small bed volumes are used, and it appears that this allows for the use of high flow rates with a minimal amount of bead compression and the problem attendant with such compression.

The average particle diameters of beads of the invention are typically in the range of about 1 µm to several millimeters, e.g., diameters in ranges having lower limits of 1 µm, 5 µm, 10 µm, 20 µm, 30 µm, 40 µm, 50 µm, 60 µm, 70 µm, 80 µm, 90 µm, 100 µm, 150 µm, 200 µm, 300 µm, or 500 µm, and upper limits of 10 µm, 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

The bead size that may be used depends somewhat on the bed volume and the cross sectional area of the column. A lower bed volume column will tolerate a smaller bead size without generating the high backpressures that could burst a thin membrane frit. For example a bed volume of 0.1 to 1 µL bed, can tolerate 5 to 10 µm particles. Larger beds (up to about 50 µL) normally have beads sizes of 30-150 µm or higher. The upper range of particle size is dependant on the diameter of the column bed. The bead diameter size should not be more than 50% of the bed diameter, and preferably less than 10% of the bed diameter.

The extraction chemistry employed in the present invention can take any of a wide variety of forms. For example, the extraction media can be selected from, or based on, any of the extraction chemistries used in solid-phase extraction and/or chromatography, e.g., reverse-phase, normal phase, hydrophobic interaction, hydrophilic interaction, ion-exchange, thiophilic separation, hydrophobic charge induction or affinity binding. Because the invention is particularly suited to the purification and/or concentration of biomolecules, extraction surfaces capable of adsorbing such molecules are particularly relevant. See, e.g., SEPARATION AND SCIENCE TECHNOLOGY Vol. 2.: HANDBOOK OF BIOSEPARATIONS, edited by Satinder Ahuja, Academic Press (2000).

Affinity extractions use a technique in which a bio-specific adsorbent is prepared by coupling a specific ligand (such as an enzyme, antigen, or hormone) for the analyte, (e.g., macromolecule) of interest to a solid support. This immobilized ligand will interact selectively with molecules that can bind to it. Molecules that will not bind elute un-retained. The interaction is selective and reversible. The references listed below show examples of the types of affinity groups that can be employed in the practice of this invention are hereby incorporated by reference herein in their entireties. Antibody Purification Handbook, *Amersham Biosciences*, Edition AB, 18-1037-46 (2002); Protein Purification Handbook, *Amersham Biosciences*, Edition AC, 18-1132-29 (2001); Affinity Chromatography Principles and Methods, *Amersham Pharmacia Biotech*, Edition AC, 18-1022-29 (2001); The Recombinant Protein Handbook, *Amersham Pharmacia Biotech*, Edition AB, 18-1142-75 (2002); and *Protein Purification: Principles, High Resolution Methods, and Applications*, Jan-Christen Janson (Editor), Lars G. Ryden (Editor), Wiley, John & Sons, *Incorporated* (1989).

Examples of suitable affinity binding agents are summarized in Table I, wherein the affinity agents are from one or more of the following interaction categories:
1. Chelating metal—ligand interaction
2. Protein—Protein interaction
3. Organic molecule or moiety—Protein interaction
4. Sugar—Protein interaction
5. Nucleic acid—Protein interaction
6. Nucleic acid—nucleic acid interaction

TABLE I

| Examples of Affinity molecule or moiety fixed at surface | Captured biomolecule | Interaction Category |
|---|---|---|
| Ni-NTA | His-tagged protein | 1 |
| Ni-NTA | His-tagged protein within a multi-protein complex | 1, 2 |
| Fe-IDA | Phosphopeptides, phosphoproteins | 1 |
| Fe-IDA | Phosphopeptides or phosphoproteins within a multi-protein complex | 1, 2 |
| Antibody or other Proteins | Protein antigen | 2 |
| Antibody or other Proteins | Small molecule-tagged protein | 3 |
| Antibody or other Proteins | Small molecule-tagged protein within a multi-protein complex | 2, 3 |
| Antibody or other Proteins | Protein antigen within a multi-protein complex | 2 |
| Antibody or other Proteins | Epitope-tagged protein | 2 |
| Antibody or other Proteins | Epitope-tagged protein within a multi-protein complex | 2 |
| Protein A, Protein G or Protein L | Antibody | 2 |
| Protein A, Protein G or Protein L | Antibody | 2 |
| ATP or ATP analogs; 5'-AMP | Kinases, phosphatases (proteins that requires ATP for proper function) | 3 |

TABLE I-continued

| Examples of Affinity molecule or moiety fixed at surface | Captured biomolecule | Interaction Category |
|---|---|---|
| ATP or ATP analogs; 5'-AMP | Kinase, phosphatases within multi-protein complexes | 2, 3 |
| Cibacron 3G | Albumin | 3 |
| Heparin | DNA-binding protein | 4 |
| Heparin | DNA-binding proteins within a multi-protein complex | 2, 4 |
| Lectin | Glycopeptide or glycoprotein | 4 |
| Lectin | Glycopeptide or glycoprotein within a multi-protein complex | 2, 4 |
| ssDNA or dsDNA | DNA-binding protein | 5 |
| ssDNA or dsDNA | DNA-binding protein within a multi-protein complex | 2, 5 |
| ssDNA | Complementary ssDNA | 6 |
| ssDNA | Complementary RNA | 6 |
| Streptavidin/Avidin | Biotinylated peptides (ICAT) | 3 |
| Streptavidin/Avidin | Biotinylated engineered tag fused to a protein (see avidity.com) | 3 |
| Streptavidin/Avidin | Biotinylated protein | 3 |
| Streptavidin/Avidin | Biotinylated protein within a multi-protein complex | 2, 3 |
| Streptavidin/Avidin | Biotinylated engineered tag fused to a protein within a multi-protein complex | 2, 3 |
| Streptavidin/Avidin | Biotinylated nucleic acid | 3 |
| Streptavidin/Avidin | Biotinylated nucleic acid bound to a protein or multi-protein complex | 2, 3 |
| Streptavidin/Avidin | Biotinylated nucleic acid bound to a complementary nucleic acid | 3, 6 |

In one aspect of the invention an extraction media is used that contains a surface functionality that has an affinity for a protein fusion tag used for the purification of recombinant proteins. A wide variety of fusion tags and corresponding affinity groups are available and can be used in the practice of the invention.

U.S. patent application Ser. No. 10/620,155 describes in detail the use of specific affinity binding reagents in solid-phase extraction. Examples of specific affinity binding agents include proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA); glutathione surfaces-nucleotides, oligonucleotides, polynucleotides and their analogs (e.g., ATP); lectin surface-heparin surface-avidin or streptavidin surface, a peptide or peptide analog (e.g., that binds to a protease or other enzyme that acts upon polypeptides).

In some embodiments of the invention, the affinity binding reagent is one that recognizes one or more of the many affinity groups used as affinity tags in recombinant fusion proteins. Examples of such tags include poly-histidine tags (e.g., the 6x-His tag), which can be extracted using a chelated metal such as Ni-NTA-peptide sequences (such as the FLAG epitope) that are recognized by an immobilized antibody; biotin, which can be extracted using immobilized avidin or streptavidin; "calmodulin binding peptide" (or, CBP), recognized by calmodulin charged with calcium-glutathione S-transferase protein (GST), recognized by immobilized glutathione; maltose binding protein (MBP), recognized by amylose; the cellulose-binding domain tag, recognized by immobilized cellulose; a peptide with specific affinity for S-protein (derived from ribonuclease A); and the peptide sequence tag CCxxCC (where xx is any amino acid, such as RE), which binds to the affinity binding agent bis-arsenical fluorescein (FlAsH dye).

Antibodies can be extracted using, for example, proteins such as protein A, protein G, protein L, hybrids of these, or by other antibodies (e.g., an anti-IgE for purifying IgE).

Chelated metals are not only useful for purifying poly-his tagged proteins, but also other non-tagged proteins that have an intrinsic affinity for the chelated metal, e.g., phosphopeptides and phosphoproteins.

Antibodies can also be useful for purifying non-tagged proteins to which they have an affinity, e.g., by using antibodies with affinity for a specific phosphorylation site or phosphorylated amino acids.

In other embodiments of the invention extraction surfaces are employed that are generally less specific than the affinity binding agents discussed above. These extraction chemistries are still often quite useful. Examples include ion exchange, reversed phase, normal phase, hydrophobic interaction and hydrophilic interaction extraction or chromatography surfaces. In general, these extraction chemistries, methods of their use, appropriate solvents, etc. are well known in the art, and in particular are described in more detail in U.S. patent application Ser. Nos. 10/434,713 and 10/620,155, and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 3 94 (1991); and ORGANIC SYNTHESIS ON SOLID PHASE, F. Dorwald Wiley VCH Verlag Gmbh, Weinheim 2002.

Frits

In some embodiments of the invention one or more frits is used to contain the bed of extraction in, for example, a column. Frits can take a variety of forms, and can be constructed from a variety of materials, e.g., glass, ceramic, metal, fiber. Some embodiments of the invention employ frits having a low pore volume, which contribute to reducing dead volume. The frits of the invention are porous, since it is necessary for fluid to be able to pass through the frit. The frit should have sufficient structural strength so that frit integrity can contain the extraction media in the column. It is desirable that the frit have little or no affinity for chemicals with which it will come into contact during the extraction process, particularly the analyte of interest. In many embodiments of the invention the analyte of interest is a biomolecule, particularly a biological macromolecule. Thus in many embodiments of the invention it desirable to use a frit that has a minimal tendency to bind or otherwise interact with biological macromolecules, particularly proteins, peptides and nucleic acids.

Frits of various pores sizes and pore densities may be used provided the free flow of liquid is possible and the beads are held in place within the extraction media bed.

In one embodiment, one frit (e.g., a lower, or bottom, frit) is bonded to and extends across the open channel of the column body. Preferably, the bottom frit is attached at or near the open lower end of the column, e.g., bonded to and extend across the open lower end. Normally, a bed of separation media, such as an extraction media, is positioned inside the open channel and in contact with the bottom frit. However, in some cases a column with a bottom frit and no bed of media can be useful for certain techniques encompassed by this invention. For example, a pipette tip with a frit at the open lower end can be used to take up a liquid sample without taking up solid or particulate material in the sample. The solid or particulate material might be gel fragments, beads, etc. In this context, the bottom frit is essentially acting as a filter, and a membrane screen can serve as a particularly appropriate bottom frit.

In certain embodiments, an optional top frit may be employed. For example, in some embodiments a second frit is bonded to and extends across the open channel between the bottom frit and the open upper end of the column body. In this embodiment, the top frit, bottom frit and column body (i.e., the inner surface of the channel) define an extraction media chamber wherein a bed of extraction media is positioned. The frits should be securely attached to the column body and extend across the opening and/or open end so as to completely occlude the channel, thereby substantially confining the bed of extraction media inside the extraction media chamber. In preferred embodiments of the invention the bed of extraction media occupies at least 80% of the volume of the extraction media chamber, more preferably 90%, 95%, 99%, or substantially 100% of the volume. In some preferred embodiments the invention the space between the extraction media bed and the upper and lower frits is negligible, i.e., the frits are in substantial contact with upper and lower surfaces of the extraction media bed, holding a well-packed bed of extraction media securely in place.

In some preferred embodiments of the invention the bottom frit is located at the open lower end of the column body. This configuration is shown in the figures and exemplified in the Examples, but is not required, i.e., in some embodiments the bottom frit is located at some distance up the column body from the open lower end. However, in view of the advantage the come with minimizing dead volume in the column, it is desirable that the lower frit and extraction media chamber be located at or near the lower end. In some cases this can mean that the bottom frit is attached to the face of the open lower end, as shown in FIGS. 1-10. However, in some cases there can be some portion of the lower end extending beyond the bottom frit, as exemplified by the embodiment depicted in FIG. 11. For the purposes of this invention, so long as the length as this extension is such that it does not substantially introduce dead volume into the extraction column or otherwise adversely impact the function of the column, the bottom frit is considered to be located at the lower end of the column body. In some embodiments of the invention the volume defined by the bottom frit, channel surface, and the face of the open lower end (i.e., the channel volume below the bottom frit) is less than the volume of the extraction media chamber, or less than 10% of the volume of the extraction media chamber, or less than 1% of the volume of the extraction media chamber.

In some embodiments of the invention, the extraction media chamber is positioned near one end of the column, which for purposes of explanation will be described as the bottom end of the column. The area of the column body channel above the extraction media chamber can be can be quite large in relation to the size of the extraction media chamber. For example, in some embodiments the volume of the extraction chamber is equal to less than 50%, less than 20, less than 10%, less than 5%, less than 2%, less than 1% or less than 0.5% of the total internal volume of the column body. In operation, solvent can flow through the open lower end of the column, through the bed of extraction media and out of the extraction media chamber into the section of the channel above the chamber. For example, when the column body is a pipette tip, the open upper end can be fitted to a pipettor and a solution drawn through the extraction media and into the upper part of the channel.

The frits used in the invention are preferably characterized by having a low pore volume. Some preferred embodiments invention employ frits having pore volumes of less than 1 microliter (e.g., in the range of 0.015-1 microliter, 0.03-1 microliter, 0.1-1 microliter or 0.5-1 microliter), preferably less than 0.5 microliter (e.g., in the range of 0.015-0.5 microliter, 0.03-0.5 microliter or 0.1-0.5 microliter), less than 0.1 microliter (e.g., in the range of 0.015-0.1 microliter or 0.03-0.1 microliter) or less than 0.03 microliters (e.g., in the range of 0.015-0.03 microliter).

Frits of the invention preferably have pore openings or mesh openings of a size in the range of about 5-100 μm, more preferably 10-100 μm, and still more preferably 15-50 μm, e.g., about 43 μm. The performance of the column is typically enhanced by the use of frits having pore or mesh openings sufficiently large so as to minimize the resistance to flow. The use of membrane screens as described herein typically provide this low resistance to flow and hence better flow rates, reduced back pressure and minimal distortion of the bed of extraction media. The pore or mesh openings of course should not be so large that they are unable to adequately contain the extraction media in the chamber.

Some frits used in the practice of the invention are characterized by having a low pore volume relative to the interstitial volume of the bed of extraction media contained by the frit. Thus, in preferred embodiments of the invention the frit pore volume is equal to 10% or less of the interstitial volume of the bed of extraction media (e.g., in the range 0.1-10%, 0.25-10%, 1-10% or 5-10% of the interstitial volume), more preferably 5% or less of the interstitial volume of the bed of extraction media (e.g., in the range 0.1-5%, 0.25-5% or 1-5% of the interstitial volume), and still more preferably 1% or less of the interstitial volume of the bed of extraction media (e.g., in the range 0.01-1%, 0.05-1% or 0.1-1% of the interstitial volume).

The pore density will allow flow of the liquid through the membrane and is preferably 10% and higher to increase the flow rate that is possible and to reduce the time needed to process the sample.

Some embodiments of the invention employ a thin frit, preferably less than 350 μm in thickness (e.g., in the range of 20-350 μm, 40-350 μm, or 50-350 μm), more preferably less than 200 μm in thickness (e.g., in the range of 20-200 μm, 40-200 μm, or 50-200 μm), more preferably less than 100 μm in thickness (e.g., in the range of 20-100 μm, 40-100 μm, or 50-100 μm), and most preferably less than 75 μm in thickness (e.g., in the range of 20-75 μm, 40-75 μm, or 50-75 μm).

Some preferred embodiments of the invention employ a membrane screen as the frit. The membrane screen should be strong enough to not only contain the extraction media in the column bed, but also to avoid becoming detached or punctured during the actual packing of the media into the column bed. Membranes can be fragile, and in some embodiments must be contained in a framework to maintain their integrity during use. However, it is desirable to use a membrane of sufficient strength such that it can be used without reliance on such a framework. The membrane screen should also be flexible so that it can conform to the column bed. This flexibility is advantageous in the packing process as it allows the membrane screen to conform to the bed of extraction media, resulting in a reduction in dead volume.

The membrane can be a woven or non-woven mesh of fibers that may be a mesh weave, a random orientated mat of fibers i.e. a "polymer paper," a spunbonded mesh, an etched or "pore drilled" paper or membrane such as nuclear track etched membrane or an electrolytic mesh (see, e.g., U.S. Pat. No. 5,556,598). The membrane may be, e.g., polymer, glass, or metal provided the membrane is low dead volume, allows movement of the various sample and processing liquids through the column bed, may be attached to the column body, is strong enough to withstand the bed packing process, is strong enough to hold the column bed of beads, and does not interfere with the extraction process i.e. does not adsorb or denature the sample molecules.

The frit can be attached to the column body by any means which results in a stable attachment. For example, the screen can be bonded to the column body through welding or gluing. Gluing can be done with any suitable glue, e.g., silicone, cyanoacrylate glue, epoxy glue, and the like. The glue or weld joint must have the strength required to withstand the process of packing the bed of extraction media and to contain the extraction media with the chamber. For glue joints, a glue should be selected employed that does not adsorb or denature the sample molecules.

For example, glue can be used to attach a membrane to the tip of a pipet tip-based extraction column, i.e., a column wherein the column body is a pipet tip. A suitable glue is applied to the end of the tip. In some cases, a rod may be inserted into the tip to prevent the glue from spreading beyond the face of the body. After the glue is applied, the tip is brought into contact with the membrane frit, thereby attaching the membrane to the tip. After attachment, the tip and membrane may be brought down against a hard flat surface and rubbed in a circular motion to ensure complete attachment of the membrane to the column body. After drying, the excess membrane may be trimmed from the column with a razor blade.

Alternatively, the column body can be welded to the membrane by melting the body into the membrane, or melting the membrane into the body, or both. In one method, a membrane is chosen such that its melting temperature is higher than the melting temperature of the body. The membrane is placed on a surface, and the body is brought down to the membrane and heated, whereby the face of the body will melt and weld the membrane to the body. The body may be heated by any of a variety of means, e.g., with a hot flat surface, hot air or ultrasonically. Immediately after welding, the weld may be cooled with air or other gas to improve the likelihood that the weld does not break apart.

Alternatively, a frit can be attached by means of an annular pip, as described in U.S. Pat. No. 5,833,927. This mode of attachment is particularly suited to embodiment where the frit is a membrane screen.

The frits of the invention, e.g., a membrane screen, can be made from any material that has the required physical properties as described herein. Examples of suitable materials include nylon, polyester, polyamide, polycarbonate, cellulose, polyethylene, nitrocellulose, cellulose acetate, polyvinylidine difluoride, polytetrafluoroethylene (PTFE), polypropylene, polysulfone, metal and glass. A specific example of a membrane screen is the 43 µm pore size Spectra/Mesh® polyester mesh material which is available from Spectrum Labs (Ranch Dominguez, Calif., PN 145837).

Pore size characteristics of membrane filters can be determined, for example, by use of method #F316-30, published by ASTM International, entitled "Standard Test Methods for Pore Size Characteristics of Membrane Filters by Bubble Point and Mean Flow Pore Test."

The polarity of the membrane screen can be important. A hydrophilic screen will promote contact with the bed and promote the air-liquid interface setting up a surface tension. A hydrophobic screen would not promote this surface tension and therefore the threshold pressures to flow would be different. A hydrophilic screen is preferred in certain embodiments of the invention.

However, depending upon the context in which the device is used, it can be preferable to use either a hydrophilic membrane, such as polyester, or a hydrophobic membrane, such as nylon, or a combination of hydrophobic and hydrophilic membranes, e.g., a hydrophilic membrane on top and hydrophilic membrane on the bottom. For example, the use of a hydrophobic membrane as the top and/or bottom frit can improve flow characteristics of the column, particularly in automated implementations of the invention, such as by means of a robotic liquid handling system. Without intending to be bound by any particularly theory of operation, it seems likely that use of a hydrophobic membrane in conjunction with aqueous solutions will generate reduced surface tension, resulting in reduced bubble point and thus reduced back pressure. Examples of hydrophobic and hydrophilic membranes would include, for example, membranes comprising nylon and polyester, respectively.

In certain embodiments of the invention, a wad of fibrous material is included in the device, which extends across the open channel between the bottom frit and the open upper end of the column body, wherein the wad of fibrous material, bottom frit and open channel define a media chamber, wherein the bed of extraction media is positioned within the media chamber. In some embodiments, the wad of fibrous material is used in lieu of an upper frit, i.e., there is a single lower frit and a wad of fibrous material defining the media chamber. In other embodiments, both a top frit and a wad of fibrous material are used. For example, the fibrous material can be positioned within the open channel and in contact with the top frit, e.g., the wad of fibrous material can be positioned between the top frit and the open upper end, or between the bottom and top frits, i.e., within the media chamber.

The wad of fibrous material can have any of a variety of dimensions or sizes. For example, the volume of the wad in certain devices is between 1% and 1000% of the volume of the media chamber, preferably between 5% and 500%, or 10% and 100%, of the volume of the media chamber. In some embodiments, the wad of fibrous material comprises polyester or polyethylene fiber.

Without intending to be bound by any particular theory, it is believed that the wad of fibrous material can facilitate movement of solution through the bed of extraction material by acting as a wicking agent. This particularly the case where a gas such as air is present in or adjacent to the bed of extraction media, which can increase the back pressure of moving liquid through the column, particularly where the gas is a bubble in contact with a membrane screen. A membrane screen, particularly one that is hydrophilic, can result in a relatively high bubble point that causes an increase in back pressure; the use of a wicking agent alleviates this problem.

Extraction Column Assembly

The extraction columns of the invention can be constructed by a variety of methods using the teaching supplied herein. In some preferred embodiments the extraction column can be constructed by the engagement (i.e., attachment) of upper and lower tubular members (i.e., column bodies) that combine to form the extraction column. Examples of this mode of column construction are described in the Examples and depicted in the figures.

In some preferred embodiments of the invention, an extraction column is constructed by the engaging outer and inner column bodies, where each column body has two open ends (e.g., an open upper end and an open lower end) and an open channel connecting the two open ends (e.g., a tubular body, such as a pipette tip). The outer column body has a first frit (preferably a membrane frit) bonded to and extending across the open lower end, either at the very tip of the open end or near the open end. The section of the open channel between the open upper end and the first frit defines an outer column body. The inner column body likewise has a frit (preferably a membrane frit) bonded to and extending across its open lower end.

To construct a column according to this embodiment, an extraction media of interest is disposed within the lower column body, e.g., by orienting the lower column body such that the open lower end is down and filling or partially filling the open channel with the resin, e.g., in the form of a slurry. The inner column body, or at least some portion of the inner column body, is then inserted into the outer column body such that the open lower end of the inner body (where second frit is attached) enters the outer column body first. The inner column body is sealingly positioned within the open channel of the outer column body, i.e., the outer surface of the inner column body forms a seal with the surface of the open. The section of the open channel between the first and second frits contains the extraction media, and this space defines a media chamber. In general, it is advantageous that the volume of the media chamber (and the volume of the bed of extraction media positioned with said media chamber) is less than the outer column body, since this difference in volume facilitates the introduction of extraction media into the outer column body and hence simplifies the production process. This is particularly advantageous in embodiments of the invention wherein the extraction columns are mass produced.

In certain embodiments of the above manufacturing process, the inner column body is stably affixed to the outer column body by frictional engagement with the surface of the open channel.

Figure 2:
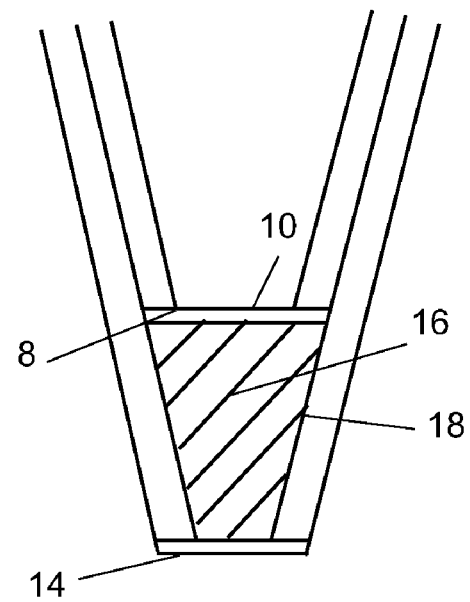
FIG. 2 is an enlarged view of the extraction column of FIG. 1.

In some embodiments, one or both of the column bodies are tubular members, particularly pipette tips, sections of pipette tips or modified forms of pipette tips. For example, an embodiment of the invention wherein in the two tubular members are sections of pipette tips is depicted in FIG. 1 (FIG. 2 is an enlarged view of the open lower end and extraction media chamber of the column). This embodiment is constructed from a frustoconical upper tubular member 2 and a frustoconical lower tubular member 3 engaged therewith. The engaging end 6 of the lower tubular member has a tapered bore that matches the tapered external surfaced of the engaging end 4 of the upper tubular member, the engaging end of the lower tubular member receiving the engaging end of the upper tubular member in a telescoping relation. The tapered bore engages the tapered external surface snugly so as to form a good seal in the assembled column.

A membrane screen 10 is bonded to and extends across the tip of the engaging end of the upper tubular member and constitutes the upper frit of the extraction column. Another membrane screen 14 is bonded to and extends across the tip of the lower tubular member and constitutes the lower frit of the extraction column. The extraction media chamber 16 is defined by the membrane screens 10 and 14 and the channel surface 18, and is packed with extraction media.

The pore volume of the membrane screens 10 and 14 is low to minimize the dead volume of the column. The sample and desorption solution can pass directly from the vial or reservoir into the bed of extraction media. The low dead volume permits desorption of the analyte into the smallest possible desorption volume, thereby maximizing analyte concentration.

The volume of the extraction media chamber 16 is variable and can be adjusted by changing the depth to which the upper tubular member engaging end extends into the lower tubular member, as determined by the relative dimensions of the tapered bore and tapered external surface.

The sealing of the upper tubular member to the lower tubular in this embodiment is achieved by the friction of a press fit, but could alternatively be achieved by welding, gluing or similar sealing methods.

Note that in this and similar embodiments, a portion of the inner column body (in this case, a majority of the pipette tip 2) is not disposed within the first channel, but instead extends out of the outer column body. In this case, the open upper end of the inner column body is adapted for operable attachment to a pump, e.g., a pipettor.

Figure 3:
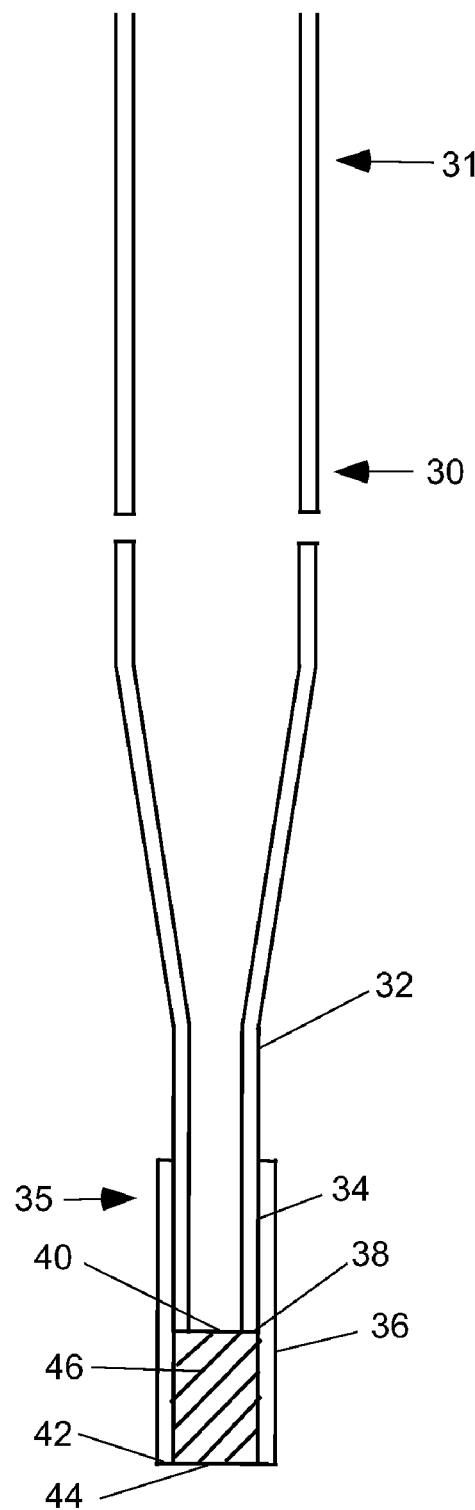
FIG. 3 depicts an embodiment of the invention where the extraction column is constructed from two cylindrical members.

FIG. 3 depicts an embodiment of the invention comprising an upper and lower tubular member engaged in a telescoping relation that does not rely on a tapered fit. Instead, in this embodiment the engaging ends 34 and 35 are cylindrical, with the outside diameter of 34 matching the inside diameter of 35, so that the concentric engaging end form a snug fit. The engaging ends are sealed through a press fit, welding, gluing or similar sealing methods. The volume of the extraction bed can be varied by changing how far the length of the engaging end 34 extends into engaging end 35. Note that the diameter of the upper tubular member 30 is variable, in this case it is wider at the upper open end 31 and tapers down to the narrower engaging end 34. This design allows for a larger volume in the column channel above the extraction media, thereby facilitating the processing of larger sample volumes and wash volumes. The size and shape of the upper open end can be adapted to conform to a pump used in connection with the column. For example, upper open end 31 can be tapered outward to form a better friction fit with a pump such as a pipettor or syringe.

A membrane screen 40 is bonded to and extends across the tip 38 of engaging end 34 and constitutes the upper frit of the extraction column. Another membrane screen 44 is bonded to and extends across the tip 42 of the lower tubular member 36 and constitutes the lower frit of the extraction column. The extraction media chamber 46 is defined by the membrane screens 40 and 44 and the open interior channel of lower tubular member 36, and is packed with extraction media.

Figure 4:
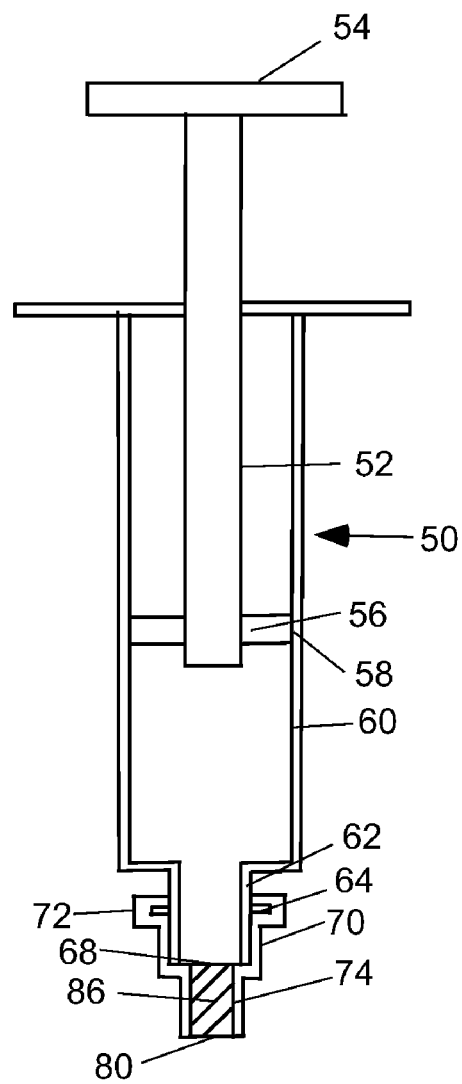
FIG. 4 depicts a syringe pump embodiment of the invention with a cylindrical bed of solid phase media in the tip.
Figure 5:
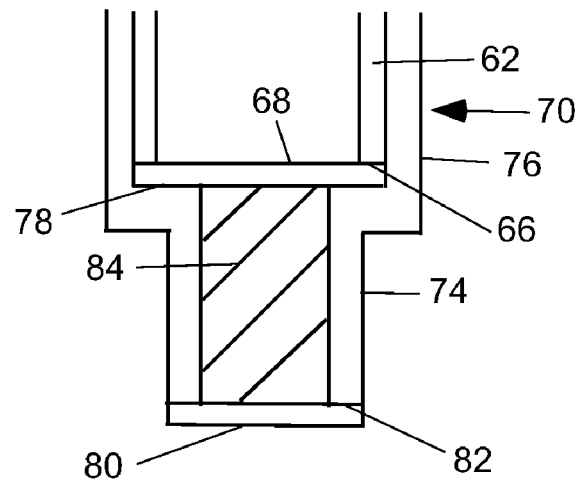
FIG. 5 is an enlarged view of the extraction column element of the syringe pump embodiment of FIG. 4.

FIG. 4 is a syringe pump embodiment of the invention with a cylindrical bed of extraction media in the tip, and FIG. 5 is an enlargement of the top of the syringe pump embodiment of FIG. 4. These figures show a low dead volume column based on using a disposable syringe and column body. Instead of a pipettor, a disposable syringe is used to pump and contain the sample.

The upper portion of this embodiment constitutes a syringe pump with a barrel 50 into which a plunger 52 is positioned for movement along the central axis of the barrel. A manual actuator tab 54 is secured to the top of the plunger 52. A concentric sealing ring 56 is secured to the lower end of the plunger 52. The outer surface 58 of the concentric sealing ring 56 forms a sealing engagement with the inner surface 60 of the barrel 50 so that movement of the plunger 52 and sealing ring 56 up or down in the barrel moves liquid up or down the barrel.

The lower end of the barrel 50 is connected to an inner cylinder 62 having a projection 64 for engaging a Luer adapter. The bottom edge 66 of the inner cylinder 62 has a membrane screen 68 secured thereto. The inner cylinder 62 slides in an outer sleeve 70 with a conventional Luer adaptor 72 at its upper end. The lower segment 74 of the outer sleeve 70 has a diameter smaller than the upper portion 76, outer sleeve 70 forming a ledge 78 positioned for abutment with the lower end 66 and membrane screen 68. A membrane screen 80 is secured to the lower end 82 of the lower segment 74. The extraction media chamber 84 is defined by the upper and lower membrane screens 68 and 80 and the inner channel surface of the lower segment 74. The extraction beads are positioned in the extraction media chamber 84. The volume of extraction media chamber 84 can be adjusted by changing the length of the lower segment 74.

In other embodiments of this general method of column manufacture, the entire inner column body is disposed within the first open channel. In these embodiments the first open upper end is normally adapted for operable attachment to a pump, e.g., the outer column body is a pipette tip and the pump is a pipettor. In some preferred embodiments, the outer diameter of the inner column body tapers towards its open lower end, and the open channel of the outer column body is tapered in the region where the inner column body frictionally engages the open channel, the tapers of the inner column body and open channel being complementary to one another. This complementarity of taper permits the two bodies to fit snuggly together and form a sealing attachment, such that the resulting column comprises a single open channel containing the bed of extraction media bounded by the two frits.

Figures 17A, 17B, 17C:
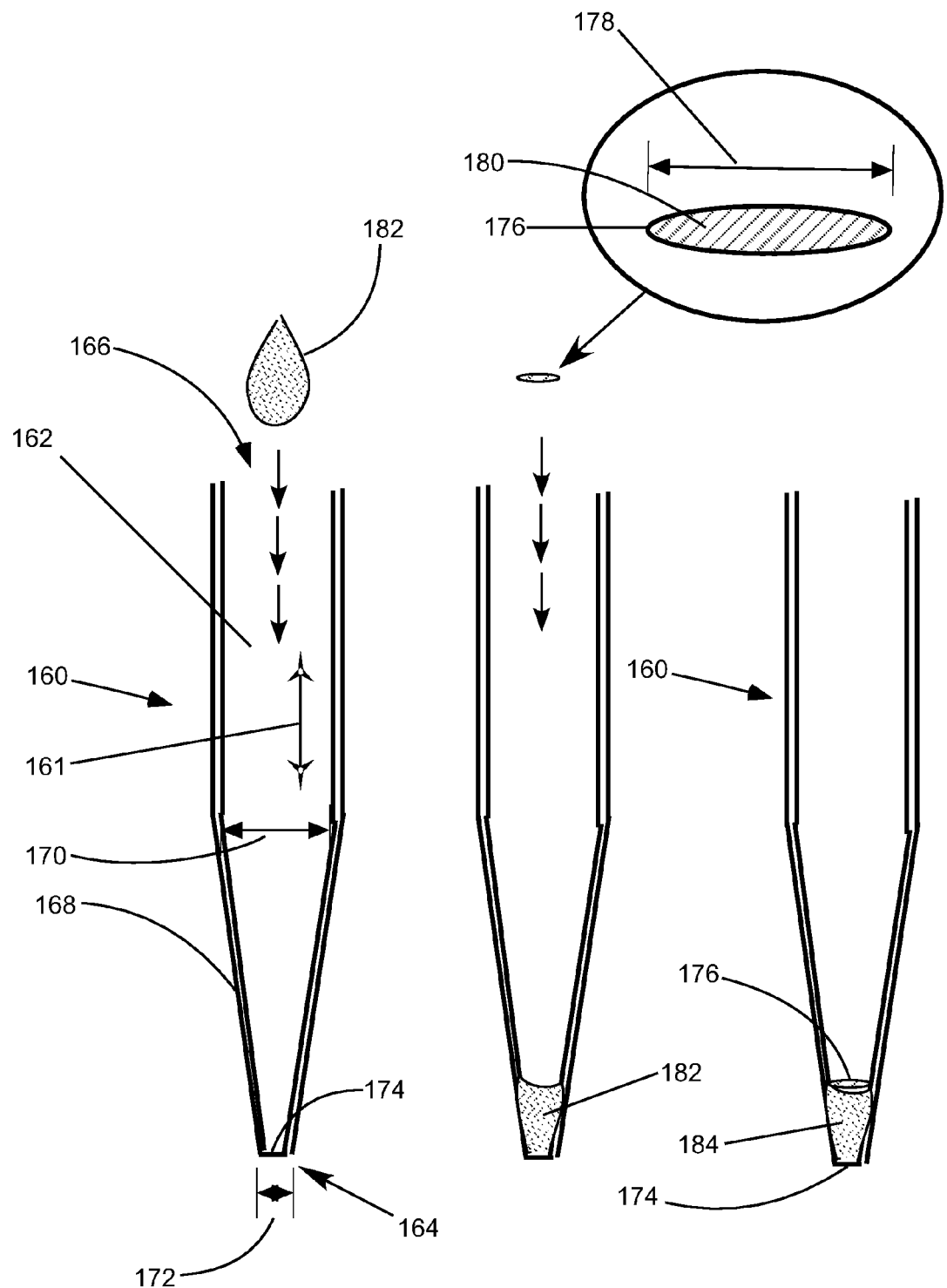
FIGS. 17A-C depict an embodiment of the invention where the extraction column can take the form of a pipette tip.

FIGS. 17A through C illustrate the construction of an example of this embodiment of the extraction columns of the invention. This example includes an outer column body 160 having a longitudinal axis 161, a central through passageway 162 (i.e., an open channel), an open lower end 164 for the uptake and/or expulsion of fluid, and an open upper end 166 for operable attachment to a pump, e.g., the open upper end is in communication with a pipettor or multi-channel pipettor. The communication can be direct or indirect, e.g., through one or more fittings, couplings or the like, so long as operation of the pump effects the pressure in the central through passageway (referred to elsewhere herein as the "head space"). The outer column body includes a frustoconical section 168 of the through passageway 162, which is adjacent to the open lower end 164. The inner diameter of the frustoconical section decreases from a first inner diameter 170, at a position in the frustoconical section distal to the open lower end, to a second inner diameter 172 at the open lower end. A lower frit 174, preferably a membrane screen, is bonded to and extends across the open lower end 164. In a preferred embodiment a membrane frit can be bound to the outer column body by methods described herein, such as by gluing or welding. This embodiment further includes a ring 176 having an outer diameter 178 that is less than the first inner diameter 170 and greater than the second inner diameter 174. An upper frit 180, preferably a membrane screen, is bonded to and extends across the ring.

To construct the column, a desired quantity of extraction media 182, preferably in the form of a slurry, is introduced into the through passageway through the open upper end and positioned in the frustoconical section adjacent to the open lower end. The extraction media preferably forms a packed bed in contact with the lower frit 174. The ring 176 is then introduced into the through passageway through the open upper end and positioned at a point in the frustoconical section where the inner diameter of the frustoconical section matches the outer diameter 178 of the ring, such that the ring makes contact with and forms a seal with the surface of the through passageway (FIG. 17B). The upper frit, lower frit, and the surface of the through passageway bounded by the upper and lower frits define an extraction media chamber 184 (FIG. 17C). The amount of extraction media introduced into the column is normally selected such that the resulting packed bed substantially fills the extraction media chamber, preferably making contact with the upper and lower frits.

Figure 18A:
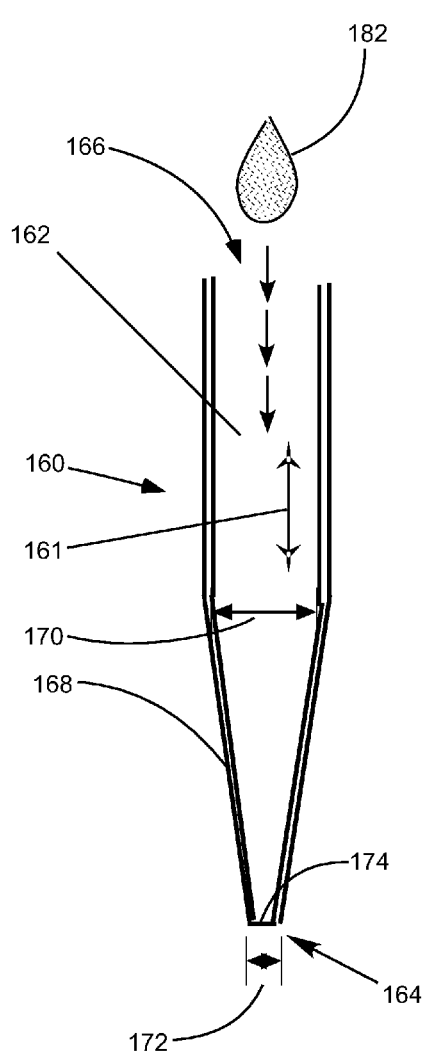
FIGS. 18A-C depict a preferred embodiment of the general embodiment depicted in FIG. 17.
Figure 18B:
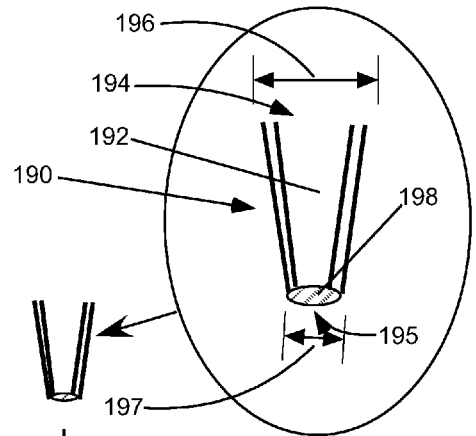
Figure 18C:
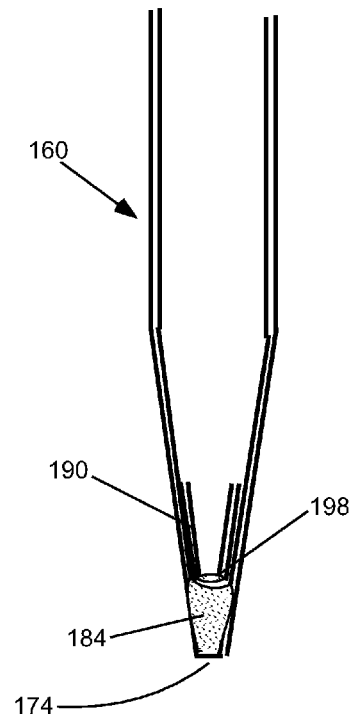

Note that the ring can take any of a number of geometries other than the simple ring depicted in FIG. 17, so long as the ring is shaped to conform with the internal geometry of the frustoconical section and includes a through passageway through which solution can pass. For example, FIG. 18 depicts a preferred embodiment wherein the ring takes the form of a frustoconical member 190 having a central through passageway 192 connecting an open upper end 194 and open lower end 195 (FIG. 18B). The outer diameter of the frustoconical member decreases from a first outer diameter 196 at the open upper end to a second outer diameter 197 at the open lower end. The second outer diameter 197 is greater than the second inner diameter 172 and less than the first inner diameter 170. The first outer diameter 196 is less than or substantially equal to the first inner diameter 170. Upper frit 198 is bonded to and extends across the open lower end 195 (FIGS. 18B and 18C). The frustoconical member 190 is introduced into the through passageway of an outer column body containing a bed of extraction media positioned at the lower frit 174. The tapered outer surface of the frustoconical member matches and the taper of the frustoconical section of the open passageway, and the two surfaces make a sealing contact. The extended frustoconical configuration of this embodiment of the ring facilitates the proper alignment and seating of the ring in the outer passageway.

Because of the friction fitting of the ring to the surface of the central through passageway, it is normally not necessary to use additional means to bond the upper frit to the column. If desired, one could use additional means of attachment, e.g., by bonding, gluing, welding, etc. In some embodiments, the inner surface of the frustoconical section and/or the ring is modified to improve the connection between the two elements, e.g., by including grooves, locking mechanisms, etc.

In the foregoing embodiments, the ring and latitudinal cross sections of the frustoconical section are illustrated as circular in geometry. Alternatively, other geometries could be employed, e.g., oval, polygonal or otherwise. Whatever the geometries, the ring and frustoconical shapes should match to the extent required to achieve and adequately sealing engagement. The frits are preferably, bit not necessarily, positioned in a parallel orientation with respect to one another and perpendicular to the longitudinal axis.

Other embodiments of the invention exemplifying different methods of construction are also described in the examples.

Pump

In some modes of using the extraction columns of the invention, a pump is attached to the upper open end of the column and used to aspirated and discharge the sample from the column. The pump can take any of a variety of forms, so long as it is capable of generating a negative internal column pressure to aspirate a fluid into the column channel through the open lower end. In some preferred embodiments of the invention the pump is also able to generate a positive internal column pressure to discharge fluid out of the open lower end. Alternatively, other methods can be used for discharging solution from the column, e.g., centrifugation.

The pump should be capable of pumping liquid or gas, and should be sufficiently strong so as to be able to draw a desired sample solution, wash solution and/or desorption solvent through the bed of extraction media. In order evacuate liquids from the packed bed and introduce a gas such as air, it is desirable that the pump be able to blow or pull air through the column. A pump capable of generating a strong pressure will be able to more effectively blow gas through the column, driving liquid out of the interstitial volume and contributing to a more highly purified, concentrated analyte.

In some preferred embodiments of the invention the pump is capable of controlling the volume of fluid aspirated and/or discharged from the column, e.g., a pipettor. This allows for the metered intake and outtake of solvents, which facilitates more precise elution volumes to maximize sample recovery and concentration.

Non-limiting examples of suitable pumps include a pipettor, syringe, peristaltic pump, pressurized container, centrifugal pump, electrokinetic pump, or an induction based fluidics pump. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation will vary depending on the step in the extraction procedure, the enrichment of the biomolecule desired, and the dimensions of the extraction column and bed volume.

The sample solution enters the column through one end, and passes through the extraction bed or some portion of the entire length of the extraction bed, eventually exiting the channel through either the same end of the column or out the other end. Introduction of the sample solution into the column can be accomplished by any of a number of techniques for driving or drawing liquid through a channel. Examples would include use of a pump (as described above) gravity, centrifugal force, capillary action, or gas pressure to move fluid through the column. The sample solution is preferably moved through the extraction bed at a flow rate that allows for adequate contact time between the sample and extraction surface. The sample solution can be passed through the bed more than one time, either by circulating the solution through the column in the same direction two or more times, or by passing the sample back and forth through the column two or more times (e.g., by oscillating a plug or series of plugs of desorption solution through the bed). In some embodiments it is important that the pump be able to pump air, thus allowing for liquid to be blown out of the bed. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation in the column will vary depending on the step in the extraction procedure, the enrichment of the biomolecule desired, and the dimensions of the column.

Solvents

Extractions of the invention typically involve the loading of analyte in a sample solution, an optional wash with a rinse solution, and elution of the analyte into a desorption solution. The nature of these solutions will now be described in greater detail.

With regard to the sample solution, it typically consists of the analyte dissolved in a solvent in which the analyte is soluble, and in which the analyte will bind to the extraction surface. Preferably, the binding is strong, resulting in the binding of a substantial portion of the analyte, and optimally substantially all of the analyte will be bound under the loading protocol used in the procedure. The solvent should also be gentle, so that the native structure and function of the analyte is retained upon desorption from the extraction surface. Typically, in the case where the analyte is a biomolecule, the solvent is an aqueous solution, typically containing a buffer, salt, and/or surfactants to solubilize and stabilize the biomolecule. Examples of sample solutions include cells lysates, hybridoma growth medium, cell-free translation or transcription reaction mixtures, extracts from tissues, organs, or biological samples, and extracts derived from biological fluids.

It is important that the sample solvent not only solubilize the analyte, but also that it is compatible with binding to the extraction phase. For example, where the extraction phase is based on ion exchange, the ionic strength of the sample solution should be buffered to an appropriate pH such that the charge of the analyte is opposite that of the immobilized ion, and the ionic strength should be relatively low to promote the ionic interaction. In the case of a normal phase extraction, the sample loading solvent should be non-polar, e.g., hexane, toluene, or the like. Depending upon the nature of the sample and extraction process, other constituents might be beneficial, e.g., reducing agents, detergents, stabilizers, denaturants, chelators, metals, etc.

A wash solution, if used, should be selected such that it will remove non-desired contaminants with minimal loss or damage to the bound analyte. The properties of the wash solution are typically intermediate between that of the sample and desorption solutions.

Desorption solvent can be introduced as either a stream or a plug of solvent. If a plug of solvent is used, a buffer plug of solvent can follow the desorption plug so that when the sample is deposited on the target, a buffer is also deposited to give the deposited sample a proper pH. An example of this is desorption from a protein G surface of IgG antibody which has been extracted from a hybridoma solution. In this example, 10 mM phosphoric acid plug at pH 2.5 is used to desorb the IgG from the tube. A 100 mM phosphate buffer plug at pH 7.5 follows the desorption solvent plug to bring the deposited solution to neutral pH. The deposited material can then be analyzed, e.g., by deposition on an SPR chip.

The desorption solvent should be just strong enough to quantitatively desorb the analyte while leaving strongly bound interfering materials behind. The solvents are chosen to be compatible with the analyte and the ultimate detection method. Generally, the solvents used are known conventional solvents. Typical solvents from which a suitable solvent can be selected include methylene chloride, acetonitrile (with or without small amounts of basic or acidic modifiers), methanol (containing larger amount of modifier, e.g. acetic acid or triethylamine, or mixtures of water with either methanol or acetonitrile), ethyl acetate, chloroform, hexane, isopropanol, acetone, alkaline buffer, high ionic strength buffer, acidic buffer, strong acids, strong bases, organic mixtures with acids/bases, acidic or basic methanol, tetrahydrofuran and water. The desorption solvent may be different miscibility than the sorption solvent.

In the case where the extraction involves binding of analyte to a specific cognate ligand molecule, e.g., an immobilized metal, the desorption solvent can contain a molecule that will interfere with such binding, e.g., imidazole or a metal chelator in the case of the immobilized metal.

Examples of suitable phases for solid phase extraction and desorption solvents are shown in Tables A and B.

TABLE A

|  | Normal Phase Extraction | Reverse Phase Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | $H_2O$, buffers | $H_2O$, buffers, ion-pairing reagent |
| Typical desorption solvent | Ethyl acetate, acetone, $CH_3CN$ (Acetone, acetonitrile, isopropanol, methanol, water, buffers) | $H_2O/CH_3OH$, $H_2O/CH_3CN$ (Methanol, chloroform, acidic methanol, basic methanol, tetrahydrofuran, acetonitrile, acetone, ethyl acetate,) | $H_2O/CH_3OH$, ion-pairing reagent $H_2O/CH_3CN$, ion-pairing reagent (Methanol, chloroform, acidic methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease solvent polarity | Decrease solvent polarity |

TABLE B

| Desorption Solvent Features | Ion Exchange Extraction | Hydrophobic Interaction Extraction | Affinity Phase Extraction |
|---|---|---|---|
| Typical solvent polarity range | High | High | High |
| Typical sample loading solvent | $H_2O$, buffers | $H_2O$, high salt | $H_2O$, buffers |
| Typical desorption solvent | Buffers, salt solutions | $H_2O$, low salt | $H_2O$, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase retained compounds pH or decrease pH | Decrease ionic strength | Change pH, add competing reagent, change solvent polarity, increase heat |

Methods for Using the Extraction Columns

Generally the first step in an extraction procedure of the invention will involve introducing a sample solution containing an analyte of interest into a packed bed of extraction media, typically in the form of a column as described above. The sample can be conveniently introduced into the separation bed by pumping the solution through the column. Note that the volume of sample solution can be much larger than the bed volume. The sample solution can optionally be passed through the column more than one time, e.g., by being pumped back and forth through the bed. This can improve adsorption of analyte, which can be particularly in cases where the analyte is of low abundance and hence maximum sample recovery is desired.

Certain embodiments of the invention are particularly suited to the processing of biological samples, where the analyte of interest is a biomolecule. Of particular relevance are biological macromolecules such as polypeptides, polynucleotides, and polysaccharides, or large complexes containing on or more of these moieties.

The sample solution can be any solution containing an analyte of interest. The invention is particularly useful for extraction and purification of biological molecules, hence the sample solution is often of biological origin, e.g., a cell lysate. In one embodiment of the invention the sample solution is a hybridoma cell culture supernatant.

One advantage of using the low bed volume columns described above is that they allow for high linear velocity of liquid flow through the column (i.e., linear flow rate) without the associated loss of performance and/or development of back pressure seen with more conventional columns. High linear velocities reduce loading time. Because of the high linear velocities employed, it is likely that most of the loading interactions are at the surface of the extraction material.

The linear flow rate through a column in (cm/min) can be determined by dividing the volumetric flow (in mL/min or $cm^3$/min) by the cross-sectional area (in $cm^2$). This calculation implies that the column is acting like an open tube, in that the media is being properly penetrated by the flow of buffer/eluents. Thus, for example, the linear flow rate of a separation having a volumetric flow rate of 1 mL/min through a column with a cross-sectional area of 1 $cm^2$ would be (1 mL/min)/(1 $cm^2$)=1 cm/min.

An exemplary pipet tip column of the present invention might have a bed volume of 20 μL positioned in right-angle frustum (i.e., an inverted cone with the tip chopped off, where the bottom diameter is 1.2 mm and the top diameter is 2.5 mm, and the approximate bed height is 8 mm). The mean diameter is about 1.8 mm, so the mean cross-sectional area of the bed is about 0.025 $cm^2$. At a flow rate of 1 mL/min, the linear flow rate is (1 mL/min)/(0.025 $cm^2$)=40 cm/min. The mean cross-sectional area of the bed at the tip is about 0.011 $cm^2$, and the linear flow rate at the tip is (1 mL/min)/(0.011 cm$^2$)=88 cm/min. It is a feature of certain extraction columns of the invention that they can be effective in methods employing high linear flow rate exceeding flow rates previously used in conventional extraction methods. For example, the invention provides methods (and the suitable extraction columns) that employ linear flow rates of greater than 10 cm/min, 20 cm/min, 30 cm/min, 40 cm/min, 50 cm/min, 60 cm/min, 70 cm/min, 80 cm/min, 90 cm/min, 100 cm/min, 120 cm/min, 150 cm/min, 200 cm/min, 300 cm/min, or higher. In various embodiments of the invention are provided methods and columns that employ linear flow rate ranges having lower limits of 10 cm/min, 20 cm/min, 30 cm/min, 40 cm/min, 50 cm/min, 60 cm/min, 70 cm/min, 80 cm/min, 90 cm/min, 100 cm/min, 120 cm/min, 150 cm/min, or 200 cm/min; and upper limits of 50 cm/min, 60 cm/min, 70 cm/min, 80 cm/min, 90 cm/min, 100 cm/min, 120 cm/min, 150 cm/min, 200 cm/min, 300 cm/min, or higher.

Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.01 mL/min, 0.05 mL/min, 0.1 mL/min, 0.5 mL/min, 1 mL/min, 2 mL/min, or 4 mL/min and upper limit of 0.1 mL/min, 0.5 mL/min, 1 mL/min, 2 mL/min, 4 mL/min, 6 mL/min, 10 mL/min or greater. For example, some embodiments of the invention involve passing a liquid though a packed bed of media having a volume of less than 100 μL at a flow rate of between about 0.1 and about 4 mL/min, or between about 0.5 and 2 mL/min, e.g., a small packed bed of extraction media as described elsewhere herein. In another example, other embodiments of the invention involve passing a liquid though a packed bed of media having a volume of less than 25 μL at a flow rate of between about 0.1 and about 4 mL/min, or between about 0.5 and 2 mL/min.

In some cases, it is desirable to perform one or more steps of a purification process at a relatively slow flow rate, e.g., the loading and/or wash steps, to maximize binding of an analyte of interest to an extraction medium. To facilitate such methods, in certain embodiments the invention provides a pipette comprising a body; a microprocessor; an electrically driven actuator disposed within the body, the actuator in communication with and controlled by the microprocessor; a displacement assembly including a displacing piston moveable within one end of a displacement cylinder having a displacement chamber and having another end with an aperture, wherein said displacing piston is connected to and controlled by said actuator; and a pipette tip in communication with said aperture, wherein the microprocessor is programmable to cause movement of the piston in the cylinder at a rate that results in drawing a liquid into the pipette tip at a desired flow when the tip is in communication with the liquid. The flow rate can be relatively slow, such as the slow flow rates described above, e.g., between about 0.1 and 4 mL/min.

The pipette tip can be a pipette tip column of the invention, e.g., a pipette tip comprising a tip body having an open upper end, an open lower end, and an open channel between the upper and lower ends of the tip body; a bottom frit bonded to and extending across the open channel; a top frit bonded to and extending across the open channel between the bottom frit and the open upper end of the tip body, wherein the top frit, bottom frit, and column body define a media chamber; and a bed of media positioned inside the media chamber.

In some embodiments, the microprocessor is external to the body of the pipettor, e.g., an external PC programmed to control a sample processing procedure. In some embodiments the piston is driven by a motor, e.g., a stepper motor.

The invention provides a pipettor (such as a multi-channel pipettor) suitable for acting as the pump in methods such as those described above. In some embodiments the pipettor comprises an electrically driven actuator. The electrically driven actuator can be controlled by a microprocessor, e.g., a programmable microprocessor. In various embodiments the microprocessor can be either internal or external to the pipettor body. In certain embodiments the microprocessor is programmed to pass a pre-selected volume of solution through the bed of media at a pre-selected flow rate.

The back pressure of a column will depend on the average bead size, bead size distribution, average bed length, average cross sectional area of the bed, back pressure due to the frit and viscosity of flow rate of the liquid passing through the bed. For a 10 uL bed described in this application, the backpressure at 2 mL/min flow rate ranged from 0.5 to 2 psi. Other columns dimensions will result in backpressures ranging from, e.g., 0.1 psi to 30 psi depending on the parameters described above. The average flow rate ranges from 0.05 mL/min to 10 mL/min, but will commonly be 0.1 to 2 mL/min range with 0.2-1 mL/min flow rate being most common for the 10 uL bed columns.

In some embodiments, the invention provides columns characterized by small bed volumes, small average cross-sectional areas, and/or low backpressures. This is in contrast to previously reported columns having small bed volumes but having higher backpressures, e.g., for use in HPLC. Examples include backpressures under normal operating conditions (e.g., 2 mL/min in a column with 10 μL bed) less than 30 psi, less than 10 psi, less than 5 psi, less than 2 psi, less than 1 psi, less than 0.5 psi, less than 0.1 psi, less than 0.05 psi, less than 0.01 psi, less than 0.005 psi, or less than 0.001 psi. Thus, some embodiments of the invention involve ranges of backpressures extending from a lower limit of 0.001, 0.005, 0.01, 0.02, 0.03, 0.05, 0.1, 0.2, 0.3, 0.5, 1, 2, 3, 5, 10 or 20 psi, to an upper limit of 0.1, 0.5, 1, 2, 3, 5, 10, 20, 30, 40, 50, 60, 70, 80, 90 or 100 psi (1 psi=6.8948 kPa). An advantage of low back pressures is there is much less tendency of soft resins, e.g., low-crosslinked agarose or sepharose-based beads, to collapse. Because of the low backpressures, many of these columns can be run using only gravity to drive solution through the column. Other technologies having higher backpressures need a higher pressure to drive solution through, e.g., centrifugation at relatively high speed. This limits the use of these types of columns to resin beads that can withstand this pressure without collapsing.

The term "cross-sectional area" refers to the area of a cross section of the bed of extraction media, i.e., a planar section of the bed generally perpendicular to the flow of solution through the bed and parallel to the frits. In the case of a cylindrical or frustoconical bed, the cross section is generally circular and the cross sectional area is simply the area of the circle (area=pi×r$^2$). In embodiments of the invention where the cross sectional area varies throughout the bed, such as the case in many of the preferred embodiments described herein having a tapered, frustoconical shape, the average cross-sectional area is an average of the cross sectional areas of the bed. As a good approximation, the average cross-sectional area of a frustoconical bed is the average of the circular cross-sections at each end of the bed. The average cross-sectional area of the bed of extraction media can be quite small in some of the columns of the invention, particularly low backpressure columns. Examples include cross-sectional areas of less than about 100 mm$^2$, less than about 50 mm$^2$, less than about 20 mm$^2$, less than about 10 mm$^2$, less than about 5 mm$^2$, or less than about 1 mm$^2$. Thus, some embodiments of the invention involve ranges of cross-sectional areas extending from a lower limit of 0.1, 0.5, 1, 2, 3, 5, 10 or 20 mm$^2$ to an upper limit of 1, 2, 3, 5, 10, 20, 30, 40, 50, 60, 70, 80, 90 or 100 mm$^2$.

After the sample solution has been introduced into the bed and analyte allowed to adsorb, the sample solution is substantially evacuated from the bed, leaving the bound analyte. It is not necessary that all sample solution be evacuated from the bed, but diligence in removing the solution can improve the purity of the final product. An optional wash step between the adsorption and desorption steps can also improve the purity of the final product. Typically water or a buffer is used for the wash solution. The wash solution is preferably one that will, with a minimal desorption of the analyte of interest, remove excess matrix materials, lightly adsorbed or non-specifically adsorbed materials so that they do not come off in the elution cycle as contaminants. The wash cycle can include solvent or solvents having a specific pH, or containing components that promote removal of materials that interact lightly with the extraction phase. In some cases, several wash solvents might be used in succession to remove specific material, e.g., PBS followed by water. These cycles can be repeated as many times as necessary. In other cases, where light contamination can be tolerated, a wash cycle can be omitted.

The volume of desorption solvent used can be very small, approximating the interstitial volume of the bed of extraction media. In preferred embodiments of the invention the amount of desorption solvent used is less than 10-fold greater than the interstitial volume of the bed of extraction media, more preferably less than 5-fold greater than the interstitial volume of the bed of extraction media, still more preferably less than 3-fold greater than the interstitial volume of the bed of extraction media, still more preferably less than 2-fold greater than the interstitial volume of the bed of extraction media, and most preferably is equal to or less than the interstitial volume of the bed of extraction media. For example, ranges of desorption solvent volumes appropriate for use with the invention can have a lower limit of 1%, 5%, 10%, 15%, 20%, 30%, 40%, 50%, 60%, 70%, 80%, 90%, 100%, 150%, 200% or 300% of the interstitial volume, and an upper limit of 50%, 100%, 200%, 300%, 400%, 500%, 500%, 600%, 700%, 800%, or 1000% of the interstitial volume, e.g., 10 to 200% of the interstitial volume, 20 to 100% of the interstitial volume, 10 to 50%, 100% to 500%, 200 to 1000%, etc., of the interstitial volume.

Alternatively, the volume of desorption solvent used can be quantified in terms of percent of bed volume (i.e., the total volume of media plus interstitial space) rather than percent of interstitial volume. For example, ranges of desorption solvent volumes appropriate for use with the invention can have a lower limit of 1%, 5%, 10%, 15%, 20%, 30%, 40%, 50%, 60%, 70%, 80%, 90%, 100%, 150%, 200% or 300% of the bed volume, and an upper limit of 50%, 100%, 200%, 300%, 400%, 500%, 500%, 600%, 700%, 800%, or 1000% of the bed volume, e.g., 10 to 200% of the bed volume, 20 to 100% of the bed volume 10 to 50%, 100% to 500%, 200 to 1000%, etc., of the bed volume.

In some embodiments of the invention, the amount of desorption solvent introduced into the column is less than 100 µL, less than 20 µL, less than 15 µL, less than 10 µL, less than 5 µL, or less than 1 uL. For example, ranges of desorption solvent volumes appropriate for use with the invention can have a lower limit of 0.1 µL, 0.2 µL, 0.3 µL, 0.5 µL, 1 µL, 2 µL, 3 µL, 5 µL, or 10 µL, and an upper limit of 2 µL, 3 µL, 5 µL, 10 µL, 15 µL, 20 µL, 30 µL, 50 µL, or 100 µL, e.g., in between 1 and 15 µL, 0.1 and 10 µL, or 0.1 and 2 µL.

The use of small volumes of desorption solution enables one to achieve high enrichment factors in the described methods. The term "enrichment factor" as used herein is defined as the ratio of the sample volume divided by the elution volume, assuming that there is no contribution of liquid coming from the dead volume. To the extent that the dead volume either dilutes the analytes or prevents complete adsorption, the enrichment factor is reduced. For example, if 1000 µL of sample solution is loaded onto the column and the bound analyte eluted in 10 µL of desorption solution, the calculated enrichment factor is 100. Note that the calculated enrichment factor is the maximum enrichment that can be achieved with complete capture and release of analyte. Actual achieved enrichments will typically lower due to the incomplete nature of most binding and release steps. Various embodiments of the invention can achieve ranges of enrichment factors having a lower limit of 1, 10, 100, or 1000, and an upper limit of 10, 100, 1000, 10,000 or 100,000.

Sometimes in order to improve recovery it is desirable to pass the desorption solvent through the extraction bed multiple times, e.g., by repeatedly aspirating and discharging the desorption solvent through the extraction bed and lower end of the column. Step elutions can be performed to remove materials of interest in a sequential manner. Air may be introduced into the bed at this point (or at any other point in the procedure), but because of the need to control the movement of the liquid through the bed, it is not preferred.

The desorption solvent will vary depending upon the nature of the analyte and extraction media. For example, where the analyte is a his-tagged protein and the extraction media an IMAC resin, the desorption solution will contain imidazole or the like to release the protein from the resin. In some cases desorption is achieved by a change in pH or ionic strength, e.g., by using low pH or high ionic strength desorption solution. A suitable desorption solution can be arrived at using available knowledge by one of skill in the art.

Extraction columns and devices of the invention should be stored under conditions that preserve the integrity of the extraction media. For example, columns containing agarose- or sepharose-based extraction media should be stored under cold conditions (e.g., 4 degrees Celsius) and in the presence of 0.01 percent sodium azide or 20 percent ethanol. Prior to extraction, a conditioning step may be employed. This step is to ensure that the tip is in a uniform ready condition, and can involve treating with a solvent and/or removing excess liquid from the bed. If agarose or similar gel materials are used, the bed should be kept fully hydrated before use.

Often it is desirable to automate the method of the invention. For that purpose, the subject invention provides a device for performing the method comprising a column containing a packed bed of extraction media, a pump attached to one end of said column, and an automated means for actuating the pump.

The automated means for actuating the pump can be controlled by software. This software controls the pump, and can be programmed to introduce desired liquids into a column, as well as to evacuating the liquid by the positive introduction of gas into the column if so desired.

For example, in certain embodiments the invention provides a general method for passing liquid through a packed-bed pipette tip column comprising the steps of:
 a) providing a first column comprising:
  i. a column body having an open upper end for communication with a pump, a first open lower end for the uptake and dispensing of fluid, and an open passageway between the upper and lower ends of the column body;

ii. a bottom frit attached to and extending across the open passageway;

iii. a top frit attached to and extending across the open passageway between the bottom frit and the open upper end of the column body, wherein the top frit, bottom frit, and surface of the passageway define a media chamber;

iv. a first packed bed of media positioned inside the media chamber;

v. a first head space defined as the section of the open passageway between the open upper end and the top frit, wherein the head space comprises a gas having a first head pressure; and vi. a pump sealingly attached to the open upper end, where actuation of the pump affects the first head pressure, thereby causing fluid to be drawn into or expelled from the bed of media;

b) contacting said first open lower end with a first liquid;

c) actuating the pump to draw the first liquid into the first open lower end and through the first packed bed of media; and d) actuating the pump to expel at least some of the first liquid through the first packed bed of media and out of the first open lower end.

In certain embodiments, the invention further comprises the following steps subsequent to step (d):

e) contacting said first open lower end with a second liquid, which is optionally the same as the first liquid;

f) actuating the pump to draw second liquid into the first open lower end and through the first packed bed of media; and g) actuating the pump to expel at least some of the second liquid through the first packed bed of media and out of the first open lower end.

In certain embodiments, the first head pressure of the first column is adjusted between steps (d) and (f) to render the head pressure closer to a reference pressure. For example, in certain embodiments the first head pressure of the first column is adjusted between steps (d) and (f) to render the first head pressure substantially equal to a reference head pressure. Likewise, in certain embodiments the reference head pressure is predetermined and/or is the head pressure of the first column prior to step (c).

In a number of embodiments, the above-described method further comprise the steps of:

h) providing a second column comprising:

i. a column body having an open upper end for communication with a pump, a second open lower end for the uptake and dispensing of fluid, and an open passageway between the upper and lower ends of the column body;

ii. a bottom frit attached to and extending across the open passageway;

iii. a top frit attached to and extending across the open passageway between the bottom frit and the open upper end of the column body, wherein the top frit, bottom frit, and surface of the passageway define a media chamber;

iv. a second packed bed of media positioned inside the media chamber;

v. a second head space defined as the section of the open passageway between the open upper end and the top frit, wherein the head space comprises a gas having a second head pressure; and vi. a pump sealingly attached to the second open upper end, where actuation of the pump affects the second head pressure, thereby causing fluid to be drawn into or expelled from the second packed bed of media;

i) contacting said second open lower end with a third liquid, which is optionally the same as the first liquid;

j) actuating the pump to draw the third liquid into the second open lower end and through the second packed bed of media;

k) actuating the pump to expel at least some of the third liquid through the second packed bed of media and out of the second open lower end.

l) contacting said second open lower end with a fourth liquid, which is optionally the same as the third liquid;

m) actuating the pump to draw fourth liquid into the second open lower end and through the second packed bed of media; and n) actuating the pump to expel at least some of the fourth liquid through the second packed bed of media and out of the second open lower end, wherein the head pressure of the second column is adjusted between steps (k) and (m) to render the head pressure closer to a reference pressure.

In the foregoing methods, steps (b) through (g) can be performed prior to steps (i) through (n). Alternatively, steps (b) through (g) can be performed concurrently and in parallel with steps (i) through (n). In either case, the reference head pressure can be the head pressure of the first column immediately prior to the commencement of step (f). The pump can be a multi-channel pipettor and the first column can be attached to a first channel of the multi-channel pipettor and the second column can be attached to a second channel of the multi-channel pipettor. Between steps (d) and (f) the first head pressure can be adjusted to render the first and second head pressures more uniform. In some cases the method is applied concurrently and in parallel to at least six pipette tip columns sealingly attached to said multi-channel pipettor, wherein each pipette tip column comprises a head space having a head pressure, and wherein the head pressures of the at least six pipette tip columns are adjusted to render the head pressures more uniform.

In certain embodiments, the first head pressure is adjusted by breaking the sealing attachment between the pump and the open upper end of the first column, exposing the head space to ambient pressure, and sealingly reattaching the pump to the open upper end of the first column.

In certain embodiments, the second head pressure is adjusted by breaking the sealing attachment between the pump and the open upper end of the first column, exposing the head space to ambient pressure, and sealingly reattaching the pump to the open upper end of the first column.

In certain embodiments, the first column comprises a valve in communication with the first head space, and the first head pressure is adjusted by opening this valve, thereby causing gas to enter or exit the first head space.

In certain embodiments, the second column comprises a valve in communication with the second head space, and the second head pressure is adjusted by opening this valve, thereby causing gas to enter or exit the first head space.

In certain embodiments, the first head pressure and/or second head pressure are adjusted by using the pump to cause gas to enter or exit the head space. The first column can comprise a pressure sensor in operative communication with said first head space, wherein said pressure sensor is used to monitor the first head pressure and to determine the amount of gas pumped into or from the head space. The first column can comprise a first pressure sensor in operative communication with said first head space, a second pressure sensor in operative communication with said second head space, which is optionally the same as the first pressure sensor, wherein said pressure sensors are used to monitor the first and second head pressures and to determine the amount of gas pumped into or from the second head space.

The method of claim 3, wherein the first packed bed of media comprises an interstitial space, and wherein the first head pressure is adjusted by removing bulk liquid from the interstitial space, thereby allowing gas to enter or exit the first head space through the first open lower end and the packed bed of media.

In certain embodiments, the second packed bed of media comprises an interstitial space, wherein the second head pressure is adjusted by removing bulk liquid from the interstitial space, thereby allowing gas to enter or exit the second head space through the first open lower end and the packed bed of media.

In certain embodiments, throughout the method the media chamber remains sealed so as to prevent air from entering or leaving the head space. In some cases, actuation of the pump to draw liquid into the first open lower end comprises inducing a negative head pressure that is sufficient to draw up a desired quantity of liquid but which is not so great as to cause air to enter the media chamber through the bottom frit. For example, in some instances the induced negative pressure is predetermined to be sufficient to draw up a desired quantity of liquid but not so great as to cause air to enter the media chamber through the bottom frit, e.g., a membrane frit. In some cases, after the liquid has been drawn into the media chamber the outer surface of the bottom frit is in contact with air, but the air is prevented from entering or traversing the media chamber by a surface tension that resists the passage of gas through the membrane frit and media chamber. This can be accomplished, for example, when the magnitude of the negative pressure is predetermined to be sufficient draw the liquid into the media chamber but not so great as to overcome the surface tension that resists the passage of gas through the membrane frit and media chamber. In some cases there is a surface tension that resists the initial entry of the liquid through the open lower end of the column body and into the media chamber, and the magnitude of the negative pressure is predetermined to be sufficient to overcome the surface tension that resists the initial entry of the liquid through the open lower end of the column body and into the media chamber.

In some instances where throughout the method the media chamber remains sealed so as to prevent air from entering or leaving the head space, throughout the method the packed bed of media positioned inside the media chamber comprises an interstitial space that is substantially full of a liquid, said liquid forming the seal that prevents air from entering or leaving the head space.

In some instances where throughout the method the media chamber remains sealed so as to prevent air from entering or leaving the head space, the step of providing said first column comprises the steps of:

a) providing a first column comprising:
  i. a column body having an open upper end for communication with a pump, a first open lower end for the uptake and dispensing of fluid, and an open passageway between the upper and lower ends of the column body;
  ii. a bottom frit attached to and extending across the open passageway;
  iii. a top frit attached to and extending across the open passageway between the bottom frit and the open upper end of the column body, wherein the top frit, bottom frit, and surface of the passageway define a media chamber;
  iv. a first packed bed of media positioned inside the media chamber, wherein the packed bed of media comprises an interstitial space that is substantially full of a storage liquid, said storage liquid forming the seal that prevents air from entering or leaving the head space; and
  v. a first head space defined as the section of the open passageway between the open upper end and the top frit, wherein the head space comprises a gas having a first head pressure; and
b) sealingly attaching said pump to the open upper end, wherein after attachment to the pump the interstitial space of said bed of media remains substantially full of storage liquid, thereby maintaining a seal that prevents air from entering or leaving the head space.

In certain embodiments, the storage liquid is a water miscible solvent having a viscosity greater than that of water. In certain embodiments the water miscible solvent has a boiling point greater than 250° C. The water miscible solvent can comprise 50% of the storage liquid. In some preferred embodiments the water miscible solvent comprises a diol, triol, or polyethylene glycol of n=2 to n=150, e.g., glycerol.

The various embodiments described above that involve adjusting or controlling head pressure are particularly useful in embodiments of the invention that involve the use of automated or robotic liquid handling systems, e.g., automated multichannel pipettors. Thus, the various columns discussed can be different columns use simultaneously on a multichannel automated system, or in some cases different columns used sequentially on the same channel.

Multiplexing

In some embodiments of the invention a plurality of columns is run in a parallel fashion, e.g., multiplexed. This allows for the simultaneous, parallel processing of multiple samples. A description of multiplexing of extraction capillaries is provided in U.S. patent application Ser. Nos. 10/434,713 and 10/733,534, and the same general approach can be applied to the columns and devices of the subject invention.

Multiplexing can be accomplished, for example, by arranging the columns in parallel so that fluid can be passed through them concurrently. When a pump is used to manipulate fluids through the column, each column in the multiplex array can have its own pump, e.g., syringe pumps activated by a common actuator. Alternatively, columns can be connected to a common pump, a common vacuum device, or the like. In another example of a multiplex arrangement, the plurality of columns is arranged in a manner such that they can be centrifuged, with fluid being driven through the columns by centrifugal force.

In one embodiment, sample can be arrayed from an extraction column to a plurality of predetermined locations, for example locations on a chip or microwells in a multi-well plate. A precise liquid processing system can be used to dispense the desired volume of eluent at each location. For example, an extraction column containing bound analyte takes up 50 μL of desorption solvent, and 1 μL drops are spotted into microwells using a robotic system such as those commercially available from Zymark (e.g., the SciClone sample handler), Tecan (e.g., the Genesis NPS, Aquarius or TeMo) or Cartesian Dispensing (e.g., the Honeybee benchtop system), Packard (e.g., the MiniTrak5, Evolution, Platetrack. or Apricot), Beckman (e.g., the FX-96) and Matrix (e.g., the Plate Mate 2 or SerialMate). This can be used for high-throughput assays, crystallizations, etc.

Figure 13:
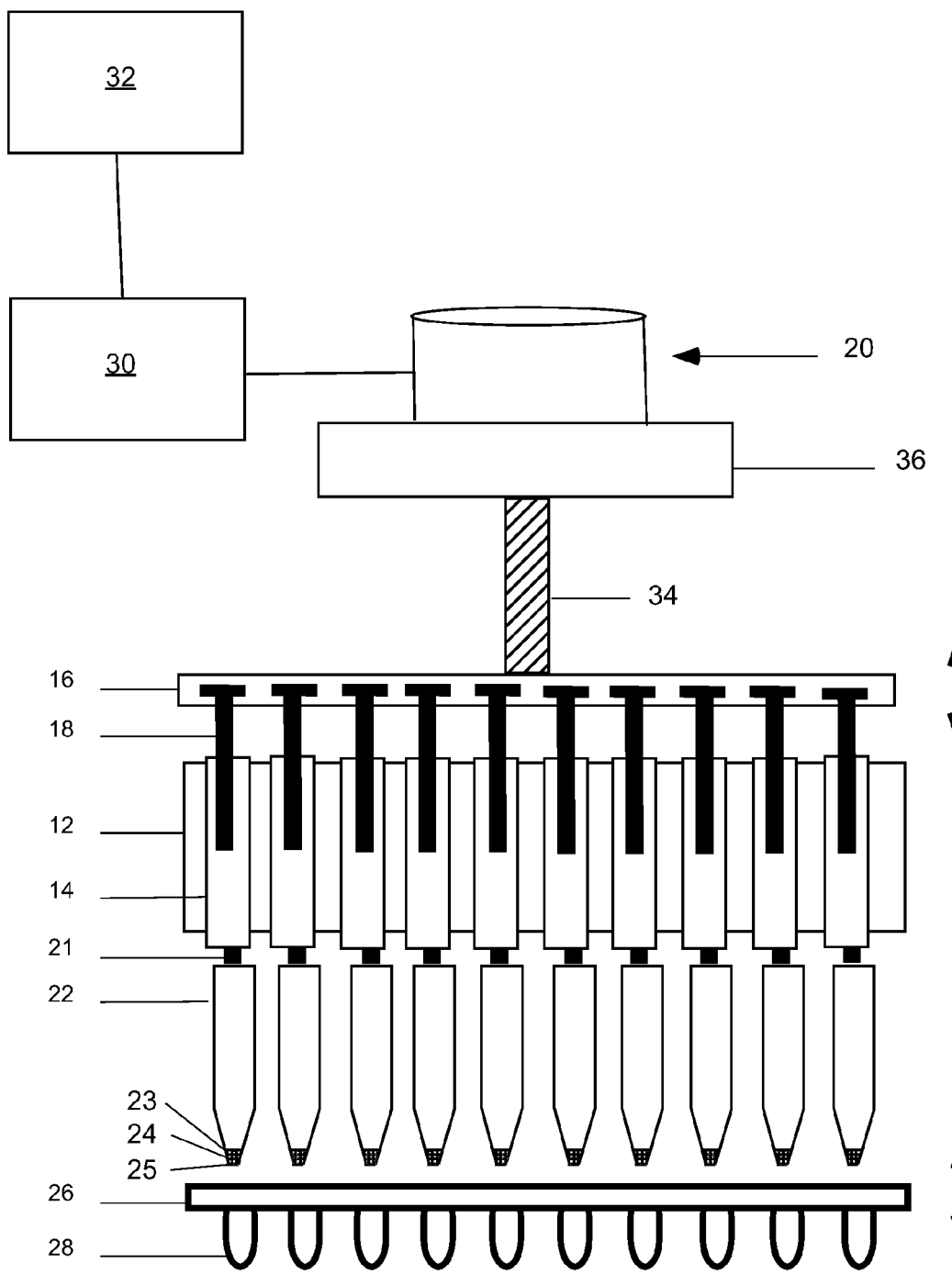
FIG. 13 depicts an example of a multiplexed extraction apparatus.

FIG. 13 depicts an example of a multiplexed extraction system. The system includes a syringe holder 12 for holding a series of syringes 14 (e.g., 1 mL glass syringes) and a plunger holder 16 for engaging the plungers 18 with a syringe pump 20. The syringe pump includes a screw 34 to move the plunger holder and a stationary base 36. The syringe pump can move the plunger holder up and down while the syringe holder remains stationary, thus simultaneously actuating all syringe plungers attached to the holder. Each syringe includes an attachment fitting 21 for attachment of an extraction column. Attached to each syringe via the fitting is an extraction column 22. The column depicted in this embodiment employs a modified pipet tip for the column body, membrane filters serve as the upper and lower frits 23 and 25, and the bed of extraction media 24 is a packed bed of a gel media. The system also includes a sample rack 26 with multiple positions for holding sample collection vials 28, which can be Eppendorf tubes. The sample rack is slidably mounted on two vertical rods, and the height of the rack can be adjusted by sliding it up or down the rods and locking the rack at the desired location. The position of the rack can be adjusted to bring the lower end (the tip) of the column into contact with solution in a tube in the Eppendorf rack. The system also includes a controller 30 for controlling the syringe pump. The controller is attached to a computer 32, which can be programmed to control the movement of the pump through the controller. The controller allows for control of when and at what rate the plunger rack is moved, which in turn is used to control the flow of solution through the columns, withdrawal and infusion. Control of the plungers can be manual or automated, by means of a script file that can be created by a user. The software allows for control of the flow rate through the columns, and an extraction protocol can include multiple withdraw and infusion cycles, along with optional delays between cycles.

In one example of a multiplexing procedure, 10 Eppendorf tubes containing a sample, e.g., 500 µL of a clarified cell lysate containing a his-tagged recombinant protein, are placed in the sample rack. One mL syringes are attached to the syringe holder, and the plungers are engaged with the plunger holder. Extraction columns, e.g., low dead volume packed bed columns as elsewhere herein, are affixed to the syringe attachment fittings. The tip is conditioned by ejecting the bulk of the storage solution from the column and replacing it with air. The sample rack is raised so that the ends of the extraction tips enter the sample. Sample solution is drawn into the columns by action of the syringe pump, which raises the plunger holder and plungers. The pump is preferably capable of precisely drawing up a desired volume of solution at a desired flow rate, and of pushing and pulling solution through the column. An example of a suitable syringe pump is the ME-100 (available from PhyNexus, Inc., San Jose, Calif.). Control of the solvent liquid in the column is optionally bidirectional. In this case, and where a syringe is used to control the liquid, the syringe plunger head and the syringe body should be tightly held within the syringe pump. When the syringe plunger direction is reversed, then there can be a delay or a hysteresis effect before the syringe can begin to move the liquid in the opposite direction. This effect becomes more important as the volume solvent is decreased. In the ME-100 instrument, the syringe and syringe plunger are secured so that no discernable movement can be made against the holder rack.

If the sample volume is larger than the interstitial volume of the bed, sample is drawn through the bed and into the column body above the upper frit. The sample solution is then expelled back into the sample container. In some embodiments, the process of drawing sample through the bed and back out into the sample container is performed two or more times, each of which results in the passage of the sample through the bed twice. As discussed elsewhere herein, analyte adsorption can in some cases be improved by using a slower flow rate and/or by increasing the number of passages of sample through the extraction media.

The sample container is then removed and replaced with a similar container holding wash solution (e.g., in the case of an immobilized metal extraction, 5 mM imidazole in PBS), and the wash solution is pumped back and forth through the extraction bed (as was the case with the sample). The wash step can be repeated one or more times with additional volumes of wash solution. A series of two or more different wash solutions can optionally be employed, e.g., PBS followed by water.

Optionally, the syringe can be changed prior to elution. For example, 1 mL disposable syringes used for sample and wash solution can be replaced with 50 µL GasTight syringes for the elution. The original sample rack (or a different sample collection tray) is then filled with sample collection vials (e.g., 0.5 mL Eppendorf tubes), and the height of the tubes adjusted so that the lower ends of the columns are just above the bottom of the individual samples tubes. An aliquot of desorption solvent is placed at the bottom of each tube (e.g., 15 µL of 200 mM imidazole would be typical for elution of protein off an immobilized metal column having a bed volume of about 20 µL). The elution solution can be manipulated back and forth through the bed multiple times by repeated cycles of aspirating and expelling the solution through the column. The elution cycle is completed by ejecting the desorption solution back into the sample vial. The elution process can be repeated, in some cases allowing for improved sample recovery.

The above-described extraction process can be automated, for example by using software to program the computer controller to control the pumping, e.g., the volumes, flow rates, delays, and number of cycles.

In some embodiments, the invention provides a multiplexed extraction system comprising a plurality of extraction columns of the invention, e.g., low dead volume pipet tip columns having small beds of packed gel resins. The system can be automated or manually operated. The system can include a pump or pump in operative engagement with the extraction columns, useful for pumping fluid through the columns in a multiplex fashion, i.e., concurrently. In some embodiments, each column is addressable. The term "addressable" refers to the ability of the fluid manipulation mechanism, e.g., the pumps, to individually address each column. An addressable column is one in which the flow of fluid through the column can be controlled independently from the flow through any other column which may be operated in parallel. In practice, this means that the pumping means in at least one of the extraction steps is in contact and control of each individual column independent of all the other columns. For example, when syringe pumps are used, i.e., pumps capable of manipulating fluid within the column by the application of positive or negative pressure, then separate syringes are used at each column, as opposed to a single vacuum attached to multiple syringes. Because the columns are addressable, a controlled amount of liquid can be accurately manipulated in each column. In a non-addressable system, such as where a single pump is applied to multiple columns, the liquid handling can be less precise. For example, if the back pressure differs between multiplexed columns, then the amount of liquid entering each column and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The invention also provides software for implementing the methods of the invention. For example, the software can be programmed to control manipulation of solutions and addressing of columns into sample vials, collection vials, for spotting or introduction into some analytical device for further processing.

The invention also includes kits comprising one or more reagents and/or articles for use in a process relating to solid-phase extraction, e.g., buffers, standards, solutions, columns, sample containers, etc.

Step and Multi-dimensional Elutions

In some embodiments of the invention, desorption solvent gradients, step elutions and/or multidimensional elutions are performed.

The use of gradients is well known in the art of chromatography, and is described in detail, for example in a number of the general chromatography references cited herein. As applied to the extraction columns of the invention, the basic principle involves adsorbing an analyte to the extraction media and then eluting with a desorption solvent gradient. The gradient refers to the changing of at least one characteristic of the solvent, e.g., change in pH, ionic strength, polarity, or the concentration of some agent that influence the strength of the binding interaction. The gradient can be with respect to the concentration of a chemical that entity that interferes with or stabilizes an interaction, particularly a specific binding interaction. For example, where the affinity binding agent is an immobilized metal the gradient can be in the concentration of imidazole, EDTA, etc. In some embodiments, the result is fractionation of a sample, useful in contexts such as gel-free shotgun proteomics.

As used herein, the term "dimension" refers to some property of the desorption solvent that is varied, e.g., pH, ionic strength, etc. An elution scheme that involves variation of two or more dimensions, either simultaneously or sequentially, is referred to as a multi-dimensional elution.

Gradients used in the context of the invention can be step elutions. In one embodiment, two or more elution steps are performed using different desorption solvents (i.e., elution solvents) that vary in one or more dimensions. For example, the two or more solvents can vary in pH, ionic strength, hydrophobicity, or the like. The volume of desorption solution used in each dimension can be quite small, and can be passed back and forth through the bed of extraction media multiple times and at a rate that is conducive to maximal recovery of desired analyte.

In some embodiments of the invention a multidimensional stepwise solid phase extraction is employed. This is particularly useful in the analysis of isotope-coded affinity tagged (ICAT) peptides, as described in U.S. patent application Ser. No. 10/434,713 and references cited therein. A multi-dimensional extraction involves varying at least two desorption condition dimensions.

In a typical example, a stepwise elution is performed in one dimension, collecting fractions for each change in elution conditions. For example, a stepwise increase in ionic strength could be employed where the extraction phase is based on ion exchange. The eluted fractions are then introduced into a second extraction column (either directly or after collection into an intermediate holding vessel) and in this case separated in another dimension, e.g., by reverse-phase, or by binding to an affinity binding group such as avidin or immobilized metal.

In some embodiments, one or more dimensions of a multidimensional extraction are achieved by means other than an extraction column of the invention. For example, the first dimension separation might be accomplished using conventional chromatography, electrophoresis, or the like, and the fractions then loaded on an extraction column for separation in another dimension.

Note that in many cases the elution of a protein will not be a simple on-off process. That is, some desorption buffers will result in only partial release of analyte. The composition of the desorption buffer can be optimized for the desired outcome, e.g., complete or near complete elution. Alternatively, when step elution is employed two or more successive steps in the elution might result in incremental elution of fraction of an analyte. These incremental partial elution can be useful in characterizing the analyte, e.g., in the analysis of a multi-protein complex as described below.

Purification of Classes of Proteins

Extraction columns can be used to purify entire classes of proteins on the basis of highly conserved motifs within their structure, whereby an affinity binding agent is used that reversibly binds to the conserved motif. For example, it is possible to immobilize particular nucleotides on the extraction media. These nucleotides include adenosine 5'-triphosphate (ATP), adenosine 5'-diphosphate (ADP), adenosine 5'-monophosphate (AMP), nicotinamide adenine dinucleotide (NAD), or nicotinamide adenine dinucleotide phosphate (NADP). These nucleotides can be used for the purification of enzymes that are dependent upon these nucleotides such as kinases, phosphatases, heat shock proteins and dehydrogenases, to name a few.

There are other affinity groups that can be immobilized on the extraction media for purification of protein classes. Lectins can be employed for the purification of glycoproteins. Concanavalin A (Con A) and lentil lectin can be immobilized for the purification of glycoproteins and membrane proteins, and wheat germ lectin can be used for the purification of glycoproteins and cells (especially T-cell lymphocytes). Though it is not a lectin, the small molecule phenylboronic acid can also be immobilized and used for purification of glycoproteins.

It is also possible to immobilize heparin, which is useful for the purification of DNA-binding proteins (e.g. RNA polymerase I, II and III, DNA polymerase, DNA ligase). In addition, immobilized heparin can be used for purification of various coagulation proteins (e.g. antithrombin III, Factor VII, Factor IX, Factor XI, Factor XII and XIIa, thrombin), other plasma proteins (e.g. properdin, BetaIH, Fibronectin, Lipases), lipoproteins (e.g. VLDL, LDL, VLDL apoprotein, HOLP, to name a few), and other proteins (platelet factor 4, hepatitis B surface antigen, hyaluronidase). These types of proteins are often blood and/or plasma borne. Since there are many efforts underway to rapidly profile the levels of these types of proteins by technologies such as protein chips, the performance of these chips will be enhanced by performing an initial purification and enrichment of the targets prior to protein chip analysis.

It is also possible to attach protein interaction domains to extraction media for purification of those proteins that are meant to interact with that domain. One interaction domain that can be immobilized on the extraction media is the Src-homology 2 (SH2) domain that binds to specific phosphotyrosine-containing peptide motifs within various proteins. The SH2 domain has previously been immobilized on a resin and used as an affinity reagent for performing affinity chromatography/mass spectrometry experiments for investigating in vitro phosphorylation of epidermal growth factor receptor (EGFR) (see Christian Lombardo, et al., Biochemistry, 34:16456 (1995)). Other than the SH2 domain, other protein interaction domains can be immobilized for the purposes of purifying those proteins that possess their recognition domains. Many of these protein interaction domains have been described (see Tony Pawson, Protein Interaction Domains, Cell Signaling Technology Catalog, 264-279 (2002)) for additional examples of these protein interaction domains).

As another class-specific affinity ligand, benzamidine can be immobilized on the extraction media for purification of serine proteases. The dye ligand Procion Red HE-3B can be immobilized for the purification of dehydrogenases, reductases and interferon, to name a few.

In another example, synthetic peptides, peptide analogs and/or peptide derivatives can be used to purify proteins, classes of proteins and other biomolecules that specifically recognize peptides. For example, certain classes of proteases recognize specific sequences, and classes of proteases can be purified based on their recognition of a particular peptide-based affinity binding agent.

Multi-protein Complexes

In certain embodiments, extraction columns of the invention are used to extract and/or process multi-protein complexes. This is accomplished typically by employing a sample solution that is sufficiently non-denaturing that it does not result in disruption of a protein complex or complexes of interest, i.e., the complex is extracted from a biological sample using a sample solution and extraction conditions that stabilize the association between the constituents of the complex. As used herein, the term multi-protein complex refers to a complex of two or more proteins held together by mutually attractive chemical forces, typically non-covalent interactions. Covalent attachments would typically be reversible, thus allowing for recovery of component proteins.

In some embodiments, multi-protein complex is adsorbed to the extraction surface and desorbed under conditions such that the integrity of the complex is retained throughout. That is, the product of the extraction is the intact complex, which can then be collected and stored, or directly analyzed (either as a complex or a mixture of proteins), for example by any of the analytical methodologies described herein.

One example involves the use of a recombinant "bait" protein that will form complexes with its natural interaction partners. These multiprotein complexes are then purified through a fusion tag that is attached to the "bait." These tagged "bait" proteins can be purified through affinity reagents such as metal-chelate groups, antibodies, calmodulin, or any of the other surface groups employed for the purification of recombinant proteins. The identity of the cognate proteins can then be determined by any of a variety of means, such as MS.

It is also possible to purify "native" (i.e. non-recombinant) protein complexes without having to purify through a fusion tag. For example, this can be achieved by using as an affinity binding reagent an antibody for one of the proteins within the multiprotein complex. This process is often referred to as "co-immunoprecipitation." The multiprotein complexes can be eluted, for example, by means of low pH buffer.

In some embodiments, the multi-protein complex is loaded onto the column as a complex, and the entire complex or one or more constituents are desorbed and eluted. In other embodiments, one or more complex constituents are first adsorbed to the extraction surface, and subsequently one or more other constituents are applied to the extraction surface, such that complex formation occurs on the extraction surface.

In another embodiment, the extraction columns of the invention can be used as a tool to analyze the nature of the complex. For example, the protein complex is desorbed to the extraction surface, and the state of the complex is then monitored as a function of solvent variation. A desorption solvent, or series of desorption solvents, can be employed that result in disruption of some or all of the interactions holding the complex together, whereby some subset of the complex is released while the rest remains adsorbed. The identity and state (e.g., post-translational modifications) of the proteins released can be determined often, using, for example, MS. Thus, in this manner constituents and/or sub-complexes of a protein complex can be individually eluted and analyzed. The nature of the desorption solvent can be adjusted to favor or disfavor interactions that hold protein complexes together, e.g., hydrogen bonds, ionic bonds, hydrophobic interactions, van der Waals forces, and covalent interactions, e.g., disulfide bridges. For example, by decreasing the polarity of a desorption solvent hydrophobic interactions will be weakened-inclusion of reducing agent (such as mercaptoethanol or dithiothrietol) will disrupt disulfide bridges. Other solution variations would include alteration of pH, change in ionic strength, and/or the inclusion of a constituent that specifically or non-specifically affects protein-protein interactions, or the interaction of a protein or protein complex with a non-protein biomolecule.

In one embodiment, a series of two or more desorption solvents is used sequentially, and the eluent is monitored to determine which protein constituents come off at a particular solvent. In this way it is possible to assess the strength and nature of interactions in the complex. For example, if a series of desorption solvents of increasing strength is used (e.g., increasing ionic strength, decreasing polarity, changing pH, change in ionic composition, etc.), then the more loosely bound proteins or sub-complexes will elute first, with more tightly bound complexes eluting only as the strength of the desorption solvent is increased.

In some embodiments, at least one of the desorption solutions used contains an agent that effects ionic interactions. The agent can be a molecule that participates in a specific interaction between two or more protein constituents of a multi-protein complex, e.g., Mg-ATP promotes the interaction and mutual binding of certain protein cognates. Other agents that can affect protein interactions are denaturants such as urea, guanidinium chloride, and isothiocyanate, detergents such as triton X-100, chelating groups such as EDTA, etc.

In other sets of experiments, the integrity of a protein complex can be probed through modifications (e.g., post-translational or mutations) in one or more of the proteins. Using the methods described herein the effect of the modification upon the stability or other properties of the complex can be determined.

In some embodiments of the invention, multidimensional solid phase extraction techniques, as described in more detail elsewhere herein, are employed to analyze multiprotein complexes.

Recovery of Native Proteins

In some embodiments, the extraction devices and methods of the invention are used to purify proteins that are functional, active and/or in their native state, i.e., non-denatured. This is accomplished by performing the extraction process under non-denaturing conditions. Non-denaturing conditions encompasses the entire protein extraction process, including the sample solution, the wash solution (if used), the desorption solution, the extraction phase, and the conditions under which the extraction is accomplished. General parameters that influence protein stability are well known in the art, and include temperature (usually lower temperatures are preferred), pH, ionic strength, the use of reducing agents, surfactants, elimination of protease activity, protection from physical shearing or disruption, radiation, etc. The particular conditions most suited for a particular protein, class of proteins, or protein-containing composition vary somewhat from protein to protein.

One particular aspect of the extraction technology of the invention that facilitates non-denaturing extraction is that the process can be accomplished at low temperatures. In particular, because solution flow through the column can be done without introducing heat, e.g., without the introduction of electrical current or the generation of joule heat that typically accompanies capillary processes involving chromatography or electro-osmotic flow, the process can be carried out at lower temperatures. Lower temperature could be room temperature, or even lower, e.g., if the process is carried out in a cold room, or a cooling apparatus is used to cool the capillary. For example, extractions can be performed at a temperature as low as 0° C., 2° C. or 4° C., e.g., in a range such as 0° C. to 30° C., 0° C. to 20° C., 2° C. to 30° C., 2° C. to 20° C., 4° C. to 30° C., or 4° C. to 20° C.

Another aspect of extraction as described herein that allows for purification of native proteins is that the extraction process can be completed quickly, thus permitting rapid separation of a protein from proteases or other denaturing agents present in sample solution. The speed of the process allows for quickly getting the protein from the sample solution to the analytical device for which it is intended, or to storage conditions that promote stability of the protein. In various embodiments of the invention, protein extractions of the invention can be accomplished in less than 1 minute, less than 2 minutes, less than 5 minutes, less than 10 minutes, less than 15 minutes, less than 20 minutes, less than 60 minutes, or less than 120 minutes.

In another embodiment, the extraction process is performed under conditions that do not irreversibly denature the protein. Thus, even if the protein is eluted in a denatured state, the protein can be renatured to recover native and/or functional protein. In this embodiment, the protein is adsorbed to the extraction surface under conditions that do not irreversibly denature the protein, and eluting the protein under conditions that do not irreversibly denature the protein. The conditions required to prevent irreversible denaturation are similar to those that are non-denaturing, but in some cases the requirements are not as stringent. For example, the presence of a denaturant such as urea, isothiocyanate or guanidinium chloride can cause reversible denaturation. The eluted protein is denatured, but native protein can be recovered using techniques known in the art, such as dialysis to remove denaturant. Likewise, certain pH conditions or ionic conditions can result in reversible denaturation, readily reversed by altering the pH or buffer composition of the eluted protein.

The recovery of non-denatured, native, functional and/or active protein is particularly useful as a preparative step for use in processes that require the protein to be non-denatured in order for the process to be successful. Non-limiting examples of such processes include analytical methods such as binding studies, activity assays, enzyme assays, X-ray crystallography and NMR.

In another embodiment, the invention is used to stabilize RNA. This can be accomplished by separating the RNA from some or substantially all RNase activity, enzymatic or otherwise, that might be present in a sample solution. In one example, the RNA itself is extracted and thereby separated from RNase in the sample. In another example, the RNase activity is extracted from a solution, with stabilized RNA flowing through the column. Extraction of RNA can be sequence specific or non-sequence specific. Extraction of RNase activity can be specific for a particular RNase or class of RNAses, or can be general, e.g., extraction of proteins or subset of proteins.

Extraction Tube as Sample Transfer Medium

In certain embodiments, an extraction column can function not only as a separation device, but also as a means for collecting, transporting, storing and or dispensing a liquid sample.

For example, in one embodiment the extraction column is transportable, and can be readily transported from one location to another. Note that this concept of transportability refers to the extraction devices that can be easily transported, either manually or by an automated mechanism (e.g., robotics), during the extraction process. This is to be distinguished from other systems that employ a column in a manner such that it is stably connected to a device that is not readily portable, e.g, n HPLC instrument. While one can certainly move such an instrument, for example when installing it in a laboratory, during use the column remains stably attached to the stationary instrument. In contrast, in certain embodiments of the invention the column is transported.

In another embodiment, an extraction column is transportable to the site where the eluted sample is destined, e.g., a storage vessel or an analytical instrument. For example, the column, with analyte bound, can be transported to an analytical instrument, to a chip, an arrayer, etc, and eluted directly into or onto the intended target. In one embodiment, the column is transported to an electrospray ionization chamber and eluted directly therein. In another embodiment, the column is transported to a chip or MALDI target and the analyte spotted directly on the target.

In some embodiments of the invention involving transportable column or column devices, the entire column is transported, e.g., on the end of a syringe, or just the bare column or a portion thereof.

Thus, in various embodiments the invention provides a transportable extraction device, which includes the extraction column and optionally other associated components, e.g., pump, holder, etc. The term "transportable" refers to the ability of an operator of the extraction to transport the column, either manually or by automated means, during the extraction process, e.g., during sample uptake, washing, or elution, or between any of these steps. This is to be distinguished from non-transportable extraction devices, such as an extraction column connected to a stationary instrument, such that the column is not transported, nor is it convenient to transport the column, during normal operation.

Method for Desalting a Sample

In some embodiments, the invention is used to change the composition of a solution in which an analyte is present. An example is the desalting of a sample, where some or substantially all of the salt (or other constituent) in a sample is removed or replaced by a different salt (or non-salt constituent). The removal of potentially interfering salt from a sample prior to analysis is important in a number of analytical techniques, e.g., mass spectroscopy. These processes will be generally referred to herein as "desalting," with the understanding that the term can encompass any of a wide variety of processes involving alteration of the solvent or solution in which an analyte is present, e.g., buffer exchange or ion replacement.

In some embodiments, desalting is accomplished by extraction of the analyte, removal of salt, and desorption into the desired final solution. For example, the analyte can be adsorbed in a reverse phase, ion pairing or hydrophobic interaction extraction process. In some embodiments, the process will involve use of a hydrophobic interaction extraction phase, e.g., benzyl or a reverse extraction phase, e.g., C8, C18 or polymeric. There are numerous other possibilities; e.g., virtually any type of reverse phase found on a conventional chromatography packing particle can be employed.

An anion exchanger can be used to adsorb an analyte, such as a protein at a pH above its isoelectric point. Desorption can be facilitated by eluting at a pH below the isoelectric point, but this is not required, e.g., elution can be accomplished by displacement using a salt or buffer Likewise, a cation exchanger can be used to adsorb protein at a pH below its isoelectric point, or a similar analyte.

Analytical Techniques

Extraction columns and associated methods of the invention find particular utility in preparing samples of analyte for analysis or detection by a variety of analytical techniques. In particular, the methods are useful for purifying an analyte, class of analytes, aggregate of analytes, etc, from a biological sample, e.g., a biomolecule originating in a biological fluid. It is particularly useful for use with techniques that require small volumes of pure, concentrated analyte. In many cases, the results of these forms of analysis are improved by increasing analyte concentration. In some embodiments of the invention the analyte of interest is a protein, and the extraction serves to purify and concentrate the protein prior to analysis. The methods are particular suited for use with label-free detection methods or methods that require functional, native (i.e., non-denatured protein), but are generally useful for any protein or nucleic acid of interest.

These methods are particularly suited for application to proteomic studies, the study of protein-protein interactions, and the like. The elucidation of protein-protein interaction networks, preferably in conjunction with other types of data, allows assignment of cellular functions to novel proteins and derivation of new biological pathways. See, e.g., Curr. Protein Pept. Sci. 2003 4(3):159-81.

Many of the current detection and analytical methodologies can be applied to very small sample volumes, but often require that the analyte be enriched and purified in order to achieve acceptable results. Conventional sample preparation technologies typically operate on a larger scale, resulting in waste because they produce more volume than is required. This is particularly a problem where the amount of starting sample is limited, as is the case with many biomolecules. These conventional methods are generally not suited for working with the small volumes required for these new methodologies. For example, the use of conventional packed bed chromatography techniques tend to require larger solvent volumes, and are not suited to working with such small sample volumes for a number of reasons, e.g., because of loss of sample in dead volumes, on frits, etc. See U.S. patent application Ser. No. 10/434,713 for a more in-depth discussion of problems associated with previous technologies in connection with the enrichment and purification of low abundance biomolecules.

In certain embodiments, the invention involves the direct analysis of analyte eluted from an extraction column without any intervening sample processing step, e.g., concentration, desalting or the like, provided the method is designed correctly. Thus, for example, a sample can be eluted from a column and directly analyzed by MS, SPR or the like. This is a distinct advantage over other sample preparation methods that require concentration, desalting or other processing steps before analysis. These extra steps can increase the time and complexity of the experiment, and can result in significant sample loss, which poses a major problem when working with low abundance analytes and small volumes.

One example of such an analytical technique is mass spectroscopy (MS). In application of mass spectrometry for the analysis of biomolecules, the molecules are transferred from the liquid or solid phases to gas phase and to vacuum phase. Since many biomolecules are both large and fragile (proteins being a prime example), two of the most effective methods for their transfer to the vacuum phase are matrix-assisted laser desorption ionization (MALDI) or electrospray ionization (ESI). Some aspects of the use of these methods, and sample preparation requirements, are discussed in more detail in U.S. patent application Ser. No. 10/434,713. In general ESI is more sensitive, while MALDI is faster. Significantly, some peptides ionize better in MALDI mode than ESI, and vice versa (Genome Technology, June 220, p 52). The extraction methods and devices of the instant invention are particularly suited to preparing samples for MS analysis, especially biomolecule samples such as proteins. An important advantage of the invention is that it allows for the preparation of an enriched sample that can be directly analyzed, without the need for intervening process steps, e.g., concentration or desalting.

ESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the column into an electrospray nozzle, e.g., the column functions as the sample loader.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one embodiment, the eluted sample is deposited directly from the column onto the metal target, e.g., the column itself functions as the sample loader. In one embodiment, the extracted analyte is deposited on a MALDI target, a MALDI ionization matrix is added, and the sample is ionized and analyzed, e.g., by TOF detection.

In other embodiments of the invention, extraction is used in conjunction with other forms of MS, e.g., other ionization modes. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt. In the case of MALDI, the analyte should be in a solvent compatible with spotting on the target and with the ionization matrix employed.

In some embodiments, the invention is used to prepare an analyte for use in an analytical method that involves the detection of a binding event on the surface of a solid substrate. These solid substrates are generally referred to herein as "binding detection chips," examples of which include hybridization microarrays and various protein chips. As used herein, the term "protein chip" is defined as a small plate or surface upon which an array of separated, discrete protein samples (or "dots") are to be deposited or have been deposited. In general, a chip bearing an array of discrete ligands (e.g., proteins) is designed to be contacted with a sample having one or more biomolecules which may or may not have the capability of binding to the surface of one or more of the dots, and the occurrence or absence of such binding on each dot is subsequently determined. A reference that describes the general types and functions of protein chips is Gavin MacBeath, Nature Genetics Supplement, 32:526 (2002). See also Ann. Rev. Biochem., 2003 72:783-812.

In general, these methods involve the detection binding between a chip-bound moiety "A" and its cognate binder "B"; i.e, detection of the reaction A+B=AB, where the formation of AB results, either directly or indirectly, in a detectable signal. Note that in this context the term "chip" can refer to any solid substrate upon which A can be immobilized and the binding of B detected, e.g., glass, metal, plastic, ceramic, membrane, etc. In many important applications of chip technology, A and/or B are biomolecules, e.g., DNA in DNA hybridization arrays or protein in protein chips. Also, in many cases the chip comprises an array multiple small, spatially-addressable spots of analyte, allowing for the efficient simultaneous performance of multiple binding experiments on a small scale.

In various embodiments, it can be beneficial to process either A or B, or both, prior to use in a chip experiment, using the extraction columns and related methodologies described herein. In general, the accuracy of chip-based methods depends upon specific detection of the AB interaction. However, in practice binding events other than authentic AB binding can have the appearance of an AB binding event, skewing the results of the analysis. For example, the presence of contaminating non-A species that have some affinity for B, contaminating non-B species having an affinity for A, or a combination of these effects, can result in a binding event that can be mistaken for a true AB binding event, or interfere with the detection of a true AB binding event. These false binding events will throw off any measurement, and in some cases can substantially compromise the ability of the system to accurately quantify the true AB binding event.

Thus, in one embodiment, an extraction column is used to purify a protein for spotting onto a protein chip, with the protein serving as A. In the production of protein chips, it is often desirable to spot the chip with very small volumes of protein, e.g., on the order of 1 µL, 100 nL, 10 nL or even less. Many embodiments of this invention are particularly suited to the efficient production of such small volumes of purified protein. The technology can also be used in a "just-in-time" purification mode, where the chip is spotted just as the protein is being purified.

Examples of protein analytes that can be beneficially processed by the technology described herein include antibodies (e.g., IgG, IgY, etc.); general affinity proteins, (e.g., scFvs, Fabs, affibodies, peptides, etc.); nucleic acids aptamers and photoaptamers as affinity molecules, and other proteins to be screened for undetermined affinity characteristics (e.g., protein libraries from model organisms). The technology is particularly useful when applied to preparation of protein samples for global proteomic analysis, for example in conjunction with the technology of Protometrix Inc. (Branford, Conn.). See, for example, Zhu et al. "Global analysis of protein activities using proteome chips" (2001) Science 293 (5537): 2101-05; Zhu et al., "Analysis of yeast protein kinases using protein chips" (2000) Nature Genetics 26:1-7; and Michaud and Snyder "Proteomic approaches for the global analysis of proteins" (2002) BioTechniques 33:1308-16.

A variety of different approaches can be used to affix A to a chip surface, including direct/passive immobilization (can be covalent in cases of native thiols associating with gold surfaces, covalent attachment to functional groups at a chip surface (e.g., self-assembled monolayers with and without additional groups, immobilized hydrogel, etc.), non-covalent/affinity attachment to functional groups/ligands at a chip surface (e.g., Protein A or Protein G for IgGs, phenyl(di) boronic acid with salicylhydroxamic acid groups, streptavidin monolayers with biotinylated native lysines/cysteines, etc.).

In this and related embodiments, a protein is purified and/or concentrated using an extraction method as described herein, and then spotted at a predetermined location on the chip. In preferred embodiments, the protein is spotted directly from an extraction column onto the substrate. That is, the protein is extracted from a sample solution and then eluted in a desorption solution directly onto the chip. Of course, in this embodiment it is important that the desorption solution be compatible with the substrate and with any chemistry used to immobilize or affix the protein to the substrate. Typically a microarray format involves multiple spots of protein samples (the protein samples can all be the same or they can be different from one another). Multiple protein samples can be spotted sequentially or simultaneously. Simultaneous spotting can be achieved by employing a multiplex format, where an array of extraction columns is used to purify and spot multiple protein samples in parallel. The small size and portability made possible by the use of columns facilitates the direct spotting of freshly purified samples, and also permits multiplexing formats that would not be possible with bulkier conventional protein extraction devices. Particularly when very small volumes are to be spotted, it is desirable to use a pump capable of the accurate and reproducible dispensing of small volumes of liquid, as described elsewhere herein.

In another embodiment, extraction columns of the invention are used to purify B, e.g., a protein, prior to application to a chip. As with A, purified B can be applied directly to the chip, or alternatively, it can be collected from the column and then applied to the chip. The desorption solution used should be selected such that it is compatible with the chip, the chemistry involved in the immobilization of A, and with the binding and/or detection reactions. As with A, the methods of the invention allow for "just-in-time" purification of the B molecule.

A variety of extraction chemistries and approaches can be employed in the purification of A or B. For example, if a major contaminant or contaminants are known and sufficiently well-defined (e.g., albumin, fibrin, etc), an extraction chemistry can be employed that specifically removes such contaminants. Alternatively, A or B can be trapped on the extraction surface, contaminants removed by washing, and then the analyte released for use on the binding chip. This further allows for enrichment of the molecule, enhancing the sensitivity of the AB event.

The detection event requires some manner of A interacting with B, so the central player is B (since it isn't part of the protein chip itself). The means of detecting the presence of B are varied and include label-free detection of B interacting with A (e.g., surface plasmon resonance imaging as practiced by HTS Biosystems (Hopkinton, Mass.) or Biacore, Inc. (Piscataway, N.J.), microcantilever detection schemes as practiced by Protiveris, Inc. (Rockville, Md.) microcalorimetry, acoustic wave sensors, atomic force microscopy, quartz crystal microweighing, and optical waveguide lightmode spectroscopy (OWLS), etc). Alternatively, binding can be detected by physical labeling of B interacting with A, followed by spatial imaging of AB pair (e.g., Cy3/Cy5 differential labeling with standard fluorescent imaging as practiced by BD-Clontech (Palo Alto, Calif.), radioactive ATP labeling of kinase substrates with autoradiography imaging as practiced by Jerini AG (Berlin, Germany), etc), or other suitable imaging techniques.

In the case of fluorescent tagging, one can often achieve higher sensitivity with planar waveguide imaging (as practiced by ZeptoSens (Witterswil, Switzerland)). See, for example, Voros et al. (2003) BioWorld 2-16-17; Duveneck et al. (2002) Analytica Chimica Acta 469: 49-61, Pawlak et al. (2002) Proteomics 2:383-93; Ehrat and Kresbach (2001) Chimia 55:35-39-Weinberger et al. (2000) Pharmacogenomics 395-416; Ehrat and Kresbach (2000) Chimia 54:244-46-Duveneck and Abel (1999) Review on Fluorescence-based Planar Waveguide Biosensors, Proc. SPIE, Vol. 3858: 59-71; Budachetal. (1999) Anal. Chem. 71:3347-3355; Duveneck et al. (1996) A Novel Generation of Luminescence-based Biosensors: Single-Mode Planar Waveguide Sensors, Proc. SPIE, 2928:98-109; and Neuschafer et al. (1996) Planar Waveguides as Efficient Transducers for Bioaffinity Sensors, Proc. SPIE, 2836:221-234.

Binding can also be detected by interaction of AB complex with a third B-specific affinity partner C, where C is capable of generating a signal by being fluorescently tagged, or is tagged with a group that allows a chemical reaction to occur at that location (such as generation of a fluorescent moiety, direct generation of light, etc.). Detection of this AB-C binding event can occur via fluorescent imaging, (as practiced, e.g., by Zyomyx, Inc. (Hayward, Calif.) and SomaLogic Inc. (Boulder, Colo.)), chemiluminescence imaging (as practiced by HTS Biosystems and Hypromatrix Inc (Worcester, Mass.)), fluorescent imaging via waveguide technology, or other suitable detection means.

In other embodiments of the invention, similar methodology is used to extract and spot other non-protein analytes in an array format, e.g., polynucleotides, polysaccharides or natural products. Analogous to the protein chip example above, any of these analytes can be directly spotted on a microarray substrate, thus avoiding the necessity to collect purified sample in some sort of vial or microwell prior to transfer to the substrate. Of course, it is also possible to use the extraction methods of the invention to purify and collect such substrates prior to spotting, particularly if the high recovery and activity to be achieved by direct spotting is not required.

In some embodiments, the technology is used to prepare a sample prior to detection by optical biosensor technology, e.g., the BIND biosensor from SRU Biosystems (Woburn, Mass.). Various modes of this type of label-free detection are described in the following references: B. Cunningham, P. Li, B. Lin, J. Pepper, "Colorimetric resonant reflection as a direct biochemical assay technique," Sensors and Actuators B, Volume 8 1, p. 316-328, Jan. 5, 2002; B. Cunningham, B. Lin, J. Qiu, P. Li, J. Pepper, B. Hugh, "A Plastic Colorimetric Resonant Optical Biosensor for Multiparallel Detection of Label-Free Biochemical Interactions," Sensors & Actuators B, volume 85, number 3, pp 219-226, (November 2002); B. Lin, J. Qiu, J. Gerstemnaier, P. Li, H. Pien, J. Pepper, B. Cunningham, "A Label-Free Optical Technique for Detecting Small Molecule Interactions," Biosensors and Bioelectronics, Vol. 17, No. 9, p. 827-834, September 2002;. Cunningham, J. Qiu, P. Li, B. Lin, "Enhancing the Surface Sensitivity of Colorimetric Resonant Optical Biosensors," Sensors and Actuators B, Vol. 87, No. 2, p. 365-370, December 2002, "Improved Proteomics Technologies," Genetic Engineering News, Volume 22, Number 6, pp 74-75, Mar. 15, 2002; and "A New Method for Label-Free Imaging of Biomolecular Interactions," P. Li, B. Lin, J. Gerstemnaier, and B. T. Cunningham, Accepted July, 2003, Sensors and Actuators B.

In some modes of optical biosensor technology, a colorimetric resonant diffractive grating surface is used as a surface binding platform. A guided mode resonant phenomenon is used to produce an optical structure that, when illuminated with white light, is designed to reflect only a single wavelength. When molecules are attached to the surface, the reflected wavelength (color) is shifted due to the change of the optical path of light that is coupled into the grating. By linking receptor molecules to the grating surface, complementary binding molecules can be detected without the use of any kind of fluorescent probe or particle label. High throughput screening of pharmaceutical compound libraries with protein targets, and microarray screening of protein-protein interactions for proteomics are examples of applications that can be amenable to this approach.

In some embodiments, the invention is used to prepare an analyte for detection by acoustic detection technology such as that being commercialized by Akubio Ltd. (Cambridge, UK). Various modes of this type of label-free detection are described in the following references: M. A. Cooper, "Label-free screening of molecular interactions using acoustic detection," Drug Discovery Today 2002, 6 (12) Suppl.; M. A. Cooper "Acoustic detection of pathogens using rupture event scanning (REVS)," Directions in Science, 2002, 1, 1-2; and M. A. Cooper, F. N. Dultsev, A. Minson, C. Abell, P. Ostanin and D. Klenerman, "Direct and sensitive detection of a human virus by rupture event scanning,"Nature Biotech., 2001, 19, 833-837.

In some embodiments the invention is used to prepare an analyte for detection by atomic force microscopy, scanning force microscopy and/or nanoarray technology such as that being commercialized by BioForce Nanosciences Inc. (Ames, Iowa). See, for example, Limansky, A., Shlyakhtenko, L. S., Schaus, S., Henderson, E. and Lyubchenko, Y. L. (2002) Amino Modified Probes for Atomic Force Microscopy, Probe Microscopy 2(3-4) 227-234; Kang, S-G., Henderson, E. (2002) Identification of Non-telomeric G-4 binding proteins in human, *E. coli*, yeast and *Arabidopsis*. Molecules and Cells 14(3), 404-410; Clark, M. W., Henderson, E., Henderson, W., Kristmundsdottir, A., Lynch, M., Mosher, C. and Nettikadan, S., (2001) Nanotechnology Tools for Functional Proteomics Analysis, J. Am. Biotech. Lab; Kang, S-G., Lee, E., Schaus, S, and Henderson, E. (2001) Monitoring transfected cells without selection agents by using the dual-cassette expression EGFP vectors. Exp. Molec. Med. 33(3) 174-178; Lu, Q. and E. Henderson (2000) Two Tetrahymena G-DNA binding proteins, TGP I and TGP 3, have novel motifs and may play a role in micromiclear division. Nuc. Acids Res. 28(15); Mosher, C., Lynch, M., Nettikadan, S., Henderson, W., Kristmundsdottir, A., Clark, M. C. and Henderson, E., (2000) NanoA.rrays, The Next Generation Molecular Array Format for High Throughput Proteomics, Diagnostics and Drug Discovery JALA, 5(5) 75-78; O'Brien, J. C., Vivian W. Jones, and Marc D. Porter, Curtis L. Mosher and Eric Henderson, (2000) Immunosensing Platforms Using Spontaneously Adsorbed Antibody Fragments on Gold. Analytical Chemistry, 72(4), 703-710; Tseng, H. C., Lu, Q., Henderson, E., and Graves, D. J., (I 999) Rescue of phosphorylated Tau-mediated microtubule formation by a natural osinolyte TMAO. Proc Natl Acad Sci U SA 1999 Aug. 17; 96(17):9503-8; Lynch, M. and Henderson, E. (1999) A reliable preparation method for imaging DNA by AFM. Microscopy Today, 99-9, 10; Mazzola, L. T., Frank, C. W., Fodor, S.

P. A., Lu, Q., Mosher, C., Lartius, R. and Henderson, E. (1999) Discrimination of DNA hybridization using chemical force microscopy. Biophys. J., 76, 2922-2933; Jones, V. W., Kenseth, J. R., Porter, M. D., Mosher, C. L. and Henderson, E. (1998) Microminiaturized immunoassays using Atomic Force Microscopy and compositionally patterned antigen arrays. Analy. Chem., 70 (7), 123 3-124 1; Fritzsche, W. and Henderson, E. (1997) Ribosome substructure investigated by scanning force microscopy and image processing. J. Micros. 189, 50-56; Fritzsche, W. and Henderson, E. (1997) Mapping elasticity of rehydrated metaphase chromosomes by scanning force microscopy. Ultramicroscopy 69 (1997), 191-200; Schaus, S. S, and Henderson, E. (1997) Cell viability and probe-cell membrane interactions of XR1 glial cells imaged by AFM. Biophysical Journal, 73, 1205-1214-W. Fritzsche, J. Symanzik, K. Sokolov, E. Henderson (1997) Methanol induced lateral diffusion of colloidal silver particles on a silanized glass surface—a scanning force microscopy study. Journal of Colloidal and Interface Science, Journal of Colloid and Interface Science 185 (2), 466-472-Fritzsche, W. and Henderson, E. (1997) Chicken erythrocyte nucleosomes have a defined orientation along the linker DNA—a scanning force microscopy study. Scanning 19, 42-47; W. Fritzsche, E. Henderson (1997) Scanning force microscopy reveals ellipsoid shape of chicken erythrocyte nucleosomes. Scanning 19, 42-47; Vesekna, J., Marsh, T., Miller, R., Henderson, E. (1996) Atomic force microscopy reconstruction of G-wire DNA. J. Vac. Sci. Technol. B 14(2), 1413-1417; W. Fritzsche, L. Martin, D. Dobbs, D. Jondle, R. Miller, J. Vesenka, E. Henderson (1996) Reconstruction of Ribosomal Subunits and rDNA Chromatin Imaged by Scanning Force Microscopy. Journal of Vacuum Science and Technology B 14 (2), 1404-1409—Fritzsche, W. and Henderson, E. (1996) Volume determination of human metaphase chromosomes by scanning force microscopy. Scanning Microscopy 10(1); Fritzsche, W., Sokolov, K., Chumanov, G., Cottom, T. M. and Henderson, E. (1996) Ultrastructural characterization of colloidal metal films for bioanalytical applications by SFM. J. Vac. Sci. Technol., A 14 (3) (1996), 1766-1769; Fritzsche, W., Vesenka, J. and Henderson, E. (1995) Scanning force microscopy of chromatin. Scanning Microscopy. 9(3), 729-73 9; Vesenka, J., Mosher, C. Schaus, S. Ambrosio, L. and Henderson, E. (1995) Combining optical and atomic force microscopy for life sciences research. BioTechniques, 19, 240-253; Jondle, D. M., Ambrosio, L., Vesenka, J. and Henderson, E. (1995) Imaging and manipulating chromosomes with the atomic force microscope. Chromosome Res. 3 (4), 23 9-244; Marsh, T. C., J. Vesenka, and E. Henderson. (1995) A new DNA nanostructure imaged by scanning probe microscopy. Nuc. Acids Res., 23(4), 696-700; Martin, L. D., J. P. Vesenka, E. R. Henderson, and D. L. Dobbs. (1995) Visualization of nucleosomal structure in native chromatin by atomic force microscopy. Biochemistry, 34, 4610-4616—Mosher, C., Jondle, D., Ambrosio, L., Vesenka, J. and Henderson, E. (1994) Microdissection and Measurement of Polytene Chromosomes Using the Atomic Force Microscope. Scanning Microscopy, 8(3) 491-497; Vesenka, J., R. Miller, and E. Henderson. (1994) Three-dimensional probe reconstruction for atomic force microscopy. Rev. Sci. Instrum., 65, 1-3— Vesenka, J., Manne, S., Giberson, R., Marsh, T. and Henderson, E. (1993) Colloidal gold particles as an incompressible atomic force microscope imaging standard for assessing the compressibility of biomolecules., Biophys. J., 65, 992-997; Vesenka, J., S. Manne, G. Yang, C. J. Bustamante and E. Henderson. (1993) Humidity effects on atomic force microscopy of gold-labeled DNA on mica. Scan. Mic. 7(3): 781-788; Rubim, J. C., Kim, J-H., Henderson, E. and Cotton, T. M. (1993) Surface enhanced raman scattering and atomic force microscopy of brass electrodes in sulfuric acid solution containing benzotriazole and chloride ion. Applied Spectroscopy 47(1), 80-84; Parpura, V., Haydon, P. G., Sakaguchi, D. S., Henderson, E. (1993) Atomic force microscopy and manipulation of living glial cells. J. Vac. Sci. Technol. A, I 1 (4), 773-775; Shaiu, W-L., Larson, D. D., Vesenka, J. Henderson, E. (1993) Atomic force microscopy of oriented linear DNA molecules labeled with 5 nm gold spheres. Nuc. Acids Res., 21 (1) 99-103; Henderson, E., Sakaguchi, D. S. (1993) Imaging F-Actin in fixed glial cells with a combined optical fluorescence/atomic force microscope. Neurohnage 1, 145-150; Parpura, V. Haydon, P. G. and Henderson, E. (1993) Three-dimensional imaging of neuronal growth cones and glia with the Atomic Force Microscope. J. Cell Sci. 104, 427-432; Henderson, E., Haydon, P. G and Sakaguchi, D. A. (1992) Actin filaments dynamics in living glial cells imaged by atomic force microscopy. Science, 25 7, 1944-1946; Henderson, E. (1992) Atomic force microscopy of conventional and unconventional nucleic acid Structures. J. Microscopy, 167, 77-84—Henderson, E. (1992) Nanodissection of supercoiled plasmid DNA by atomic force microscopy. Nucleic Acids Research, 20 (3) 445-447.

In some embodiments the invention is used to prepare an analyte for detection by a technology involving activity-based protein profiling such as that being commercialized by ActivX, Inc. (La Jolla, Calif.). Various modes of this methodology are described in the following references: Kidd et al. (2001) Biochemistry 40:4005-4015; Adam et al. (2000) Chemistry and Biology 57:1-16; Liu et al. (1999) PNAS 96(26):146940-14699; Cravatt and Sorensen (2000) Curr. Opin. Chem. Biol. 4:663-668; Patricelli et al. (2001) Proteomics 1-1067-71.

In some embodiments the invention is used to prepare an analyte for analysis by a technology involving a kinetic exclusion assay, such as that being commercialized by Sapidyne Instruments Inc. (Boise, Id.). See, e.g., Glass, T. (1995) Biomedical Products 20(9): 122-23; and Ohumura et al. (2001) Analytical Chemistry 73 (14):3 3 92-99.

In some embodiments, the systems and methods of the invention are useful for preparing protein samples for crystallization, particularly for use in X-ray crystallography-based protein structure determination. The invention is particularly suited for preparation of samples for use in connection with high throughput protein crystallization methods. These methods typically require small volumes of relatively concentrated and pure protein, e.g., on the order of 1 µL, per crystallization condition tested. Instrumentation and reagents for performing high throughput crystallization are available, for example, from Hampton Research Corp. (Aliso Viejo, Calif.), RoboDesign International Inc. (Carlsbad, Calif.), Genomic Solutions, Inc. (Ann Arbor, Mich.) and Corning Life Sciences (Kennebunk, Me.). Typically, protein crystallization involves mixing the protein with a mother liquor to form a protein drop, and then monitoring the drop to see if suitable crystals form, e.g., the sitting drop or hanging drop methods. Since the determination of appropriate crystallization conditions is still largely empirical, normally a protein is tested for crystallization under a large number of different conditions, e.g., a number of different candidate mother liquors are used. The protein can be purified by extraction prior to mixture with mother liquor. The sample can be collected in an intermediate holding vessel, from which it is then transferred to a well and mixed with mother liquor. Alternatively, the protein drop can be dispensed directly from the column to a well. The invention is particularly suited for use in a high-throughput mode, where drops of protein sample are introduced into a number of wells, e.g., the wells of a multi-well plate (e.g., 94, 3 84 wells, etc.) such as a CrystalEX 384 plate from Corning (Corning Life Sciences, Kennebunk Me.). The protein drops and/or mother liquors can be dispensed into microwells using a high precision liquid dispensing system such as the Cartesian. Dispensing System Honeybee (Genomic Solutions, Inc., Ann Arbor, Mich.). In high throughput modes it is desirable to automate the process of crystals trial analysis, using for example a high throughput crystal imager such as the RoboMicroscope III (RoboDesign International Inc., Carlsbad, Calif.).

Other analytical techniques particularly suited for use in conjunction with certain embodiments of the invention include surface immobilized assays, immunological assays, various ligand displacement/competition assays, direct genetic tests, biophysical methods, direct force measurements, NMR, electron microscopy (including cryo-EM), microcalorimetry, mass spectroscopy, IR and other methods such as those discussed in the context of binding detection chips, but which can also be used in non-chips contexts.

In one embodiment, an extracted sample is eluted in a deuterated desorption solvent (i.e., $D_2O$, chloroform-d, etc.) for direct analysis by NMR, e.g., an integrated microfluidic-NMR system. For example, a biomolecule analyte is extracted, washed with PBS or a similar reagent, washed with water as needed, and then liquid blown out. The column is then washed with $D_2O$, e.g, one or more small slugs of $D_2O$, so as to replace substantially all of the water in the extraction phase matrix with $D_2O$. The analyte is then eluted with a deuterated desorption solution, e.g., a buffer made up in $D_2O$. Deuterated solvents can be obtained, e.g., from Norell, Inc. (Landisville, N.J.).

In general, it is important to use a desorption solvent that is consistent with the requirements of the analytical method to be employed, e.g., in many cases it is preferable that the pH of the desorption solvent be around neutral, such as for use with some protein chips.

Adjustment and Control of Column Head Pressure

Figure 15:
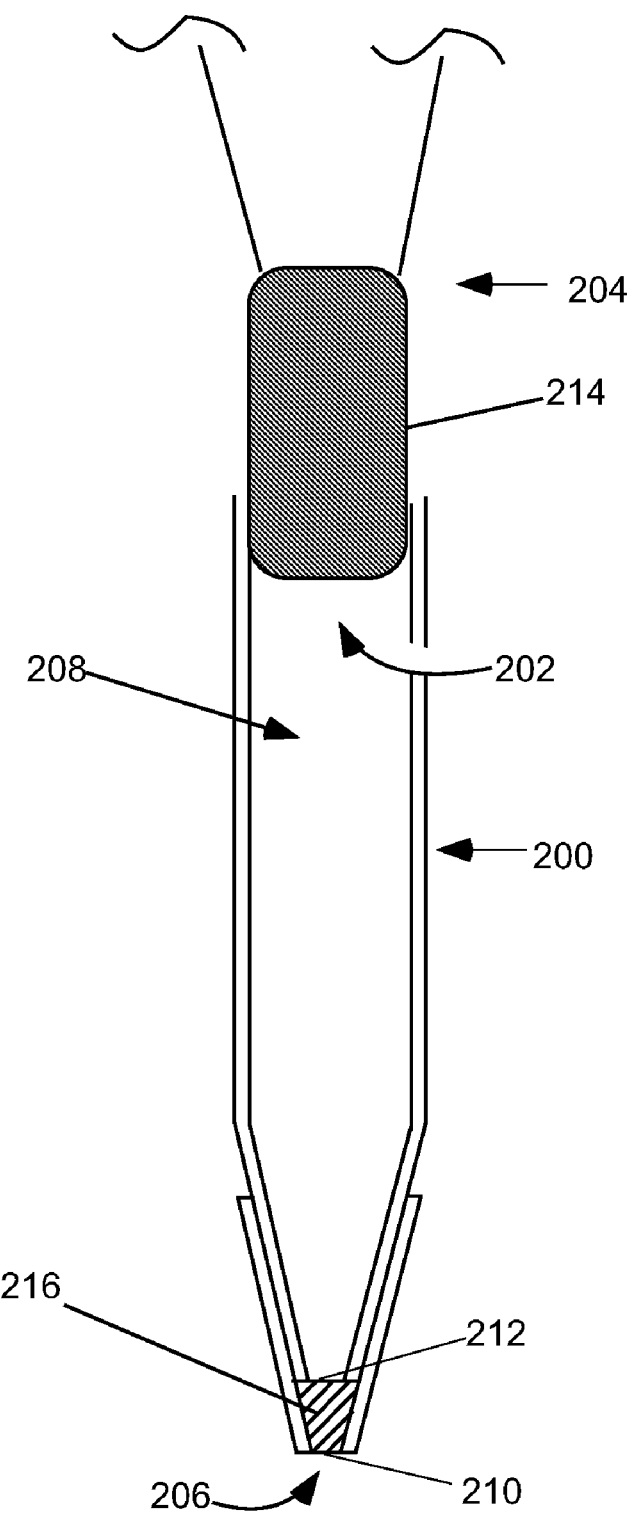
FIG. 15 depicts a pipette tip column attached to a pipettor, and points out the head space.

Various embodiments of the invention employ packed-bed pipette tip columns of the following format, as illustrated in FIG. 15. The columns employ a pipette tip or modified pipette tip as a column body. The column body has an open upper end 202 for communication with a pump 204 (e.g., a pipettor, or a channel of a multi-channel pipettor, attached to the open upper end by a sealing fitting), an open lower end 206 for the uptake and dispensing of fluid, and an open passageway between the upper and lower ends of the column body. A bottom frit 210 is attached to and extends across the open passageway. In the illustration the bottom frit is positioned at the open lower end itself, i.e., at the lower terminus of the column body. While this positioning is preferred in many cases, in alternative embodiments the frit could be attached at a position spanning the open passageway at some distance from the terminus or open lower end. As a result of the positioning and attachment of the frit, substantially any liquid entering or exiting the open passageway via the open lower end will pass through the frit.

The column further includes a top frit 212 that is attached to and extends across the open passageway between the bottom frit 210 and the open upper end 202. The top frit, bottom frit and the surface of the open passageway define a media chamber 216 that contains a packed bed of media, e.g., a packed bed of extraction media having an affinity for an analyte of interest. The column further includes a head space 208, defined as the section of the open passageway between the upper open end and the pump fitting 214. In a typical embodiment of the invention, the volume of the head space is substantially greater than the volume of the media chamber. The head space is open and can accommodate liquid and/or gas that enters through the open lower end and media chamber.

The passage of fluid through the bed of extraction media is controlled by means of the pump 204. The pump is sealing attached to the open upper 202, i.e., a seal is formed between the pump fitting 214 and the open upper end, such that the pump is able to pump gas into or out of the head space, thereby affecting the pressure in the head space, i.e., the head pressure. In alternate embodiments, the attachment of the open upper end to the pump can be direct or indirect, e.g., the attachment can be through valves, fittings, hoses, etc., so long as the attachment is operative and actuation of the pump affects the head pressure, thereby causing fluid to be drawn into or expelled from the bed of media.

In some embodiments of the invention, the column and pump combination illustrated in FIG. 15 is used to pass a liquid back and forth through the packed bed of media. The open lower end is brought into contact with the liquid, and the pump is actuated to draw the liquid into the lower open end and through the packed bed of media, i.e., by generation of a negative pressure in the head space relative to the ambient pressure. In many embodiments, the volume of liquid is substantially greater than the interstitial volume of the bed of extraction media. The liquid passes through the bed and accumulates in the head space. The pump is then actuated to expel all or some of the liquid through the bed of media and out the open lower end, i.e., by generation of a positive pressure in the head space relative to the ambient pressure, e.g., atmospheric pressure. This process is typically repeated multiple times with a plurality of different liquids, e.g. a sample solution containing an analyte of interest, wash solution(s), and desorption solution, in any of the various processes described herein.

The term "ambient pressure" refers to the air pressure outside the column, normally atmospheric air pressure, or the pressure of liquid in contact with the open lower end to be pumped through the media. During the process of pumping liquid through the bed of media, the head pressure will at times differ from the ambient pressure. This occurs because the sealing attachment to the pump at the upper open end and the bed of extraction media and frits at the lower open end impede the flow of gas into and out of the head space. This is particularly the case when the interstitial space of the bed of media is filled with liquid and/or when the frit is wet.

For example, in order to draw a liquid through the lower frit and into the bed of extraction media the pump is used to draw air from the head space, thereby generating a relative negative head pressure. Once the head pressure becomes sufficiently negative relative to the ambient pressure, liquid will be drawn up through the open upper end. Liquid flow is resisted by the backpressure of the column and by surface tension effects within the column, particularly in the bed and at the interface of the bed and frits. Surface tension can arise from the interaction of liquid with the packed bed of media and/or with the frit. This surface tension results in an initial resistance to flow of liquid through the bed of extraction media, described elsewhere herein as a form of "bubble point." As a result, a certain minimum threshold of negative head pressure must be generated before liquid will commence flowing through the bed. In addition, there is the backpressure of the column that must be overcome in order for liquid to flow through the bed. Thus, in operation of the column a sufficiently negative head pressure must be generated to overcome backpressure and surface tension effects prior to flow commencing through the bed. As a result, significant negative head pressures can develop and be maintained; the magnitude of the head pressure will to some extent depend upon the backpressure and surface tension, which in turn depends upon the size of the bed, the nature of the media, the nature of the packing, the nature of the frits, and the interaction of the frits with the bed.

Likewise, a relatively positive head pressure is generated in order to expel liquid from the column. Expulsion of liquid from the column is resisted by the same backpressure and surface tension effects described for liquid uptake. As a result, relatively large positive head pressures can be generated and maintained by the sealing attachment at the upper open end and the resistance to gas flow provided by the bed and frits.

During the course of performing a purification using the columns of the invention, the head pressure of any given column will vary during the course of the process. For example, let us consider an embodiment where multiple pipette tip columns and a programmable multi-channel pipettor are used. The columns are frictionally attached to fittings on the pipettor, which can result in an initial positive pressure in the head space. This positive pressure is the result of compression of the head space as the column is pushed further onto the fitting after forming a seal between the upper open end and the fitting. This positive pressure can be maintained for a substantial period of time, since the seal and the backpressure and surface tension of the bed inhibit the exit of gas from the head space.

In order to draw liquid into the bed, the pump is used draw gas from the head space, thereby generating a head pressure sufficiently negative to overcome backpressure and surface tension effects. This will generate a relatively stable negative pressure. To expel the liquid, the pump is used to force gas into the head space, thereby generating a head pressure sufficiently positive to overcome backpressure and surface tension effects. This process is repeated through each cycle of drawing and expelling liquid from the column, and the process is accompanied by a cycle of negative and positive head pressures.

Note that the head pressure at the beginning of each pumping step is generally not neutral or ambient pressure, but is instead a negative or positive pressure resulting from a prior pumping step, or from the attachment of the tip to the pipettor, or the like. For example, consider a typical purification procedure that involves passing an analyte-containing solution through an extraction bed, followed by a wash and finally a desorption step. At the outset of the desorption step, there will generally be a non-neutral pressure, e.g., a positive head pressure residual from the last step of expelling wash solution. The magnitude of this positive head pressure is the cumulative result of all the previous steps, and will depend to some extent upon the nature of the particular tip column. For example, the greater the resistance to flow that must be overcome by the pump (i.e., the backpressure and surface tension of the particular column), the greater the positive pressure that must be generated in the head space to expel liquid from the column. In order to draw desorption liquid into the bed, the pump must draw enough gas from the head space to compensate for the positive pressure and create a negative head pressure sufficient to draw the desired amount of desorption solution through the bed.

Figure 16:
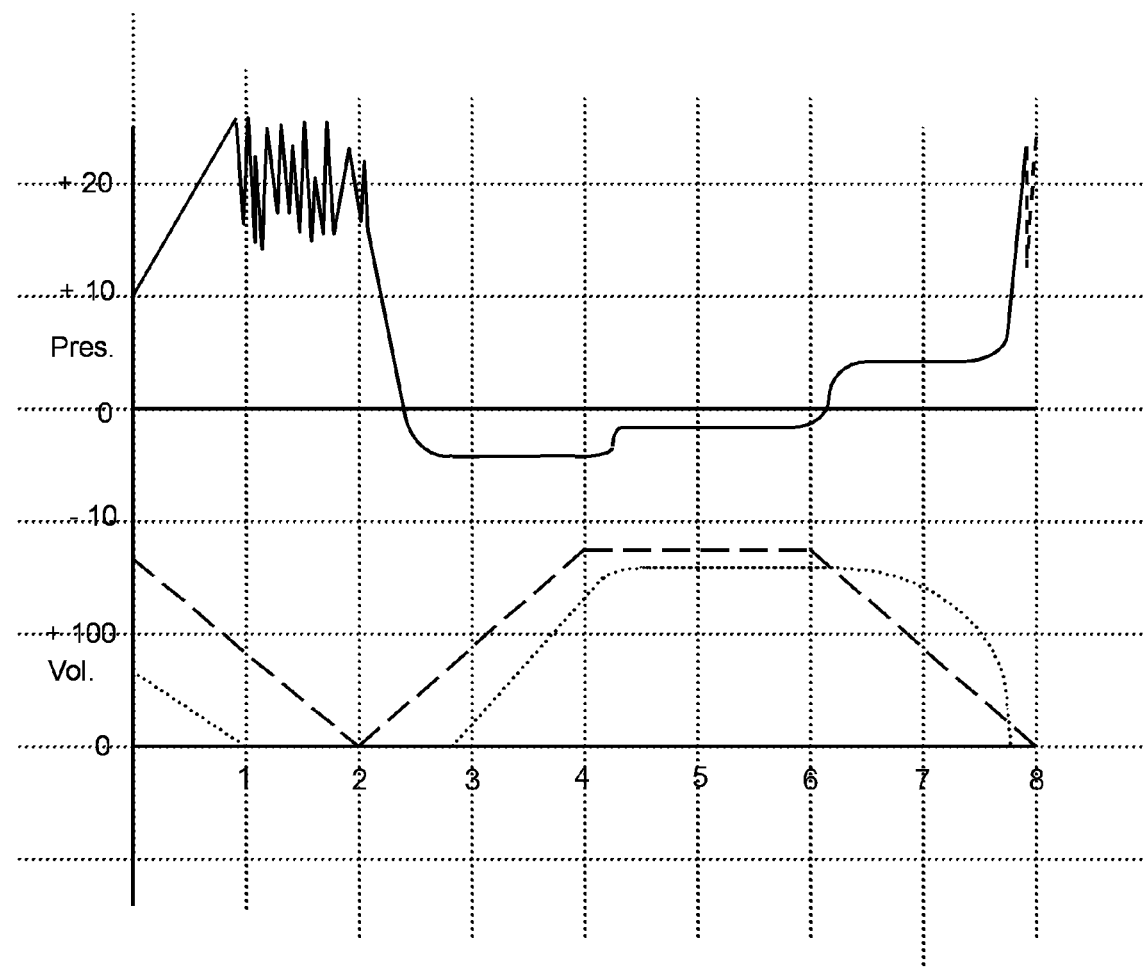
FIG. 16 plots the head pressure of a pipette tip column, the chamber volume of a syringe attached to the pipette tip column, and the volume of liquid in the column, all as a function of time, during a typical extraction process.

FIG. 16 depicts the relationship between head pressure and pump and liquid movement in a typical extraction process. This particular plot represents an initial expulsion of liquid out of the column and then one cycle of uptake and expulsion of liquid from the column. The x-axis is time, and the y-axis is pressure or volume. The solid line at the top represents head pressure as a function of time, the dashed line represents displacement of a pipettor (in this case a syringe), and the dotted line at the bottom represents the volume of liquid in a pipette tip column. A syringe is being used as the pump; movement of the syringe plunger causes a change in the volume of the syringe chamber, which is filled with air and sealingly connected to the open upper end of a tip column as depicted in FIG. 15. At time zero, the volume of liquid (e.g., aqueous solution) in the tip is about 60 uL, the volume of the syringe chamber is about 160 uL, and the head pressure is about +10 inches of water. As the syringe plunger is depressed, the volume of the syringe chamber decreases, which causes the positive head pressure to increase. This increase in head pressure causes the liquid to be expelled from the open lower end of the column, resulting in a decrease in the volume of liquid in the column. As the volume of liquid in the tip approaches zero, the head pressure begins to fluctuate. At this point, little if any liquid is leaving the bed, but there is still some liquid remaining in the interstitial space of the bed. The interaction of this liquid with the bed and frits results in a surface tension effect that impedes the flow of air through the bed. As the volume of the syringe chamber continues to decrease, the increasing positive head pressure will eventually force air through the bed in the form of air bubbles. The surface tension in the bed resists movement of the air bubbles through the bed, but air bubbles will be ejected once sufficient positive head pressure is achieved. The passage of each air bubble through the bed and out of the column will result in a decrease in the head pressure. The result is large fluctuations in the head pressure as the syringe plunger is depressed under these conditions; the head volume builds up as the syringe chamber volume decreases, but with each air bubble expelled through the bed the head pressure will decrease. In many cases dramatic fluctuations in head pressure are observed, as depicted in FIG. 16 between times 1 and 2 (1 and 2 minutes). Each spike represents the head pressure at which an air bubble was forced out of the column.

At time 2 the volume of the syringe chamber is zero, and the plunger is now retracted, resulting in the increase of the syringe chamber volume with time. The increasing syringe chamber volume translates into decreasing head pressure, eventually resulting in a negative head pressure at a time of about 2.5. Once the head pressure is sufficiently negative to overcome the surface tension and backpressure effects, liquid starts flowing through the bed and back into the head space. At time 4 the plunger stops moving and the syringe chamber volume has reached its maximum. Liquid stops flowing into the tip, and the head pressures stabilizes at a constant, moderately low pressure.

Starting at time 6, the plunger is again depressed, resulting in an increase in head pressure up to a pressure that is sufficiently positive that liquid begins flowing out of the tip. Note that some head pressure results from the weight of the liquid above the bed in the head space, and this can contribute to the pressure that is being applied to expel the liquid. Between time points 7.5 and 8 all of the bulk of the liquid is ejected from the column, and the head pressure rises again dramatically due to the backpressure and surface tension effects described earlier, i.e., as in the conditions between 1 and 2 minutes.

In certain embodiments of the invention, it is desirable to adjust the head pressure prior to or during the course of a purification process, e.g., prior to a pumping step. Adjustment of the head pressure is particularly important in automated processes, e.g., processes involving automated, programmable and/or robotic pipettors, and in processes employing a plurality of tip columns, e.g., multiplexed processes.

In a process where a syringe or a manual pipettor is used, e.g., the traditional, manually-operated Gilson Pipetteman®, head pressure is typically not a major issue because the user can compensate for any head pressures in real-time during operation of the pipettor. For example, in taking up desorption solution the user will visually monitor the uptake of fluid, and will intuitively retract the plunger enough to overcome any residual positive pressure and draw the desired amount of liquid through the bed. Any adjustment of the head pressure is so trivial that the user will likely not be conscious of it. But this is a consequence of the user being able to visually monitor fluid uptake and to adjust movement of the plunger accordingly.

However, when using a programmable pipettor, such as an automated multi-channel pipettor (for example, the ME-200 instrument, available from PhyNexus, Inc., San Jose, Calif.), the head pressure can become a critical issue. Typically, the pipettor pumps gas into or out of the head space by movement of a displacing piston within a displacement cylinder having a displacement chamber and having another end with an aperture in communication with the head space (see, e.g., U.S. Pat. Nos. 4,905,526, 5,187,990 and 6,254,832). The rate and extent of piston movement (i.e., the piston displacement) is controlled by a microprocessor, which is programmed by the operator. The operator will program an amount of piston displacement that will alter the head pressure sufficiently to draw or expel a desired amount of liquid through the bed. The amount of piston displacement required will depend upon the amount of liquid to be passed through the bed, the resistance to flow through the bed (e.g., backpressure, surface tension), and must also be enough to compensate for any residual head pressure present prior to pump displacement.

For example, consider the case where the next step in a process is the uptake of a desorption solution, and there is a residual positive head pressure as the result of a previous step of expelling a wash solution. In order to take up desorption solution, the operator must program the microprocessor to direct a piston displacement sufficient to neutralize the residual head pressure and then to introduce a negative pressure into the head space sufficient to overcome resistance to flow and to draw up the desired amount of desorption solution. The volume of desorption solution is often small, and accurate uptake of the correct amount is important in order to achieve the optimal recovery and concentration of the final product. It is apparent that in order to program the correct piston displacement, it is imperative that the residual head pressure be known and accounted for, and/or that the head pressure be adjusted. If the head pressure is not taken into account, the piston displacement will be incorrect, as will the amount of liquid taken up. The larger the head pressure, or variations in head pressure, relative to the amount of liquid taken up the more of an issue it becomes.

For example, in FIG. 16 the head pressures at time 3 and 7 represent the head pressures capable of drawing liquid in through the bed and to expel liquid out through the bed, respectively. Note that the difference in head pressure between times 3 and 7 is less than 10 inches of water; thus, a difference in head pressure of less than 10 is the difference between fluid uptake and expulsion. Now consider the fluctuation in head pressure between times 1 and 2; the head pressure varies by greater than 10 inches of water. This is the changes in head pressure that can be generated as the syringe head space decreases (increasing the head pressure) and bubbles of air are intermittently force through the bed (decreasing the head pressure). Depending upon at what point in time the plunger depression is stopped, the head pressure can vary between 15 and 25 inches of water at the stopping point. This head pressure is the residual head pressure that must be accounted for when beginning the fluid uptake step, i.e., by beginning to pull up the plunger at time 2. The extent to which the plunger must be pulled up, i.e., the volume to which the syringe chamber must be increased to draw up the desired amount of liquid depends upon the residual head pressure. For example, if the residual head pressure is 25 the change in syringe chamber volume required to achieve the necessary negative head pressure will be substantially less than if the residual head pressure is 15. A change in syringe chamber volume that is sufficient to draw up, e.g., 20 uL of liquid when the residual head pressure is 15 will in many cases be insufficient to draw up the same amount of liquid (or possibly any liquid) when the residual head pressure is 25. On the other hand, a change in syringe chamber volume that is sufficient to draw up 20 uL of liquid when the residual head pressure in 25 might be excessive when the residual head pressure is only 15. An excessive change in head pressure volume can lead to drawing up too much liquid. Or if the liquid is being drawn from a container (e.g., an Eppendorf tube) containing only the 20 uL of liquid, the excessive change in syringe chamber volume will result in drawing up air through the bed after the 20 uL has been drawn up. This can negatively impact the outcome of a purification procedure, since it can result in bubbles of air being drawn up through the bed that can break through and cause liquid to be splattered in the head space. This can result in droplets of liquid becoming stuck to the walls of the through passageway, instead of forming a continuous body of liquid on top of the upper membrane. When the liquid is subsequently pumped out of the bed, these droplets might be left behind. When the liquid is a small volume of desorption solution being used in a sample elution step, these non-recovered droplets can result in substantial sample loss, i.e., low sample recovery.

Another scenario where residual head volume can pose substantial problems in an automated purification process is where multiple pipette tip columns (two or more) are being used, either simultaneously or in series. For example, consider an extraction process developed for use with a particular pipette tip column, and intended to be used to extract samples with multiple pipette tip columns of the same type, e.g., substantially the same column dimensions, head space, extraction media, bed size, etc. As described above, the process will be accompanied by variations in the head pressure, and particularly with the build up of residual head pressures (either negative or positive) that will be present prior to beginning each liquid uptake or expulsion step. In practice, what is often observed is that residual head pressure present at any given step in the process will vary from column to column unless measures are taken to adjust the head pressure. This variation can be the result of any of a number of factors, including the type of head pressure fluctuations seen between times 1 and 2 in FIG. 16, and also because of slight variations from column to column, reflecting subtle difference in the packing of the bed and of the interaction of the bed with the frits and with the liquid, i.e., differential surfaced tension and back pressure effects. Because the residual head pressures can vary from run to run and column to column, the appropriate extent of syringe plunger movement (equivalent to movement of the displacing piston in a pipettor) will likewise vary.

This can be the case where multiple columns are run sequentially (in series), and one wishes to program an automated pipettor to draw the correct amount of liquid at each step. If the residual head pressure at the beginning of a given steps varies from column to column, then the appropriate displacement volume to achieve the desired amount of sample uptake (or expulsion) will likewise vary.

This can also be the case when multiple columns are run concurrently and/or in parallel, e.g., as accomplished via a multi-channel pipettor or robotic liquid handling system. Because of subtle differences from tip to tip, different residual head pressures can develop from tip to tip. If these head pressures are not adjusted prior to a given step, and the same pre-programmed volume displacement is used for each channel of the multi-channel device, then the types of problems discussed above can arise.

In certain embodiments, the invention provides methods of addressing the problems associated with the above-described variations in head pressure. These methods involve adjusting the head pressure at various steps prior to and/or during a sample purification procedure.

In one approach to keeping the head pressure constant across several tip columns is to start with approximately the same liquid volume in each tip and then avoid expelling or drawing air through any bed during the various steps in a purification process.

For example, the invention provides a method for passing liquid through a packed-bed pipette tip column comprising the steps of:

(a) providing a first column comprising: a column body having an open upper end for communication with a pump, a first open lower end for the uptake and dispensing of fluid, and an open passageway between the upper and lower ends of the column body; a bottom frit attached to and extending across the open passageway; a top frit attached to and extending across the open passageway between the bottom frit and the open upper end of the column body, wherein the top frit, bottom frit, and surface of the passageway define a media chamber; a first packed bed of media positioned inside the media chamber; a first head space defined as the section of the open passageway between the open upper end and the top frit, wherein the head space comprises a gas (typically air) having a first head pressure; and a pump (e.g., a pipettor or syringe) sealingly attached to the open upper end, where actuation of the pump affects the first head pressure, thereby causing fluid to be drawn into or expelled from the bed of media;

(b) contacting said first open lower end with a first liquid;

(c) actuating the pump to draw the first liquid into the first open lower end and through the first packed bed of media; and (d) actuating the pump to expel at least some of the first liquid through the first packed bed of media and out of the first open lower end.

In some embodiments, the method further comprising the following steps subsequent to step (d):

e) contacting said first open lower end with a second liquid, which is optionally the same as the first liquid;

f) actuating the pump to draw second liquid into the first open lower end and through the first packed bed of media; and g) actuating the pump to expel at least some of the second liquid through the first packed bed of media and out of the first open lower end.

In various embodiments of the invention, the head pressure of the first column is adjusted at one or more points in the process, e.g., to address the head pressure issues discussed above. For example, the first head pressure of the first column can be adjusted between steps (d) and (f) to render the head pressure closer to a reference pressure, or equal or substantially equal to a reference head pressure. The reference head pressure can be any pressure desired to achieve the desired uptake or expulsion of liquid when the pump is actuated. The pressure can be predetermined, e.g., by determining the head pressure in a reference run wherein the degree of movement of a piston is calibrated to achieve the expulsion or uptake of a desired amount of liquid. For example, the reference head pressure can be the head pressure of the first column prior to step (c). The reference head pressure can be based upon a standard external to the head space, e.g., the ambient air pressure. For example, one way of adjusting the head pressure to a predetermined value is to expose the head space to the external environment (by allowing air to pass to or from the head space), thereby normalizing the head space pressure to the ambient pressure. This can be accomplished, e.g., by breaking the seal between the upper open end and the pump (for example, by taking a pipette tip column off a pipettor and then putting it back on, thereby dispelling any negative or positive head pressure and normalizing the head pressure to the ambient air pressure). For example, consider multiple pipette tip columns, each attached to a pipettor channel and each having a different head pressure as a result a previous liquid uptake or expulsion operation. One could briefly disengage each tip column from the pipettor channel, allowing the head space to equilibrate with the ambient air pressure and thereby normalizing the head pressures. The same technique also applies to a single pipette tip column; the normalization of the head pressure will assure consistent head pressures at the beginning of a given step and equal volumes of liquid taken up from run to run.

Some embodiments involve additional steps of:

(h) providing a second column comprising: a column body having an open upper end for communication with a pump, a second open lower end for the uptake and dispensing of fluid, and an open passageway between the upper and lower ends of the column body; a bottom frit attached to and extending across the open passageway; a top frit attached to and extending across the open passageway between the bottom frit and the open upper end of the column body, wherein the top frit, bottom frit, and surface of the passageway define a media chamber; a second packed bed of media positioned inside the media chamber; a second head space defined as the section of the open passageway between the open upper end and the top frit, wherein the head space comprises a gas having a second head pressure; and a pump sealingly attached to the second open upper end, where actuation of the pump affects the second head pressure, thereby causing fluid to be drawn into or expelled from the second packed bed of media;

i) contacting said second open lower end with a third liquid, which is optionally the same as the first liquid;

j) actuating the pump to draw the third liquid into the second open lower end and through the second packed bed of media;

k) actuating the pump to expel at least some of the third liquid through the second packed bed of media and out of the second open lower end.

l) contacting said second open lower end with a fourth liquid, which is optionally the same as the third liquid;

m) actuating the pump to draw fourth liquid into the second open lower end and through the second packed bed of media; and n) actuating the pump to expel at least some of the fourth liquid through the second packed bed of media and out of the second open lower end, wherein the head pressure of the second column is adjusted between steps (k) and (m) to render the head pressure closer to a reference pressure.

In some embodiments, steps (b) through (g) are performed prior to steps (i) through (n). In other embodiments steps (b) through (g) are performed concurrently and in parallel with steps (i) through (n). That is the, two columns can be run sequentially or in parallel, such as in multiplexed extraction procedures. In some embodiments, the reference head pressure is the head pressure of the first column immediately prior to the commencement of step (f).

The pump can be any of the pumps described throughout this specification, such as a syringe pump or pipettor. For example, in some embodiments the pump is a multi-channel pipettor and the first column is attached to a first channel of the multi-channel pipettor and the second column is attached to a second channel of the multi-channel pipettor.

In some embodiments, between steps (d) and (f) the first head pressure is adjusted to render the first and second head pressures more uniform. In other methods the head pressures are adjusted to be more uniform at any other step in the process, particularly before any step involving the uptake or expulsion of liquid.

In some embodiments, the method is applied concurrently and in parallel to multiple pipette tip columns sealingly attached to a multi-channel pipettor (such as robotic workstation), wherein each pipette tip column comprises a head space having a head pressure, and wherein the head pressures of the multiple pipette tip columns are adjusted to render the head pressures more uniform. The multiple pipette tip columns can comprise at least 2, at least 4, at least 6, at least 8, at least 16, at least 32, at least 96, or more pipette tip columns. In some embodiments the head pressures of the multiple pipette tip columns are adjusted to render the head pressures substantially equal.

Head pressure can be adjusted by any of a number of methods. As described above, the head pressure can be adjusted by breaking the sealing attachment between the pump and the open upper end of a column, exposing the head space to ambient pressure, and sealingly reattaching the pump to the open upper end of the column.

Alternatively, a column can be employed that includes a valve in communication with the head space, and the head pressure is adjusted by opening this valve, thereby causing gas to enter or exit the head space. For example, a 3-way valve can be attached between a pump fitting and a pipette tip column. Opening the valve will allow external air to enter or leave the head space, thereby allowing equilibration of the head pressure with the external pressure, e.g., the ambient pressure.

In another alternative, the head pressure is adjusted by means of the pump itself. The pump can be actuated to pump air into or out of the head space, thereby adjusting the pressure of the head space to a desired level. In some embodiments a pressure sensor is positioned in operative communication with a head space and used to monitor the head pressure and to determine the amount of gas to be pumped into or from the head space to achieve the desired pressure adjustment. The pressure sensor can provide real-time feedback to an automated pumping system (e.g., a multi-channel pipettor or robot) during a purification process, and cause the appropriate actuation of the pump to adjust the head space to a desired pressure. For example, in one embodiment a first column comprises a first pressure sensor in operative communication with the first head space, a second pressure sensor in operative communication with the second head space, which is optionally the same as the first pressure sensor, wherein said pressure sensors are used to monitor the first and second head pressures and to determine the amount of gas pumped into or from the second head space. The method can be applied to any number of multiple columns being used in parallel and/or sequentially.

In another embodiment, head pressure is adjusted by removing bulk liquid from the interstitial space of a packed bed of media, e.g., by blowing air through the bed. In some cases it takes relatively high head pressure to blow the residual liquid out of the bed, e.g., by rapidly pumping air through the bed. Often times, once the liquid has been blown out and replaced by air, air from outside the column can more easily traverse the bed and enter the head space, thereby equilibrating the head pressure with the ambient air pressure. This is because the resistance to air flow of a "dried bed" of extraction media is typically substantially less than the resistance of the corresponding "wet bed." The term "dried bed" refers to a bed wherein the interstitial space is substantially void of liquid, although there can be some residual bulk liquid and the media itself might be hydrated. "Wet bed" refers to a bed wherein the interstitial space is substantially filled with liquid. Surface tension in the wet bed presumably restricts the flow of gas through the bed, allowing for maintenance of substantial pressure differentials between the head space and the external ambient environment.

In order to expel all liquid from a pipette tip column, the syringe plunger or displacing piston must be able to displace enough chamber volume to achieve the required positive head pressure. Consider the case where a displacing piston starts at a given starting position corresponding to a starting chamber volume. The piston is retracted, increasing the chamber volume and resulting in the uptake of liquid. The piston is then extended back to the starting position, reducing the chamber volume to the starting chamber volume. In some cases, due for example to the surface tension and other effects described herein, the extension of the piston back to the starting position is insufficient to expel all of the liquid from the tip as desired. It is thus necessary to extend the piston beyond the starting position to expel the full amount of liquid. This is impossible if the starting position of the piston is at the fully extended position, i.e., the typical starting point, where the chamber volume is at its minimum. Thus, in some embodiments of invention, the piston (or its equivalent, such as the plunger in a syringe) is retracted to some extent from the fully extended position before beginning to take up any liquid, i.e., the starting position is displaced from the fully extended position, and hence the chamber volume is greater than the minimum. This is advantageous in that it allows the piston to be extended beyond the starting point during liquid expulsion, allowing for the creation of greater positive head pressure to expel all of the liquid from the column as desired. The greater the displacement of the starting position from the fully extended position, the greater the head pressure that can be created at the end of the extension step. The degree of displacement should be enough to compensate for backpressures encountered in the particular column system at hand, and can be determined empirically or calculated based on the properties of the column, sample liquid, pump system, etc.

Thus, in one embodiment the invention provides a method of purifying an analyte comprising the steps of: (a) providing a column comprising: a column body having an open upper end for communication with a pump, an open lower end for the uptake and dispensing of fluid, and an open passageway between the upper and lower ends of the column body; a bottom frit attached to and extending across the open passageway; a top frit attached to and extending across the open passageway between the bottom frit and the open upper end of the column body, wherein the top frit, bottom frit, and surface of the passageway define a media chamber; a packed bed of media positioned inside the media chamber; a head space defined as the section of the open passageway between the open upper end and the top frit, wherein the head space comprises a gas having a head pressure; and a pump (e.g., a pipettor or syringe) sealingly attached to the open upper end, wherein the pump includes a linear actuator (which can be controlled by an electrically driven microprocessor) and, connected to and controlled by the linear actuator, a displacement assembly including a displacing piston moveable within one end of a displacement cylinder having a displacement chamber and having an end with an aperture in communication with the head space; (b) positioning the piston at a starting position that is displaced from a full-extended position that corresponds to a minimum displacement chamber volume, wherein the starting position is sufficiently displaced from the fully-extended position such that full extension of the piston will cause full expulsion of liquid from the column during an expulsion step in the process (full expulsion being defined as the expulsion of all liquid or some of the liquid to the extent desired by the operator of the method); (c) positioning the open lower end into a liquid (either before, after, or concurrently with step (b)); retracting the piston to draw liquid through the open lower end and into the packed bed of media; and (d) extending the piston beyond the starting point, thereby expelling the liquid through the packed bed of media and out of the open lower end.

Note that the above described method can result in a negative head pressure prior to retracting the piston and drawing up the liquid.

As discussed above, unintended variability in head pressure is often the result of the intermittent seal formed by the bed of extraction media and media chamber. When the interstitial space is substantially full of liquid, a seal is formed that prevents air from entering or leaving the head space. If air is permitted to enter the bed during an extraction process it can form air channels in the bed through which air can pass, i.e., the seal is disrupted. Thus, in one embodiment of the invention unintended variations in head pressure are prevented by maintaining the seal throughout an extraction process, e.g., by preventing air from entering the chamber.

For example, in one embodiment, each actuation of the pump to draw liquid into the chamber comprises inducing a negative head pressure that is sufficient to draw up a desired quantity of liquid but which is not so great as to cause air to enter the media chamber through the bottom frit. In some embodiments, the induced negative pressure is predetermined to be sufficient to draw up a desired quantity of liquid but is not so great as to cause air to enter the media chamber through the bottom frit.

Methods that involve preventing entry of air into the media chamber are particularly relevant in embodiments of the invention employing membrane frits.

In certain embodiments, after the liquid has been drawn into the media chamber the outer surface of the bottom frit is in contact with air (e.g., all of the liquid in a well has been drawn up), but the air is prevented from entering or traversing the media chamber by a surface tension that resists the passage of gas through the membrane frit and media chamber. Optionally, the magnitude of the negative pressure is predetermined to be sufficient draw the liquid into the media chamber but not so great as to overcome the surface tension that resists the passage of gas through the membrane frit and media chamber. In some cases, there is a surface tension that resists the initial entry of the liquid through the open lower end of the column body and into the media chamber, and the magnitude of the negative pressure is predetermined to be sufficient to overcome the surface tension that resists the initial entry of the liquid through the open lower end of the column body and into the media chamber.

One point at which there is a particular danger of air channels forming in the bed of extraction media is upon attachment of a column to a pump, e.g., attachment of a pipette tip column to a pipettor. Attachment of the tip will generally cause an increase in head pressure, and this increase in head pressure can drive liquid out of the interstitial space of the media bed and result in the formation of channels. A way to avoid this is to ensure that there is sufficient liquid in the interstitial space prior to attaching the tip to a pump, so that the interstitial space remains substantially full of liquid. In this regard, it can be advantageous to use a liquid that is more viscous than water as a storage liquid for a column, e.g., glycerol. A variety of water miscible solvents, including glycerol, are described herein in connection with storage of tips in a wet state. Thus, another advantage of many of these solvents is that they will be retained in the bed better than water, and will be less likely to be forced out by head pressure resulting from attachment of the column to a pump.

Maintaining Pipette Tip Columns and Polymer Beads in a Wet State

In certain embodiments, the invention provides methods of storing pipette tip columns in a wet state, i.e., with a "wet bed" of extraction media. This is useful in it allows for preparing the columns and then storing for extended periods prior to actual usage without the bed drying out, particularly where the extraction media is based on a resin, such as a gel resin. For example, it allows for the preparation of wet columns that can be packaged and shipped to the end user, and it allows the end user to store the columns for a period of time before usage. In many cases, if the bed were allowed to dry out it would adversely affect column function, or would require a time-consuming extra step of re-hydrating the column prior to use.

The maintenance of a wet state can be particularly critical wherein the bed volume of the packed bed is small, e.g., in a range having a lower limit of 0.1 µL, 1 µL, 5 µL, 10 µL, or 20 µL, and an upper limit of 5 µL, 10 µL, 20 µL, 50 µL, 100 µL, 200 µL, 300 µL, 500 µL, 1 mL, 2 mL, 5 mL, 10 mL, 20 mL, or 50 mL. Typical ranges would include 0.1 to 100 µL, 1 to 100 µL, 5 to µL, 10 to 100 µL, 1 to 20 µL, 1 to 10 µL, 5 to 20 µL, and 5 to 10 µL.

The wet tip results from producing a tip having a packed bed of media wherein a substantial amount of the interstitial space is occupied by a liquid. Substantial wetting would include beds wherein at least 25% of the interstitial space is occupied by liquid, and preferably at least 50%, 70%, 80%, 90%, 95%, 98%, 99%, or substantially the entire interstitial space is occupied by liquid. The liquid can be any liquid that is compatible with the media, i.e., it should not degrade or otherwise harm the media or adversely impact the packing. Preferably, it is compatible with purification and/or extraction processes intended to be implemented with the column. For example, trace amounts of the liquid or components of the liquid should not interfere with solid phase extraction chemistry if the column is intended for use in a solid phase extraction. Examples of suitable liquids include water, various aqueous solutions and buffers, and various polar and non-polar solvents described herein. The liquid might be present at the time the column is packed, e.g., a solvent in which the extraction media is made into a slurry, or it can be introduced into the bed subsequent to packing of the bed.

In certain preferred embodiments, the liquid is a solvent that is water miscible and that is relatively non-volatile and/or has a relatively high boiling point (and preferably has a relatively high viscosity relative to water). A "relatively high boiling point" is generally a boiling point greater than 100° C., and in some embodiments of the invention is a boiling point at room temperature in range having a lower limit of 100° C., 110° C., 120° C., 130° C., 140° C., 150° C., 160° C., 170° C., 180° C., 190° C., 200° C., or higher, and an upper limit of 150° C., 160° C., 170° C., 180° C., 190° C., 200° C., 220° C., 250° C., 300° C., or even higher. Illustrative examples would include alcohol hydrocarbons with a boiling point greater than 100° C., such as diols, triols, and polyethylene glycols (PEGs) of n=2 to n=150 (PEG-2 to PEG-150), PEG-2 to PEG-20, 1,3-butanediol and other glycols, particularly glycerol and ethylene glycol. The water miscible solvent typically constitutes a substantial component of the total liquid in the column, wherein "a substantial component" refers to at least 5%, and preferably at least 10%, 20%, 30%, 40%, 50%, 60%, 70%, 80%, 90%, 95%, 98%, 99%, or substantially the entire extent of the liquid in the column.

An advantage of these non-volatile solvents is that they are much less prone to evaporate than the typical aqueous solutions and solvents used in extraction processes. Thus, they will maintain the bed in a wet state for much longer than more volatile solvents. For example, an interstitial space filled with glycerol will in many cases stay wet for days without taking any additional measures to maintain wetness, while the same space filled with water would soon dry out. These solvents are particularly suitable for shipping and storage of gel type resin columns having agarose or sepharose beds. Other advantageous properties of many of these solvents, is that they are viscous so it is not easily displaced from column from shipping vibrations and movements, they are bacterial resistant, they do not appreciably penetrate or solvate agarose, sepharose, and other types of packing materials, and they stabilize proteins. Glycerol in particular is a solvent displaying these characteristics. Note that any of these solvents can be used neat or in combination with water or another solvent, e.g., pure glycerol can be used, or a mixture of glycerol and water or buffer, such as 50% glycerol or 75% glycerol.

One advantage of glycerol is that its presence in small quantities has negligible effects on many solid-phase extraction processes. A tip column can be stored in glycerol to prevent drying, and then used in an extraction process without the need for an extra step of expelling the glycerol. Instead, a sample solution (typically a volume much greater than the bed volume, and hence much greater than the volume of glycerol) is loaded directly on the column by drawing it up through the bed and into the head space as described elsewhere herein. The glycerol is diluted by the large excess of sample solution, and then expelled from the column along with other unwanted contaminants during the loading and wash steps.

Note that relatively viscous, non-volatile solvents of the type described above, particularly glycerol and the like, are generally useful for storing polymer beads, especially the resin beads as described herein, e.g., agarose and sepharose beads and the like. Other examples of suitable beads would include xMAP® technology-based microspheres (Luminex, Inc., Austin, Tex.). Storage of polymer beads as a suspension in a solution comprising one or more of these solvents can be advantageous for a number of reasons, such as preventing the beads from drying out, reducing the tendency of the beads to aggregate, and inhibiting microbial growth. The solution can be neat solvent, e.g., 100% glycerol, or a mixture, such as an aqueous solution comprising some percentage of glycerol. The solution can also maintain the functionality of the resin bead by maintaining proper hydration, and protecting any affinity binding groups attached to the bead, particularly relatively fragile functional groups, such as certain biomolecules, e.g., proteins.

This method of storing suspensions of polymer beads is particularly valuable for storing small volume suspensions, e.g., volumes falling with ranges having lower limits of 0.1 µL, 0.5 µL, 1 µL, 5 µL, 10 µL, 20 µL, 50 µL, 100 µL, 250 µL, 500 µL, or 1000 µL, and upper limits of 1 µL, 5 µL, 10 µL, 20 µL, 50 µL, 100 µL, 250 µL, 500 µL, 1 mL, 5 mL 10 mL, 20 mL, or 50 mL. Typical, exemplary ranges would include 0.1 to 100 µL, 0.5 to 100 µL, 1 to 100 µL, 5 to 100 µL, 0.1 to 50 µL, 0.5 to 50 µL, 1 to 50 µL, 5 to 50 µL, 0.1 to 20 µL, 0.5 to 20 µL, 1 to 20 µL, 5 to 20 µL, 0.1 to 10 µL, 0.5 to 10 µL, 1 to 10 µL, 0.1 to 5 µL, 0.5 to 5 µL, 1 to 5 µL, and 0.1 to 1 µL.

Factors that can affect the rate at which a column dries include the ambient temperature, the air pressure, and the humidity. Normally columns are stored and shipped at atmospheric pressure, so this is usually not a factor that can be adjusted. However, it is advisable to store the columns at lower temperatures and higher humidity in order to slow the drying process. Typically the columns are stored under room temperature conditions. Room temperature is normally about 25° C., e.g., between about 20° C. and 30° C. In some cases it is preferable to store the pipette tip columns at a relatively low temperature, e.g., between about 0° C. and 30° C., between 0° C. and 25° C., between 0° C. and 20° C., between 0° C. and 15° C., between 0° C. and 10° C., or between 0° C. and 4° C. In many cases tips of the invention may be stored at even lower temperatures, particularly if the tip is packed with a liquid having a lower freezing point than water, e.g., glycerol.

In one embodiment, the invention provides a pipette tip column that comprises a bed of media, the interstitial space of which has been substantially full of liquid for at least 24 hours, for at least 48 hours, for at least 5 days, for at least 30 days, for at least 60 days, for at least 90 days, for at least 6 months, or for at least one year. "Substantially full of liquid" refers to at least 25%, 50%, 70%, 80%, 90%, 95%, 98%, 99%, or substantially the entire interstitial space being occupied by liquid, without any additional liquid being added to the column over the entire period of time. For example, this would include a column that has been packaged and shipped and stored for a substantial amount of time after production.

In one embodiment, the invention provides a packaged pipette tip column packaged in a container the is substantially full of liquid, wherein the container maintains the liquid in the pipette tip to the extent that less than of 10% of the liquid is (or will be) lost when the tip is stored under these conditions for at least 24 hours, for at least 48 hours, for at least 5 days, for at least 30 days, for at least 60 days, for at least 90 days, for at least 6 months, or for at least one year.

In another embodiment, the invention provides a pipette tip column that comprises a bed of media, the interstitial space of which is substantially full of liquid, wherein the liquid is escaping (e.g., by evaporation or draining) at a rate such that less than 10% of the liquid will be lost when the column is stored at room temperature for 24 hours, 48 hours, 5 days, 30 days, 60 days, 90 days, six months or even one year.

In many cases, the wet pipette tip columns described above (e.g., the column that has been wet for an extended period of time and/or the column that is losing liquid only at a very slow rate) is packaged, e.g., in a pipette tip rack. The rack is a convenient means for dispensing the pipette tip columns, and for shipping and storing them as well. Any of a variety of formats can be used; racks holding 96 tips are common and can be used in conjunction with multi-well plates, multichannel pipettors, and robotic liquid handling systems.

Figure 23:
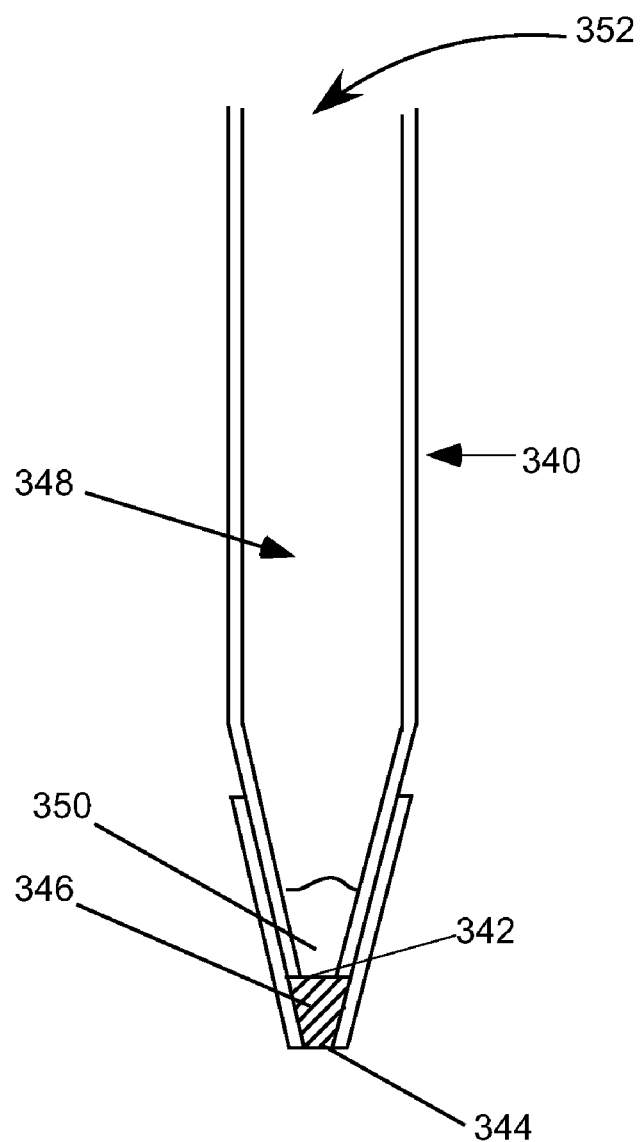
FIG. 23 depicts a pipette tip column to be stored in a wet state.

In various embodiments, the invention provides methods for maintaining the wetness of pipette tip columns. One method is illustrated in FIG. 23. The pipette tip column 340 has a packed bed of media 346 positioned between upper frit 342 and lower frit 344. The packed bed is wet, i.e., the interstitial space is substantially occupied by solvent, in this case an aqueous buffer. In order to inhibit drying of the bed, a quantity of the same aqueous buffer 350 (referred to as a storage liquid) is positioned in the head space 348. The tip is stored with the lower frit down, so gravity maintains the quantity of buffer at the lower end of the head space and in contact with the upper frit. Typically a small quantity of buffer in the head space will have little tendency to flow through the bed and out of the column due to the resistance to flow generated by the bed. The buffer in contact with the top frit serves to maintain the wetness of the bed and frits.

In some embodiments, the pipette tip column is capped at the lower end 344 and/or the upper end 352. This capping serves to restrict evaporation (i.e., desiccation) of liquid from the bed and to thus maintain column wetness. The cap can be any solid substrate that covers the end and fully or partially seals. Examples would be caps formed to fit the end, such as plastic or rubber caps. The cap could be a film or sheet, such as a film made of metal, plastic, polymeric material or the like. A film or sheet is particularly suited to capping multiple caps. For example, a plurality of tips in a tip rack can all be capped at their upper ends with a sheet of foil or plastic film that is laid over and in contact with the tip tops. The cap can be attached to the opening by pressure, or by some adhesive, or any means that will result in a full or partial seal sufficient to inhibit evaporation of liquid from column. For example, a single sheet of foil or plastic can be glued to the top of a plurality of tips arranged in a rack. Preferably the adhesive is one that can does not bind too tightly (i.e., the cap is removably adhered to the column), so that the tips can be uncapped prior to use, and such that the adhesive does not leave a residue on the tip that would interfere with an extraction process. Alternatively, a sheet can be held in contact with the upper ends of the tips by pressure. For example, a sealing sheet can be draped over the upper ends of tips in a rack and a hard cover placed on top of that and in contact with the sheet, thus pressing the sheet against the tops of the tips to form a full or partial seal.

End capping is particularly effective when used in combination with storage liquid in the head space, as described above. The capping of one or both ends restricts the loss of storage liquid, and the storage liquid maintains the wetness of the bed for extended periods of time.

Another method of maintaining column wetness is by packing the tip column in the presence of an antidessicant. An "antidessicant" is any material that is able to moisturize or humidify an environment. One useful antidessicant is hydrated polyacrylamide. For example, an enclosed pipette tip container (a tip rack) can be used for tip storage, wherein the antidessicant is placed in the container and provides a moist environment that resists desiccation of tip columns in the container. In some embodiments, the cap itself comprises an antidessicant. For example, in one preferred embodiment, a porous bag containing hydrated polyacrylamide is used as the cap. The bag caps the tip columns by being pressed against the open upper or lower ends of the tips. Thus, the bag not only inhibits loss of liquid from the column by sealing off the head space and/or bed from the external environment, it also provides a very moist environment.

Positioning Tips for Use in Multiplexed Processes

In some embodiments methods of the invention involve multiplexed extraction by means of a plurality of pipette tip columns and a multi-channel pipettor. The methods can involve drawing liquid from a well in a multi-well plate. The volume of liquid can be relatively small, e.g., on the order of 10 μL or less of desorption solution, and it is often important that substantially the entire volume of liquid is taken up by each of the tips. To achieve this, it is critical that the open lower end of each pipette tip column is accurately placed at a position in each well that is in contact with the fluid and submerged at a depth such that substantially all of the liquid will be drawn into the tip upon application of sufficient negative pressure in the head space. Typically this position is near the center of a circular well, at a depth that is near the bottom of the well (within one to several millimeters) but preferably not in direct contact with the bottom. If the tip makes direct contact with the well surface there is the danger that a seal might form between the tip and the well that will restrict flow of liquid into and/or out of the tip. However, contact between the tip and well bottom will not necessarily prevent or restrict flow into the tip, particularly if no seal is formed between the tip and well.

Figure 24:
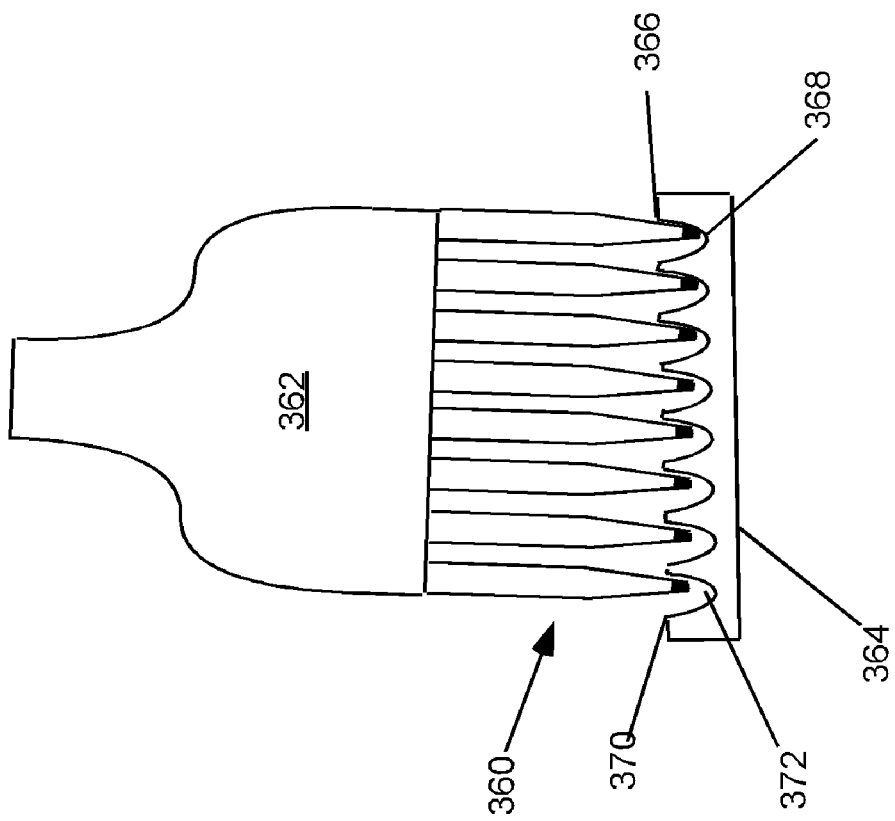

A problem that can arise in a multiplexed purification process is that it can be difficult to accurately position all of the tips on a multichannel pipettor such that each is at the optimal position in its corresponding well. For example, if the open lower ends of each tip are not positioned in substantially a straight line (for a linear configuration of tips) or a plane (for at two-dimensional array of tips), and that line (or plane) is not substantially parallel to the bottoms of the corresponding array of wells in a plate, then it will be very difficult to simultaneously position each tip at its optimal location. This is illustrated in FIG. 24, which depicts eight pipette tip columns 360 attached to an eight channel pipettor 362. The tips are positioned in the wells of a multi-well plate 364, over and close to the bottom of the wells. Because the pipettor is at a slight angle in relation to the plate, the tip at the far right 366 is making contact with the bottom of the well 368, which can restrict flow of liquid through the tip. On the other hand, the tip to the far left 370 is positioned too high, and will not be able to fully draw up a small aliquot of liquid from the bottom of the well 372.

Thus, in one embodiment the invention provides a method for accurately positioning a plurality of tip columns into the wells of a microwell plate. The method as applied to a linear configuration of pipette tip columns is exemplified in FIG. 25. In this case, positioning tips 380 that extend slightly longer than the pipette columns are positioned at either end of the row of pipette tip columns, in an arrangement reminiscent of "vampire teeth." In operation, the positioning tips are positioned so that both rest against the bottom of their corresponding wells 382. The pipette tip columns internal to the two positioning tips are elevated from the bottom of their wells be a distance equal to the distance the positioning tips extend beyond the ends of the pipette tips. Thus, by adjusting the length of the positioning tips it is possible to position the internal tips 384 at any desired distance from the bottom of their corresponding wells. The positioning tips greatly simplify and stabilize the positioning of the pipette tips at a predetermined and uniform distance from the well bottoms.

Figure 25:
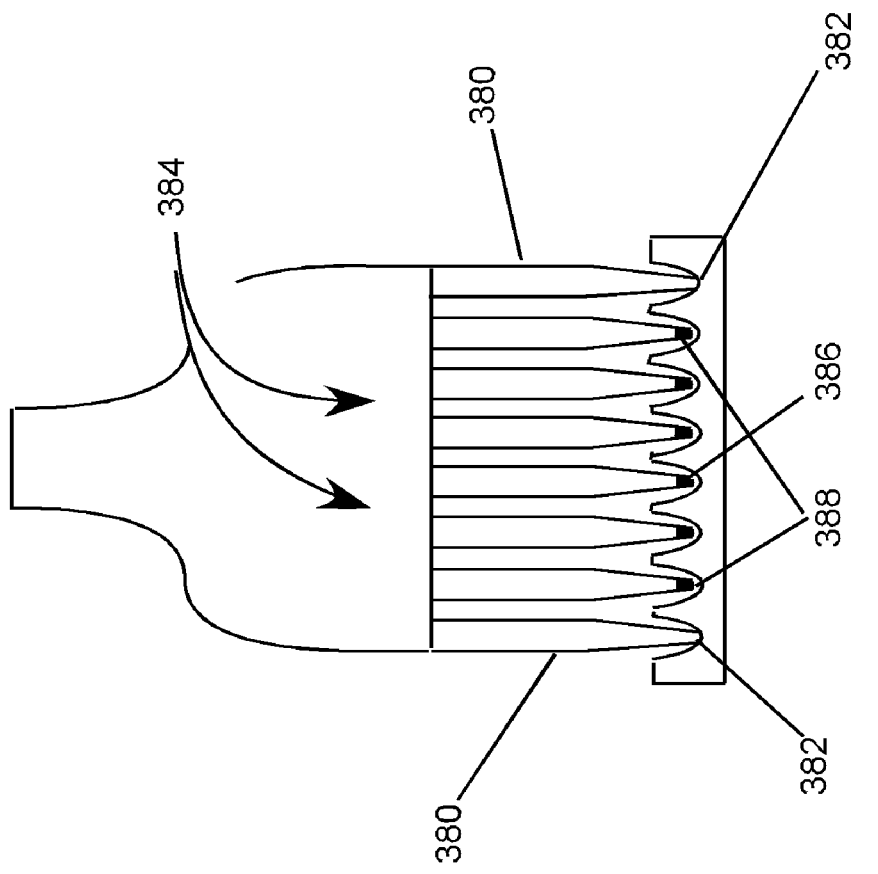
FIGS. 24 through 27 depict a method for positioning pipette tip columns in a multiplexed extraction process.

Note that as depicted in FIG. 25, there are two positioning tips, one at either end of the row of tips. In alternative embodiments a single positioning tip could be used, e.g., at a position near the center of the row like tip 386. In general, the use of a single positioning tip will not afford the stability and accuracy of a multi-positioning tip format, but it will be better than not using a positioning tip at all and in some instances will be sufficient.

Alternatively, more than two positioning tips could be used, although normally two is sufficient for a linear arrangement of pipette tips. However, if the row of tips is significantly longer than eight tips in length, then it might be the case that the additional stability provided by more than two positioning tips is beneficial.

Note that whether one or more tips are used, it is not necessary that the positioning tips take any particular position relative to the tip columns. For example, the arrangement of FIG. 25 could be varied such that the positioning tips are positioned at positions 388, and positions 380 might in this scenario be occupied by functional tip columns.

Figure 26:
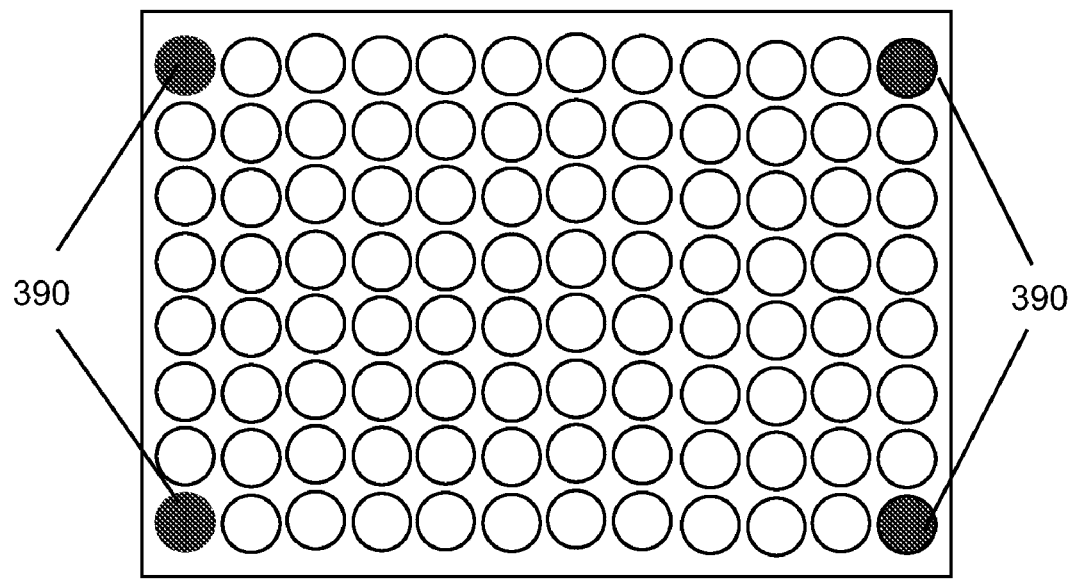
Figure 27:
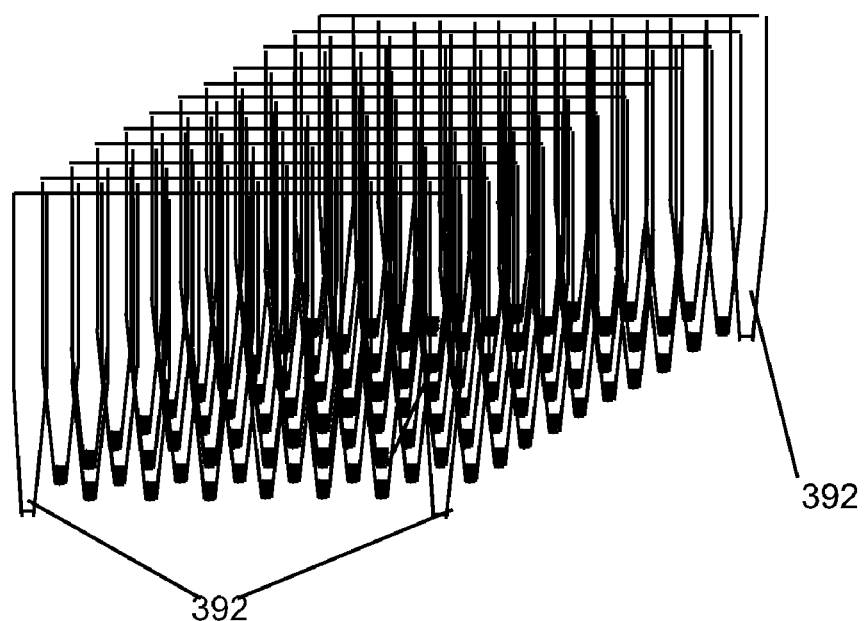

The positioning tips will make contact with a reference point that is located at a fixed, predetermined location relative to the well bottoms corresponding to pipette tip columns. For example, the reference point can be a well bottom not being used in an extraction process. For example, FIG. 27 depicts a 96 well plate. The four corner wells 390 are not used to hold liquid but are rather used as reference points; positioning tips located at the four corners of the two-dimensional array of pipette tip columns in FIG. 26 are brought into contact with the bottoms of the wells 390 to correctly position the pipette tip columns in the corresponding wells of the plate.

The method is also suitable for use with a two-dimensional array of tips, such as on a multi-channel pipettor having more than one row of tip columns, e.g., a 96 channel pipettor that is part of a robotic fluid handling system. For example, FIG. 26 depicts an 8×12 array of 96 pipette tip columns and positioning tips. In this particular example, the positioning tips are at the corners of the array 392. As was the case with linear configurations of tips, in two-dimensional arrays there are a variety of alternative options for the number and location of the positioning tips. For example, in a preferred embodiment four positioning tips are used, one at each corner of the array of tips. Alternatively, more or less than four positioning tips could be used, e.g., two tips, one at each of two opposite corners, or a single tip located at a corner or internal position in the array.

Thus, in certain embodiments the invention provides a general method of positioning a pipette tip column in relative to a well bottom comprising the steps of: (a) providing a pipetting system comprising: (i) a pipettor; (ii) a pipette tip column having an open upper end operatively engaged with said pipettor and an open lower end for passing solution through the pipette tip column; and (iii) a positioning tip attached to said pipettor, said positioning tip having a proximal end attached to the pipettor and a distal end positioned at a fixed., predetermined location relative to the open lower end of the pipette tip column; and (b) positioning the pipetting system so that: (i) the distal end of the positioning tip makes contact with a reference point, wherein said reference point is located at a fixed, predetermined location relative to a well having a well bottom; and (ii) the open lower end of the pipette tip column is positioned over the well bottom.

The pipetting system can be part of a robotic liquid handling system.

In certain embodiments the well contains a liquid, e.g., a sample, wash or desorption solution. In certain embodiments the pipetting system is positioned so that the open lower end of the pipette tip column makes contact with the liquid, and the pipettor is activated to draw liquid through the open lower end and into the pipette tip column.

In certain embodiments the pipettor is a multi-channel pipettor.

Particularly in cases where the pipettor is a multi-channel pipettor, the pipetting system can comprise a plurality of pipette tip columns, each pipette tip column having an open upper end operatively engaged with said pipettor and an open lower end for passing solution through the pipette tip column, wherein the pipetting system is positioned so that: (i) the distal end of the positioning tip makes contact with a reference point, wherein said reference point is located at a fixed, predetermined location relative to a well having a well bottom; and (ii) the open lower end of each of the pipette tip column is positioned over a well bottom of one of the plurality of wells.

In certain embodiments positioning tip is a pipette tip, a pipette tip column, or some other object capable of attachment to the pipettor. The attachment can be transient, or the positioning tip can be permanently affixed to the pipettor or even an integral component of the pipettor.

In certain embodiments the wells are all elements of a multi-well plate, e.g., microwells.

In certain embodiments of the invention involving a multi-well plate, the reference point can be located on the multi-well plate, e.g., the reference point can be the bottom of a well of the multi-well plate.

In certain embodiments, a plurality of positioning tips is used, each positioning tip making contact with a reference point located at a fixed, predetermined location relative to the plurality of wells.

In certain embodiments, the volume of liquid in the wells is relatively low, e.g., in a range having a lower limit of 0.1 μL, 0.5 μL, 1 μL, 2 μL, 5 μL or 10 μL, and an upper limit of 1 μL, 2 μL, 5 μL 10 μL, 20 μL, 30 μL, 50 μL, 100 μL, 200 μL or even 500 μL. For example, in certain embodiments the volume of liquid in the wells is of between 1 and 100 μL, or 1 and 20 μL, or 5 and 20 μL.

In certain embodiments, the open lower end of the pipette tip column is positioned close enough to the well bottom such that upon activation of the pipettor substantially all of the liquid is drawn through the open lower end and into the pipette tip column, but not so close as to form a seal with the well bottom.

The open lower end of the pipette tip column is typically positioned relatively close to the corresponding well bottom, e.g., within a range having a lower limit of about 0.05 mm, 0.1 mm, 0.2 mm, 0.3 mm, 0.4 m, 0.5 mm, 1 mm, 2 mm, 3 mm, 4 mm, or 5 mm from the bottom of the well, and an upper limit of 0.3 mm, 0.4 m, 0.5 mm, 1 mm, 2 mm, 3 mm, 4 mm, 5 mm, 6 mm, 7 mm, 8 mm, 8 mm or 10 mm of the well bottom. For example, in some embodiments the open lower end of a pipette tip column is positioned with between 0.05 and 2 mm from a well bottom, or between 0.1 and 1 mm from a well bottom. The term "well bottom" does not necessarily refer to the absolute bottom of a well, but to the point where the tip makes contact with the well when the tip is lowered to its full extent into the well, i.e., a point where the tip can seal with the well surface. For example, in some microwell plate formats the wells taper down to an inverted conical shape, so a typical tip column will not be able to make contact with the absolute bottom of the well.

In certain embodiments, the positioning tips are longer than the pipette tip columns. The difference in length between positioning tips and pipette tip columns can result in accurately locating the ends of the pipette tip columns at a desired distance from the bottoms of the corresponding wells. The difference in length between positioning tips and pipette tip columns can be relatively small, e.g. in a range having a lower limit of 0.1 mm, 0.2 mm, 0.5 mm, 1 mm or 2 mm and an upper limit of 1 mm, 2 mm, 3 mm, 4 mm, 5 mm 6 mm, 7 mm, 8 mm, 8 mm or 10 mm. For example, in certain embodiments the positioning tips are between 1 and 10 mm longer than the pipette tip columns.

In certain embodiments, a plurality of pipette tip columns and positioning tips are attached to a multi-channel pipettor in a linear configuration. For example, the positioning tips can be positioned at the two ends of the linear configuration of pipette tip columns and positioning tips, e.g., see FIGS. 24 and 25.

In certain embodiments, a plurality of pipette tip columns and positioning tips are attached to a multi-channel pipettor in a two-dimensional array. The two-dimensional array can comprise four corners, with positioning tips are positioned at two or more of the corners. For example, the positioning tips can be positioned at four corners of a two-dimensional array, e.g., see FIGS. 26 and 27.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Preparation of an Extraction Column Body from Pipette Tips

Figure 6:
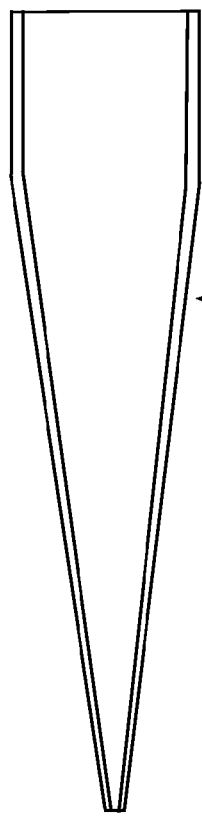
FIGS. 6-10 show successive stages in the construction of the embodiment depicted in FIGS. 1 and 2.

Two 1000 μL polypropylene pipette tips of the design shown in FIG. 6 (VWR, Brisbane, Calif., PN 53508-987) were used to construct one extraction column. In this example, two extraction columns were constructed: a 10 μL bed volume and 20 μL bed volume. To construct a column, various components were made by inserting the tips into several custom aluminum cutting tools and cutting the excess material extending out of the tool with a razor blade to give specified column lengths and diameters.

Figure 7:
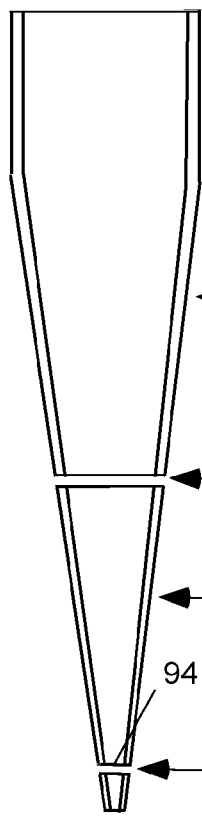

Referring to FIG. 7, the first cut 92 was made to the tip of a pipette tube 90 to form a 1.25 mm inside diameter hole 94 on the lower column body, and a second cut 96 was made to form a lower column body segment 98 having a length of 15.0 mm.

Figure 8:
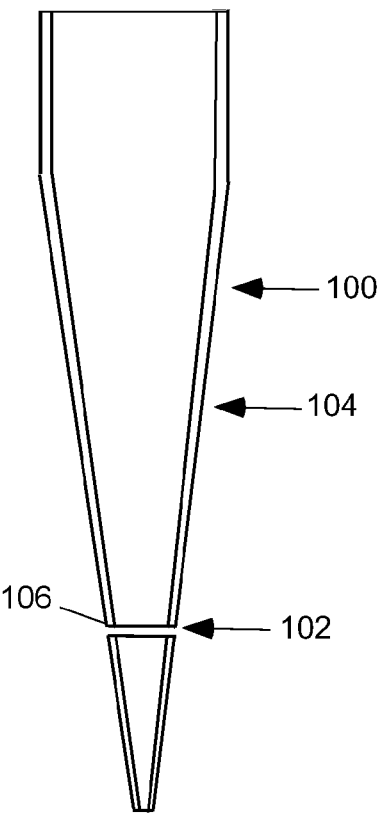

Referring to FIG. 8, a cut 102 was made to the separate pipette tip 100 to form the upper column body 104. To make a 10 μL bed volume column, the cut 102 was made to provide a tip 106 outside diameter of 2.09 mm so that when the upper body was inserted into the lower body, the column height of the solid phase media bed 114 (FIG. 10) was 4.5 mm. To make a 20 μL bed volume column, the cut 102 was made to provide a tip outside diameter of 2.55 mm cut so that when the upper body was inserted into the lower body, the column height of the solid phase media bed 114 (FIG. 10) was 7.0 mm.

Figure 9A:
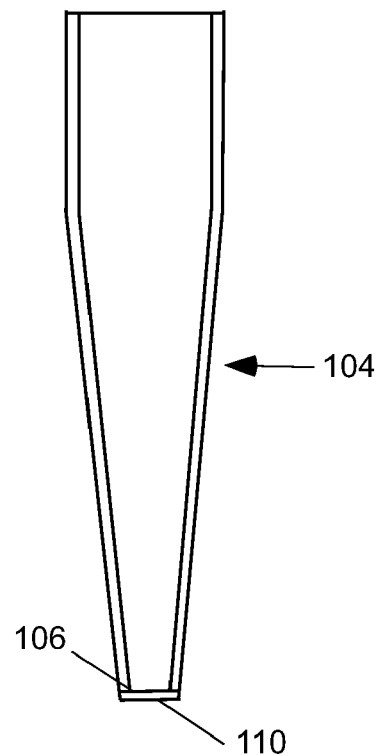
Figure 9B:
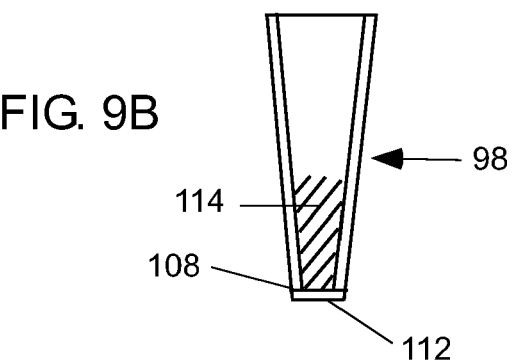

Referring to FIGS. 9A and 9B, a 43 μm pore size Spectra/Mesh® polyester mesh material (Spectrum Labs, Ranch Dominguez, Calif., PN 145837) was cut into discs by a circular cutting tool (Pace Punches, Inc., Irvine, Calif.) and attached to the ends 106 and 108 of the upper column and lower column bodies to form the membrane screens 110 and 112. The membrane screens were attached using PLASTIX® cyanoacrylate glue (Loctite, Inc., Avon, Ohio). The glue was applied to the polypropylene body and then pressed onto the membrane screen material. Using a razor blade, excess mesh material was removed around the outside perimeter of each column body end.

Figure 10:
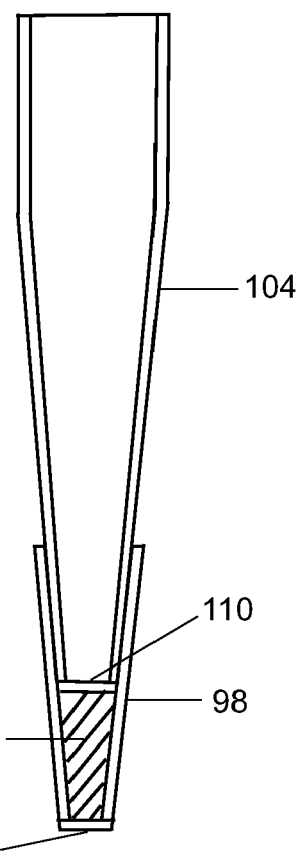

Referring to FIG. 10, the upper column body 104 is inserted into the top of the lower column body segment 98 and pressed downward to compact the solid phase media bed 114 to eliminate excess dead volume above the top of the bed.

Example 2

Preparation of SEPHAROSE™ Protein G and MEP HYPERCEL™ Extraction Columns

Referring to FIG. 9B, a suspension of Protein G SEPHAROSE™ 4 Fast Flow, 45-165 μm particle size, (Amersham Biosciences, Piscataway, N.J., PN 17-0618-01) in water/ethanol was prepared, and an appropriate amount of material 114 was pipetted into the lower column body 98.

Referring to FIG. 10, the upper column body 104 was pushed into the lower column body 98 so that no dead space was left at the top of the bed 114, that is, at the top of the column bed. Care was taken so that a seal was formed between the upper and lower column bodies 104 and 98 while retaining the integrity of the membrane screen bonding to the column bodies.

Several tips of 10 μL and 20 μL bed volumes were prepared. Several MEP (Mercapto-Ethyl-Pyridine) HYPERCEL™ (Ciphergen, Fremont, Calif., PN 12035-010) extraction columns were prepared using the same procedure. MEP HyperCel™ resin is a sorbent, 80-100 μm particle size, designed for the capture and purification of monoclonal and polyclonal antibodies. The extraction columns were stored with an aqueous solution of 0.01% sodium azide in a refrigerator before use.

Example 3

Purification of Anti-leptin Monoclonal Antibody IgG with 10 μL and 20 μL Bed Volume Protein G SEPHAROSE™ Extraction Columns A Protein G SEPHAROSE™ 4 Fast Flow (Amersham Biosciences, Piscataway, N.J., PN 17-0618-01) extraction column was prepared as described in Example 2.

Five hundred μL serum-free media (HTS Biosystems, Hopkinton, Mass.) containing IgG (HTS Biosystems, Hopkinton, Mass.) of interest was combined with 500 μL standard PBS buffer. The resulting 1 mL sample was pulled into the pipette tip, through the Protein G packed bed at a flow rate of approximately 1 mL/min) or roughly 15 cm/min). The sample was then pushed out to waste at the same approximate flow rate. Extraneous buffer was removed from the bed by pulling 1 mL of deionized water into the pipette column at about 1 mL/min and pushing it out at about 1 mL/min. The water was pushed out as much as possible to achieve as dry of a column bed as is possible. The IgG was eluted from the column bed by drawing up an appropriate eluent volume of 100 mM glycine-.HCl, pH 2.5 (20 μL eluent in the case of a 20 μL bed volume, 15 μL eluent in the case of a 10 μL bed volume). When the eluent was fully drawn into the bed, it was "pumped" back and forth through the bed five or six times, and the IgG-containing eluent was then fully expelled from the bed. The eluted material was then neutralized with 100 mM $NaH_2PO_4$/100 mM $Na_2HPO_4$ (5 μL neutralization buffer in the case of a 20 μL bed volume, 4 μL neutralization buffer in the case of a 10 μL bed volume). The purified and enriched antibodies were then ready for arraying.

Example 4

Purification of Anti-leptin Monoclonal Antibody IgG with 10 μL and 20 μL Bed Volume Protein G SEPHAROSE™ Extraction Columns A Protein G SEPHAROSE™ 4 Fast Flow (Amersham Biosciences, Piscataway, N.J., PN 17-0618-01) extraction column was prepared as described in Example 2.

Five hundred μL serum-free media (HTS Biosystems, Hopkinton, Mass.) containing IgG (HTS Biosystems, Hopkinton, Mass.) of interest was combined with 500 μL standard PBS buffer. The resulting 1 mL sample was pulled into the pipette tip, through the Protein G packed bed at a flow rate of approximately 1 mL/min (or roughly 150 cm/min linear velocity). The sample was then pushed out to waste at the same approximate flow rate. Extraneous buffer was removed form the bed by pulling 1 mL of deionized water into the pipette column at about 1 mL/min and pushing it out at about 1 mL/min. The water was pushed out as much as possible to achieve as dry of a column bed as is possible. The IgG was eluted from the column bed by drawing up an appropriate eluent volume of 10 mM phosphoric acid ($H_3PO_4$), pH 2.5 (20 μL eluent in the case of a 20 μL bed volume, 15 μL eluent in the case of a 10 μL bed volume). When the eluent was fully drawn into the bed, it was "pumped" back and forth through the bed five or six times, and the IgG-containing eluent is then fully expelled from the bed. The eluted material was then neutralized with a specially designed phosphate neutralizing buffer of 100 mM $H_2NaPO_4$/100 mM $HNa_2PO_4$, pH 7.5 (5 μL neutralization buffer in the case of a 20 μL bed volume, 4 μL neutralization buffer in the case of a 10 μL bed volume). The purified and enriched antibodies were then ready for arraying.

Example 5

Analysis of Purified IgG with Grating-coupled Surface Plasmon Resonance (GC-SPR)

The anti-leptin monoclonal antibody IgG purified sample from Example 4 was analyzed with GC-SPR. The system used for analysis was a FLEX CHIP™ Kinetic Analysis System (HTS Biosystems, Hopkinton, Mass.), which consists of a plastic optical grating coated with a thin layer of gold on to which an array of biomolecules is immobilized. To immobilize the purified IgG, the gold-coated grating was cleaned thoroughly with EtOH (10-20 seconds under a stream of ETOH). The gold-coated grating was then immersed in a 1 mM solution of 11-mercaptoundecanoic acid (MUA) in EtOH for 1 hour to allow for the formation of a self-assembled monolayer. The surface was rinsed thoroughly with EtOH and ultra-pure water, and dried under a stream of nitrogen. A fresh solution of 75 mM EDC (1-Ethyl-3-(3-Dimethylaminopropyl) carbodiimide hydrochloride) and 15 mM Sulfo-NHS (N-Hydroxysulfo-succinimide) was prepared in water. An aliquot of the EDC/NHS solution was delivered to the surface and allowed to react for 20-30 minutes, and the surface was then rinsed thoroughly with ultra-pure water. An aliquot of 1 mg/mL Protein A/G in PBS, pH 7.4 was delivered to the surface. The surface was placed in a humid environment and allowed to react for 1-2 hours. The surface was allowed to air dry, was rinsed with ultra-pure water and then dried under a stream of nitrogen. Immediately prior to arraying of the IgGs, the surface was rehydrated by placing in a humidified chamber, such as available with commercial arraying systems (e.g. Cartesian MicroSys synQUAD System). The purified anti-leptin IgG was arrayed onto the surface as described previously (J. Brockman, et al, "Grating-Coupled SPR: A Platform for Rapid, Label-free, Array-Based Affinity Screening of Fabs and Mabs", 12th Annual Antibody Engineering Conference, Dec. 2-6, 2001, San Diego, Calif.) and the surface was introduced to the HTS Biosystems FLEX CHIP System. 150 nM leptin in PBS, pH 7.4 was introduced to the surface through the FLEX CHIP System, and real-time binding signals were collected as described previously (ibid.). These real-time binding signals were mathematically processed in a manner described previously (D. Myszka, "Kinetic analysis of macromolecular interactions using surface plasmon resonance biosensors", Current Opinion in Biotechnology, 1997, Vol 8, pp. 50-57) for extraction of the association rate ($k_a$), dissociation rate ($k_d$), and the dissociation affinity constant ($K_d=k_d/k_a$). The kinetic data obtained is shown in Table II below.

TABLE II

|  |  | Serum-free medium | PBS |
|---|---|---|---|
| No processing (Adequate [IgG]) | Mean $K_d$ | 18 nM | 3.2 nM |
|  | Starting [IgG] | 500 μg/mL | 500 μg/mL |
| With processing (Insufficient [IgG] | Mean $K_d$ | 6.6 nM | 5.9 nM* |
|  | Starting [IgG] | 20 μg/mL | 500 μg/mL* |

*500 μg/mL IgG in PBS was not processed, but was included in the SPR analysis for the purpose of comparing dissociation affinity constants calculated for each The first set of data for "No processing" indicates that when sufficient IgG is present for detection (500 μg/mL) that the constituents from the serum-free medium can contribute to inaccuracies. These data indicate for equal concentrations of IgG spotted within an experiment, the calculated dissociation affinity constant can be nearly six-fold different from one another (18 nM vs. 3.2 nM). This can only be a result of components within the serum-free medium being co-arrayed with the IgG, since the concentration and composition of IgG is identical for each sample. Therefore, there is a demonstrated need for removal of any extraneous components prior to arraying, which is independent of IgG concentration.

The second set of data for "With processing" indicates that when insufficient IgG quantities are present for detection (20 μg/mL) that sample processing not only allows for generation of sufficient processable signals, but also eliminates the inaccuracies generated from extraneous components. These data indicate that the dissociation affinity constants are virtually identical for 500 μg/mL purified IgG in PBS (unprocessed) as those calculated from 20 μg/mL IgG in serum-free medium once processed with the current invention (5.9 nM vs. 6.6 nM).

Example 6

Purification of Nucleic Acids with an Extraction Column

Columns from Example 1 are bonded with a 21 μm pore size SPECTRA/MESH® polyester mesh material (Spectrum Labs, Ranch Dominguez, Calif., PN 148244) by the same procedure as described in Example 2. A 10 μL bed volume column is filled with PELLICULAR C18 (Alltech, Deerfield, Ill., PN 28551), particle size 30-50 μm. One end of the extraction column is connected to a pipettor pump (Gilson, Middleton, Wis., P-1000 PipetteMan) and the other end is movable and is connected to an apparatus where the materials may be taken up or deposited at different locations.

The extraction column consists of a 1 mL syringe (VWR, Brisbane, Calif., PN 53548-000), with one end connected to a pipettor pump (Gilson, Middleton, Wis., P-1000 PipetteMan) and the other end is movable and is connected to an apparatus where the materials may be taken up or deposited at different locations.

A 100 μL sample containing 0.01 μg of DNA is prepared using PCR amplification of a 110 by sequence spanning the allelic MstII site in the human hemoglobin gene according to the procedure described in U.S. Pat. No. 4,683,195. A 10 μL concentrate of triethylammonium acetate (TEAA) is added so that the final volume of the solution is 110 μL and the concentration of the TEAA in the sample is 100 mM. The sample is introduced into the column and the DNA/TEAA ion pair complex is adsorbed.

The sample is blown out of the column and 10 μL of 50% (v/v) acetonitrile/water is passed through the column, desorbing the DNA, and the sample is deposited into a vial for analysis.

Example 7

Desalting Proteins with an Extraction Column

Columns from Example 1 are bonded with a 21 μm pore size SPECTRA/MESH® polyester mesh material (Spectrum Labs, Ranch Dominguez, Calif., PN 148244) by the same procedure as described in Example 2. A 10 μL bed volume column is filled with PELLICULAR C18 (Alltech, Deerfield, Ill., PN 28551), particle size 30-50 μm. One end of the extraction column is connected to a pipettor pump (Gilson, Middleton, Wis., P-1000 PipetteMan) and the other end is movable and is connected to an apparatus where the materials may be taken up or deposited at different locations.

The sample is a 100 μL solution containing 0.1 μg of Protein kinase A in a phosphate buffer saline (0.9% w/v NaCl, 10 mM sodium phosphate, pH 7.2) (PBS) buffer. Ten μL of 10% aqueous solution of trifluoroacetic acid (TFA) is added so that the final volume of the solution is 110 μL and the concentration of the TFA in the sample is 0.1%. The sample is introduced into the column and the protein/TFA complex is adsorbed to the reverse phase of the bed.

The sample is blown out of the column and 10 μL of 50% (v/v) acetonitrile/water is passed through the column, desorbing the protein from the bed of extraction media, and the sample is deposited into a vial for analysis.

Alternatively, the bed may be washed with 10 μL of aqueous 0.1% TFA. This solution is ejected from the column and the protein is desorbed and deposited into the vile.

If necessary, alternatively 1% heptafluorobutyric acid (HFBA) is used instead of TFA to reduce ion suppression effect when the sample is analyzed by electrospray ion trap mass spectrometry.

Example 8

Straight Connection Configuration

This example describes an embodiment wherein the column body is constructed by engaging upper tubular members and membrane screens in a straight configuration.

Figure 11:
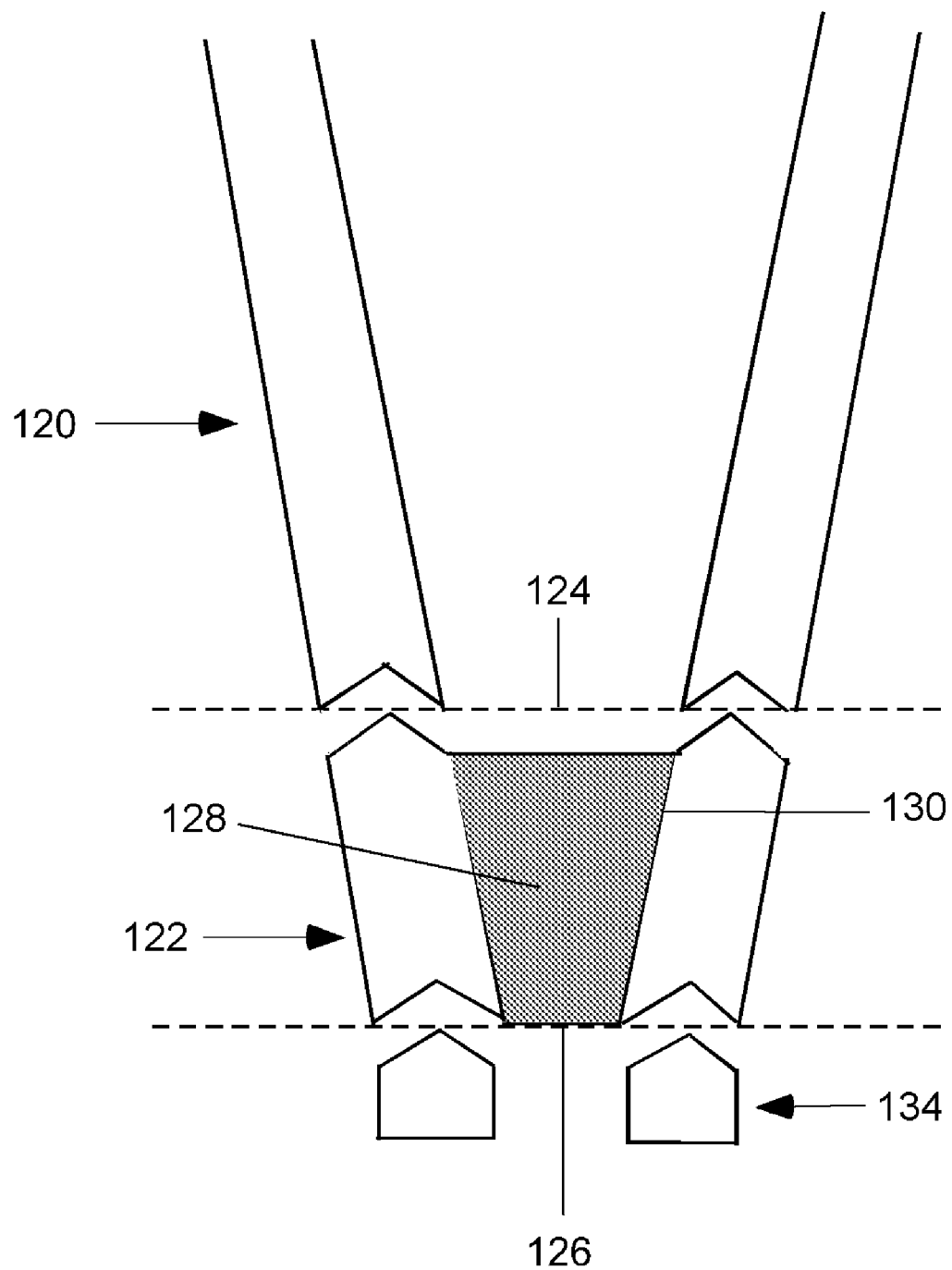
FIG. 11 depicts an embodiment of the invention with a straight connection configuration as described in Example 8.

Referring to FIG. 11, the column consists of an upper tubular member 120, a lower tubular member 122, a top membrane screen 124, a bottom membrane screen 126, and a lower tubular circle 134 to hold the bottom membrane screen in place. The top membrane screen is held in place by the upper and lower tubular members. The top membrane screen, bottom membrane screen and the channel surface 130 of the lower tubular member define an extraction media chamber 128, which contains a bed of extraction media (i.e., packing material). The tubular members as depicted in FIG. 11 are frustoconical in shape, but in related embodiments could take other shapes, e.g., cylindrical.

To construct a column, various components are made by forming injected molded members from polypropylene or machined members from PEEK polymer to give specified column lengths and diameters and ends that can fit together, i.e., engage with one another. The configuration of the male and female portions of the column body is shaped differently depending on the method used to assemble the parts and the method used to keep the parts together.

The components are glued or welded. Alternatively, they are snapped together. In the case of snapping the pieces together, the female portion contains a lip and the male portion contains a ridge that will hold and seal the pieces once they are assembled. The membrane screen is either cut automatically during the assembly process or is trimmed after assembly.

Example 9

End Cap and Retainer Ring Configuration

Figure 12:
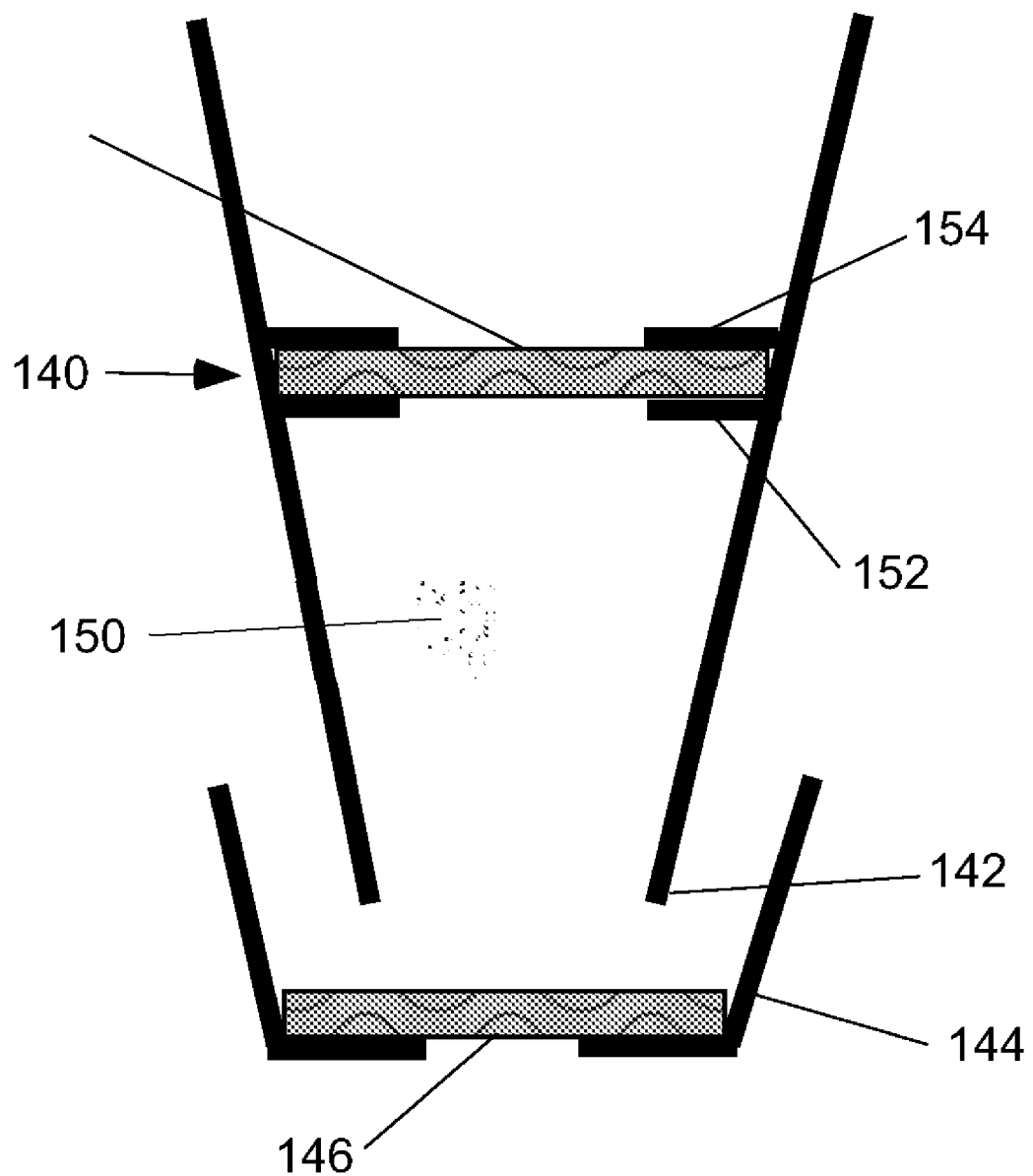
FIG. 12 depicts an embodiment of the invention with an end cap and retainer ring configuration as described in Example 9.

This example describes an embodiment where an end cap and retainer ring configuration is used to retain the membrane screens containing a 20 μl bed of column packing material. The embodiment is depicted in FIG. 12.

Referring to the figure, pipette tip 140 (VWR, Brisbane, Calif., PN 53508-987) was cut with a razor blade to have a flat and straight bottom end 142 with the smooth sides such that a press fit can be performed later. An end cap 144 was machined from PEEK polymer tubing to contain the bottom membrane screen 146.

Two different diameter screens were cut from polyester mesh (Spectrum Labs, Ranch Dominguez, Calif., PN 145836) by a circular cutting tool (Pace Punches, Inc., Irving, Calif.), one for the top membrane screen 140 and the other for the bottom membrane screen 146. The bottom membrane screen was placed into the end cap and pressed onto the end of the cut pipette tip.

A 20 μL volume bed of beads was formed by pipetting a 40 μL of 50% slurry of protein G agarose resin into the column body.

Two retainer rings were used to hold the membrane screen in place on top of the bed of beads. The retainer rings were prepared by taking ⅛ inch diameter polypropylene tubing and cutting thin circles from the tubing with a razor blade. A first retainer ring 152 was placed into the column and pushed down to the top of the bed with a metal rod of similar diameter. The membrane screen 148 was placed on top of the first retainer ring and then a second retainer ring 154 was pushed down to "sandwich" the membrane screen while at the same time pushing the whole screen configuration to the top of the bed and ensuring that all dead volume was removed. The two membranes define the top and bottom of the extraction media chamber 150, wherein the bed of beads is positioned. The membrane is flexible and naturally forms itself to the top of the bed.

The column was connected to a 1000 μL pipettor (Gilson, Middleton, Wis., P-1000 PipetteMan) and water was pumped through the bed and dispensed from the bed. The column had low resistance to flow for water solvent.

Example 10

Production of a Micro-bed Extraction Column

To manufacture a 0.1 μL bed, a polyester membrane is welded onto one end of a polypropylene tube of 300 mm inside diameter and 4 mm long. The bed is filled with a gel resin material to a height of 0.25 mm. A small circle or wad of membrane frit material is pushed into the end of the column. Then a 5 cm long fused silica capillary (320 μm od, 200 μm id) is inserted into the top of the polypropylene tube and pushed down to the top of the column bed. A fitting is used to attach a micro-syringe pump to the column, which allows for solution to be drawn in and out of the bed, for use in a micro-scale extraction of the type described herein.

Columns with various small bed volumes can be constructed using different pipette tips as starting materials. For example, a 0.5 μL bed column (0.4 mm average diameter and 0.4 mm length can be constructed using 10 μL pipette tips (Finnitip 10 from Thermolab Systems, Cat. No. 9400300). The membrane screen can be attached gluing, welding and mechanical attachment. The bed volume can be controlled more easily by gluing the membrane screen. Other columns with the sizes of 1.2, 2.2, 3.2, and 5.0 μL beds were made in a similar way from P-235 pipette tips available from Perkin Elmer (Cat. No. 69000067).

Example 11

Evaluation of a 10 μL, Bed Volume Pipet Tip Column Containing a Protein A Resin

In this example, the performance of 10 μL bed volume pipet tip columns (manufactured from 1 mL pipet tips (VWR)) containing a Protein A resin was evaluated. The resins under consideration consist of purified recombinant protein A covalently coupled through multi-point attachment via reductive amidation to 6% highly cross-linked agarose beads (RepliGen Corporation, IPA-400HC; PN: 10-2500-02)

or to 4% cross-linked sepharose beads (Amersham-Pharmacia). The samples tested consisted of 15 µg mFITC-MAb (Fitzgerald, Inc. Cat # 10-F50, mouse IgG$_{2a}$) in 0.5 ml of PBS or PBS containing 5 mg BSA (10 mg/ml or 1% m/v BSA).

An ME-100 multiplexing extraction system (Phynexus, Inc.) was used, the major elements of which are illustrated schematically in FIG. 13 and in the text accompanying that figure. The system was programmed to blow out the bulk of the storage solution from the tips prior to taking up the samples. The 0.5 mL samples were provided in 1.5 ml Eppendorf tubes and positioned in the sample rack, which was raised so that the tip of the columns made contact with the sample. During the load cycle, 2 or 5 in/out cycles were employed (depending upon the test), the volume drawn or ejected programmed at 0.6 ml @ 0.25 ml/min.

After loading, the extraction beds were washed with 2 in/out cycles, volume programmed at 0.6 ml @ 0.5 ml/min (certain experiments involved 4 separate washes, each with 0.5 ml PBS), or 1 wash with 1 ml PBS, volume programmed at 1.0 ml @ 0.5 ml/min followed by final wash with 0.5 ml H$_2$O.

The elution cycle involved 4 in/out cycles, volume programmed at 0.1-0.15 ml @ 1 ml/min (15 µl elution buffer, 111 mM NaH$_2$PO$_4$ in 14.8 mM H$_3$PO$_4$, pH 3.0).

To quantitate the IgG recovered in the procedure and to analyze its purity, 15 µl elution volume was divided into two parts: 13 µl was reacted with freshly prepared 13 µl of 10 mg/ml TCEP (final volume=26 µl and [TCEP]=17.5 mM) at room temperature for ~16 hours. 20 µl out of above 26 µl reduced IgG$_{2a}$ was injected into a non-porous polystyrene divinylbenzene reverse phase (C-18) column using an HP 1050 HPLC system. A gradient of 25% to 75% between solvent A which is 0.1% TFA in water and solvent B which is 0.1% TFA in ACN was used for 5 minutes. Detection: UV at 214 and 280 nm. There are two major IgG$_{2a}$ peaks having similar intensities as shown in the data below, which eluted around 3.17 and 3.3 min. Area under these two peaks was integrated from (3.13-3.5) min in each case and corresponding mAU was recorded at 214 nm. Only first elution (15 µl) percent recovery was calculated. TCEP-treated IgG$_{2a}$ standards (injected amount 1.08, 2.16, 4.32, 6.48 and 8.64 µg of FITC-MAb, obtained from Fitzgerald, Inc) under identical reaction condition was loaded into the column and used as a standard curve for recovery calculation.

Summary data shown below from these experiments indicate that IgG purification using the Protein A extraction columns was highly selective. A 333-fold excess of BSA can quantitatively be removed in a very fast process.

| Recoveries from selectivity assay (determined by HPLC method) | | |
|---|---|---|
| Amersham Recovery | Experimental Procedure | Repligen Recovery |
| 49% | 15 µg IgG$_{2a}$/0.5 ml PBS (2 cycles loading) | 43% |
| 64% | 15 µg IgG$_{2a}$/0.5 ml PBS + 5 mg BSA (2 cycles loading) | 56% |
| 66% | 15 µg IgG$_{2a}$/0.5 ml PBS + 5 mg BSA (5 cycles loading) | 62% |

Figure 14:
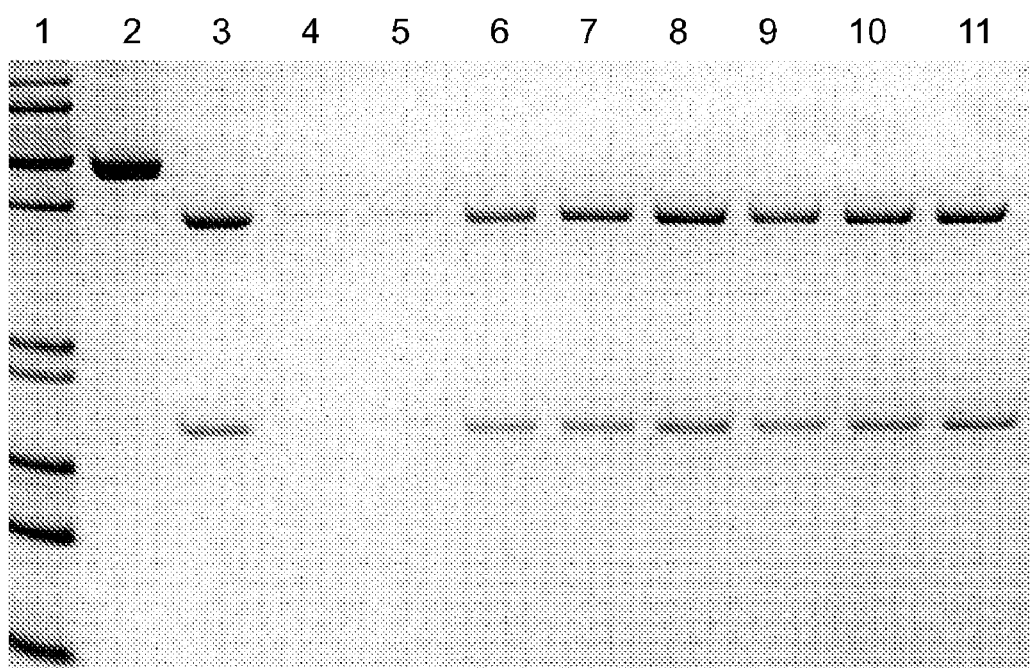
FIG. 14 is an SDS-PAGE gel referred to in Example 11.

2 ul of the reduced IgG from each experiment was analyzed by SDS-PAGE, using a Nu-PAGE 4-12% Bis-Tris gel with MES running buffer (FIG. 14). Lane 1: marker; Lane 2: 2 µg BSA; Lane 3: 2 µg IgG$_{2a}$; Lanes 4 and 5: RepliGen and Amersham Protein A resin only, respectively; Lanes 6, 7 and 8: 2 µl each of RepliGen Protein A purified IgG$_{2a}$ from PBS, PBS containing 5 mg BSA (2 and 5 cycles loading), respectively; Lanes 9, 10 and 11: 2 µl each of Amersham Protein A purified IgG$_{2a}$ from PBS, PBS containing 5 mg BSA (2 and 5 cycles loading), respectively.

Example 12

Comparison of Frit Backpressures

Figures 19A, 19B:
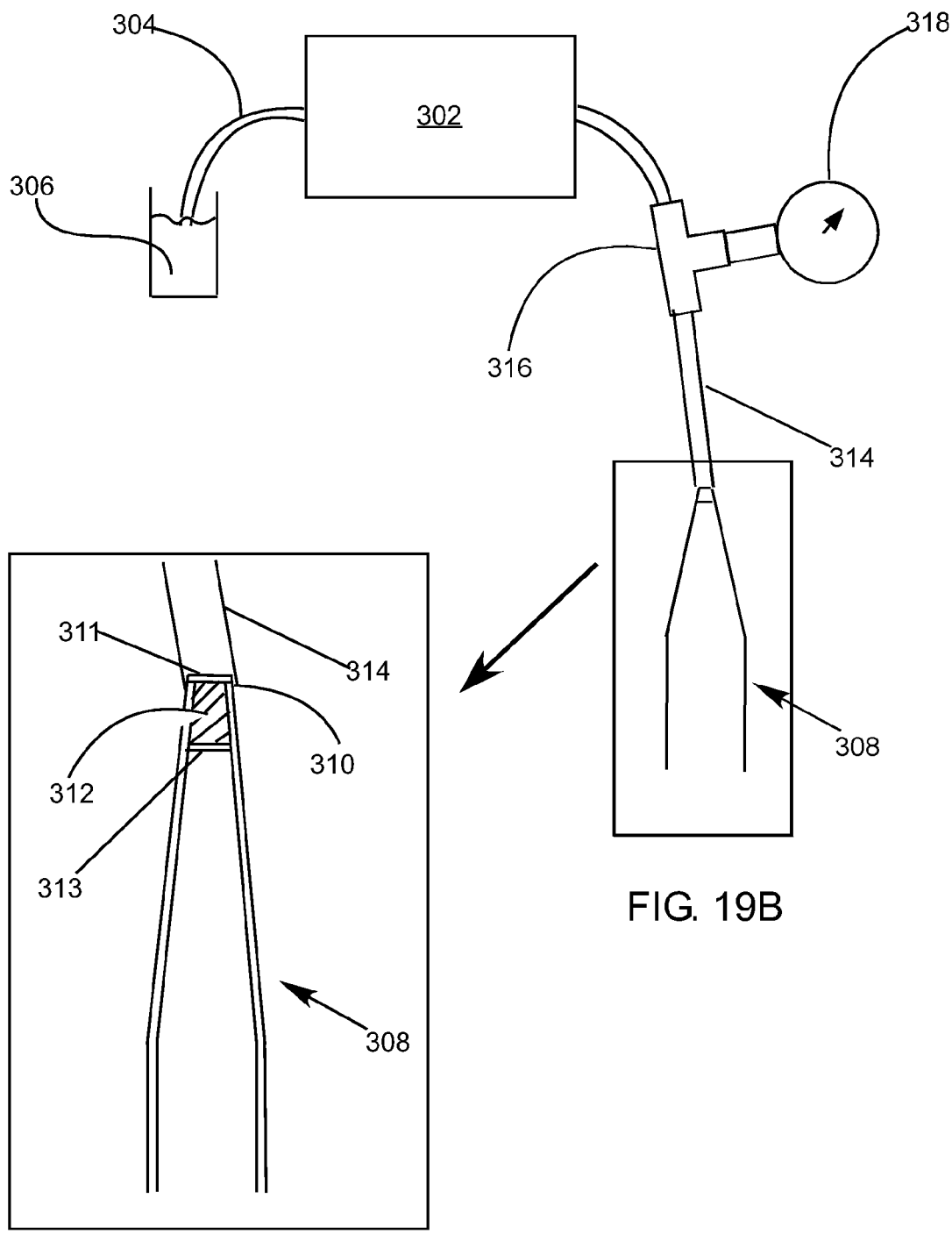
FIGS. 19A and B depict a pipette tip column attached to an apparatus for determining column back pressure.

The backpressure was determined for a number of screen frits and porous polymer frits using the following method. Referring to FIG. 19A, a tip column 308 comprising membrane frits 311 and 313 and a packed bed of resin 312 was attached to the output tubing 314 of the system described in the above example.

Initially, deionized water is pumped through the bed of extraction media 312 at a constant flow rate as described in the previous example, and the baseline backpressure is read off the pressure gauge once the flow and pressure have stabilized, i.e., reached equilibrium. The tip column 308 functions to produce a baseline backpressure when deionized water is pumped through the system. To measure the back pressure of a particular membrane frit, a membrane frit 320 is welded to the narrow end 322 of a pipette tip 324, and the narrow end of the tip 322 is fitted into the wide open end 326 of tip column 308 to form a friction seal (See FIG. 20A). The flow and pressure are allowed to stabilize, and the increase in backpressure relative to the baseline backpressure resulting from addition of the membrane is read off the pressure gauge.

In some experiments, the backpressure was determined for two or more membrane screens attached in series. This was accomplished by friction fitting two or more membrane-tipped pipette tips in series (324, 326 and 328) and attaching to the tip column 308 (see FIG. 21). The increase in backpressure resulting from the plurality of membranes is then read off the gauge once equilibrium has been reached.

Figures 20A, 20B:
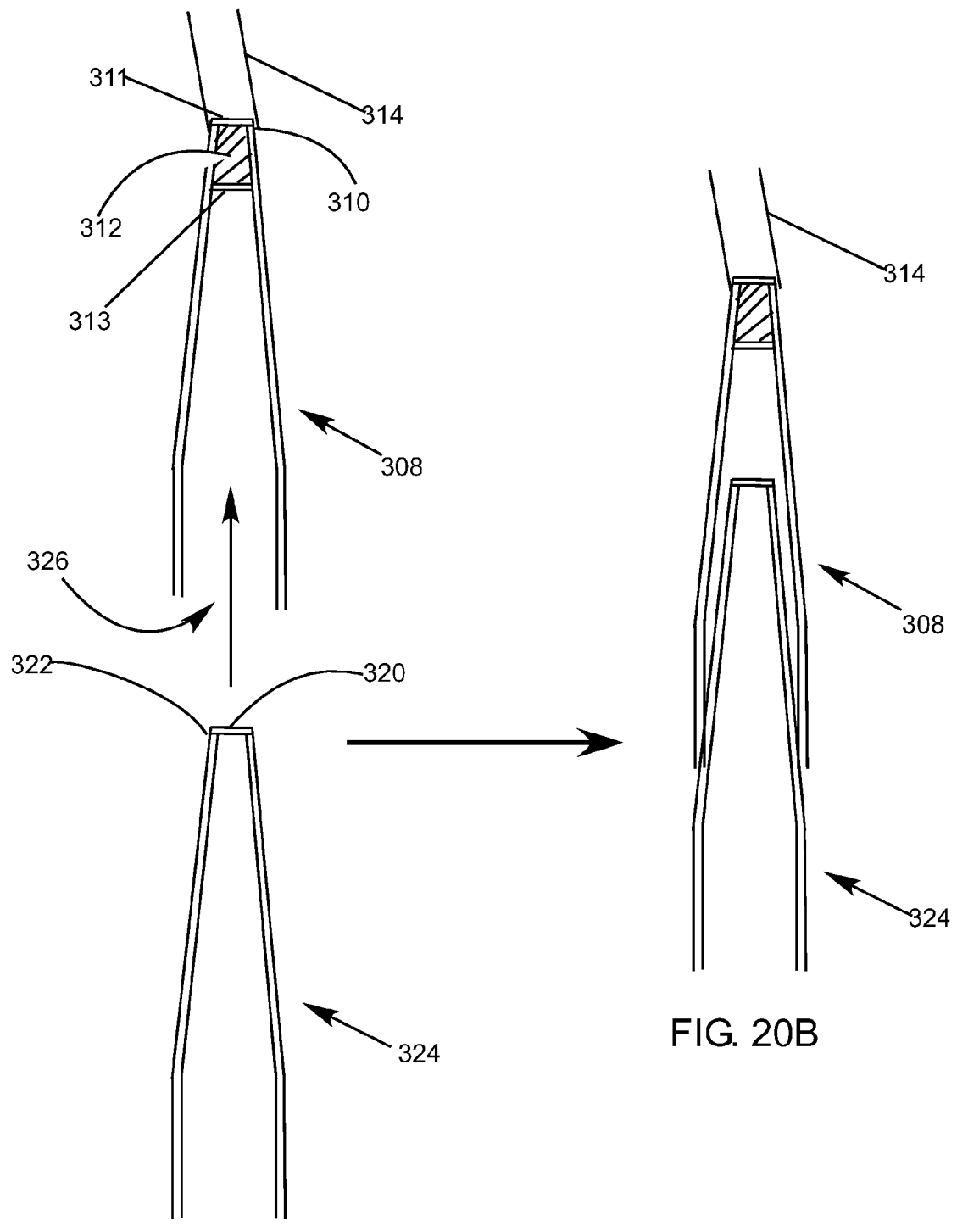
FIGS. 20 and 21 depict a method for determining the back pressure of a membrane frit as described in Example 12.
Figure 21:
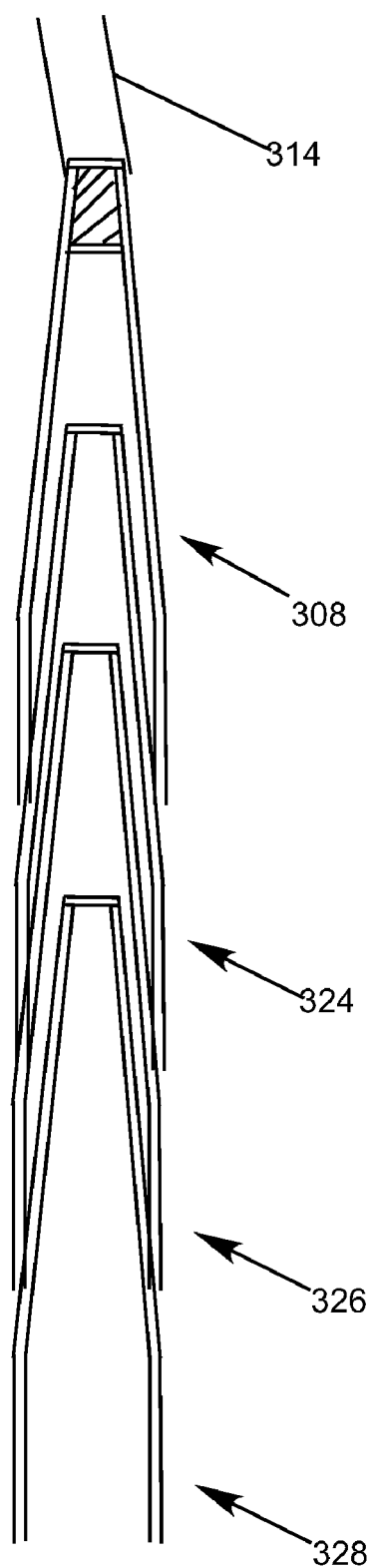

In a control experiment, it was determined that attachment of a pipette tip lacking a membrane frit (or several such pipette tips in series) in place of pipette tip 324 did not result in any detectable increase in backpressure (FIGS. 20B and 21). Hence any backpressure detected in the experiments is due solely to the frit or frits.

In one set of experiments, the backpressure for a 1.5 mm diameter 37 micron pore size polyester membrane frit (Spectrum Lab, Cat. No. 146529) was determined at a flow rate of 4 mL/min. The backpressures were determined for different single screens, and it was found that the addition of these membranes resulted in an increase in backpressure of 0.25, 0.3 and 0.3 kPa (1 psi=6.8948 kPa). Two screens were attached in series, and found to result in total increase in an increase in backpressure of 0.4 kPa. Three screens were attached in series, and found to result in an increase in backpressure of 1.1 kPa. Thus, it was concluded that at a flow rate of 4 mL/min, the backpressure of one of these membranes frits is about 0.3 kPa.

In a separate experiment, it was shown that the relationship between backpressure and flow rate is approximately linear. Hence, it can be extrapolated that at a flow rate of 1 mL/min (a typical flow rate when the frits are used in the context of a pipette tip extraction column) the backpressure of these membrane frits is about 0.3/4, or 0.075 kPa.

In another set of experiments, the relation between screen pore size, screen diameter and backpressure was assessed. Polyester membrane frits having pore sizes of 15 micron (Spectrum Lab, Cat. No. 145832), 21 micron (Spectrum Lab, Cat. No. 145833) and 37 micron (Spectrum Lab, Cat. No. 146529) were tested. Two different diameter screens were prepared. The small screen diameter was approximately 0.85 mm and the large screen diameter was 1.4 mm. Because the screens were welded to the tip, the effective diameter varied depending on how much the hot polypropylene flowed from the edge into the screen. This affected the backpressure on the smaller screen diameter much more than the large screen diameter. Three tips each were prepared for each pore size and for each diameter. The results were as follow:
1. Small screen, 15 um, 1 mL/min
Backpressure: 3.3, 2.7, 1.5 kPa
2. Small screen, 21 um, 4 mL/min
Backpressure: 2.5, 6.3, 3.6 kpa (Therefore effective backpressure at 1 mL/min is extrapolated to be 0.63, 1.6, 0.90 kpascals)
3. Small screen, 37 um, 4 mL/min, stack of 3 in series
Backpressure: 2.2 kPa (Therefore effective backpressure of one frit at 1 mL/min is extrapolated to be 0.18 kpacals)
4. Large screen, 15 um, 1 mL/min, stack of 3
Backpressure: 6.5 kPa (Therefore effective backpressure at 1 mL/min is extrapolated to be 2.2 kpascals)
5. Large screen, 21 um, 4 mL/min, stack of 3 in series
Backpressure: appr. 0.1 kPa (Therefore effective backpressure at 1 mL/min is extrapolated to be 0.0083 kpascals)
6. Large screen 37 um, 4 mL/min, stack of 3 in series
Backpressure: appr. 0.05 kP (Therefore effective backpressure at mL/min 0.0042 is extrapolated to be kpascals)

Figure 22:
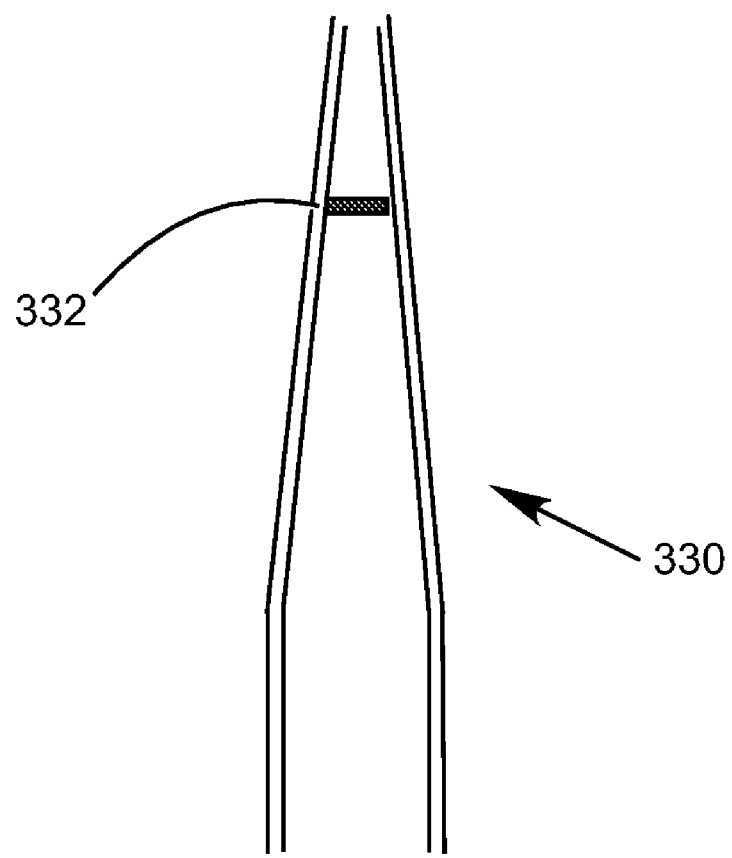
FIG. 22 depicts a porous frit, the back pressure of which is to be determined as described in Example 12.

The back pressure was also determined for frits made from porous polymer material, similar to the types of frits used in more column chromatography. The porous polymer frit were friction fit into pipette tips as shown in FIG. 22 (330 is the pipette tip and 332 is the frit), and the backpressure was determined using the same device and methodology as described above for use with membrane frits. (Note the diameters of the frits reported are cut size. When the frit is pushed into the tip body, the diameter will decrease. Larger starting diameter of frits had to be pushed more firmly into the pipette body to prevent it from dislodging.)

All porous polymer frits tested were 1/16 inch thick, and varied in diameter and pore size. The materials tested were a 35 micron pore hydrophilic polymer (3.4 and 4.4 mm diameter) obtained from Scientific Commodities (Lake Havasu City, Az, Cat No. BB2062-35L); a 15-45 micron pore, UHMW Polypropylene polymer obtained from Porex (Cat. No. X-4900) and a 20-25 micron polypropylene polymer obtained from GenPore (Reading, Pa.). The measured backpressures are presented in the following table. The backpressures are substantially higher than those seen with the membrane frits.

| Pore size (micron) | Frit diameter (mm) | Flow rate (mL/min) | Backpressure (kPa) |
| --- | --- | --- | --- |
| 35 | 3.4 | 4 | 8.5 |
| 35 | 3.4 | 3 | 6.0 |
| 35 | 3.4 | 2 | 3.6 |
| 35 | 3.4 | 1 | 1.8 |
| 35 | 4.4 | 4 | 4.6 |
| 35 | 4.4 | 3 | 3.5 |
| 35 | 4.4 | 2 | 1.5 |
| 35 | 4.4 | 1 | low |
| 15-45 | 3.4 | 4 | 11.0 |
| 15-45 | 3.4 | 3 | 7.7 |
| 15-45 | 3.4 | 2 | 4.8 |
| 15-45 | 3.4 | 1 | 2.0 |
| 15-45 | 4.4 | 4 | 9.5 |
| 15-45 | 4.4 | 3 | 6.5 |
| 15-45 | 4.4 | 2 | 4.0 |
| 15-45 | 4.4 | 1 | 1.8 |
| 20-25 | 1.4 | 4 | high |
| 20-25 | 1.4 | 3 | 9.0 |
| 20-25 | 1.4 | 2 | 6.0 |
| 20-25 | 1.4 | 1 | 2.5 |

Example 13

Comparison of Column Backpressures

Column backpressure was determined for a number of pipette tip-based columns using the following method. Referring to FIG. 19B, an HP1050 pump 302 (Hewlett-Packard) was configured such that the input tubing 304 is submerged in deionized water 306. To measure the back pressure of a particular tip column 308, the narrow end 310 of the tip column (containing packed bed 312 between membrane frits 311 and 313) is fitted into the open end of the output tubing 314 to form a friction seal. The output tubing includes a t-fitting 316 attached to a Marshall Town pressure gauge 318 with a range of 0-5 psi (0-34 kPa). The deionized water is then pumped through the packed bed 312 at a constant flow rate, and the back pressure is read off the pressure gauge once the flow and pressure have stabilized, i.e., reached equilibrium.

When the pump is first turned on, depending upon the backpressure of the column, it can take a while for enough pressure to build up before water starts flowing through the column at a constant flow rate. Typically, in order to reach equilibrium more quickly, the pump was initially run at a faster flow rate (e.g., 2 mL/min) and then backed off to the desired rate (e.g., 1 mL/min) once the flow through the column had reached a rate around the desired rate.

For some columns, the backpressure was determined at only 1 mL/min. For other columns, backpressure was determined for a series of ascending flow rates (e.g., 1, 2, 3 and 4 mL/min). For these experiments the relationship between flow rate and back pressure was found to be approximately linear. For some of the smaller columns, the backpressure at 1 mL/min was so low that it could not be accurately measured with the pressure gauge used. In those cases, the back pressure was determined at a flow rate of 5 mL/min, and the backpressure at 1 mL/min calculated based on an assumed linear relationship between flow rate and backpressure (as demonstrated for other columns). The backpressures are presented in the following table. The C18 Zip Tip was obtained from Millipore (Billerica, Mass.). The other tips are packed resin bed pipette tip columns manufactured as described herein. Column bodies were made by modifying pipette tips obtained from several different vendors, including 200+ tips supplied by Packard/Perkin-Elmer (200+ PE), 200+ tips provided by Rainin (200+ R), and 200+ tips designed to be used with a Zymark instrument (200+ Z). Each of the resin columns used 37 micron polyester membrane from Spectrum Labs for the frit material, which was welded onto the tip body. Ni-NTA agarose resin (Ni-NTA) was obtained from Qiagen (Germany). Protein A Sepharose resin was (ProA) was obtained from Repligen. Protein G agarose resin (ProG) was obtained from Exalpha. Glutathione Sepharose resin (Glu) was obtained from Amersham. Most of the tip columns had bed volumes of about 5 uL, except for three 200+ Z-ProA tips that were prepared with bed volumes of about 1.25 uL, 0.62 uL and 0.25 uL. Specific bed dimensions for the beds in each type of column are as follows: 200+ PE, bed length 2.4 mm, bed diameter 1.6-1.82 mm, calculated bed volume of 5.5 uL; 200+ R bed length 2.3 mm, bed diameter 1.5-1.82 mm, calculated bed volume of 5.0 uL; 200+ Z bed length 2.5 mm, bed diameter 1.43-1.82 mm, calculated bed volume of 5.2 uL. The smaller bed volume tips had bed diameters of 1.75-1.82 mm, bed volumes of about 1.25 uL, 0.62 uL and 0.25 uL, corresponding to bed heights of about 0.5 mm, 0.4 mm and 0.3 mm, respectively.

Note that the Zip Tip columns have substantially higher backpressures than the tip columns comprising a packed bed of resin and membrane frits.

The effect of varying the tightness of bed pack was assessed by comparing the backpressure of 200+ Z-ProA, 5.2 µL bed tips that were packed tighter than the other beds. Note that tighter packing of the bed leads to substantially higher backpressures.

| C18 Zip Tip | | | | |
|---|---|---|---|---|
| mL/min | 1.0 | | | |
| kpascals | 28.0 | | | |
| 200+ PE-Ni-NTA, 5.5 µL bed | | | | |
| mL/min | 1.0 | 2.0 | 3.0 | 4.0 |
| kpascals | 2.4 | 4.9 | 8.0 | 11.3 |
| 200+ R-ProA, 5.0 µL bed | | | | |
| mL/min | 1.0 | | | |
| kpascals | 2.5 | | | |
| 200+ R-Ni-NTA, 5.0 µL bed | | | | |
| mL/min | 1.0 | | | |
| kpascals | 2.5 | | | |
| 200+ PE-ProA, 5.5 µL bed | | | | |
| mL/min | 1.0 | | | |
| kpascals | 1.7 | | | |
| 200+ PE-ProG, 5.5 µL bed | | | | |
| mL/min | 1.0 | | | |
| kpascals | 1.8 | | | |
| 200+ R-Glu, 5.0 µL bed | | | | |
| mL/min | 1.0 | | | |
| kpascals | 3.2 | | | |
| 200+ R-ProG, 5.0 µL bed | | | | |
| mL/min | 1.0 | 2.0 | 3.0 | 4.0 |
| kpascals | 2.5 | 3.6 | 5.8 | 8.2 |

| | A, tighter bed | B, tighter bed |
|---|---|---|
| 200+ Z-ProA, 5.2 µL bed | | |
| mL/min | 1.0 | 1.0 |
| kpascals | 18.5 | 50 |
| 200+ Z-ProA, 1.25 µL bed | | |
| mL/min | 1.0 | 2.0 3.0 4.0 |
| kpascals | 1.1 | 2.3 3.5 4.6 |
| 200+ Z-ProA, 0.62 µL bed | | |
| mL/min | 5.0 | 1.0 |
| kpascals | 2.0 | 0.4* |
| 200+ Z-ProA, 0.25 µL bed | | |
| mL/min | 5.0 | 1.0 |
| kpascals | 0.4 | 0.08* |

*Values extrapolated from 5.0 mL/min pressure.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. A pipette tip extraction column comprising:
   i) a column body having an open upper end, an open lower end, and an open channel between the upper and lower ends of the column body, wherein the column body is comprised of a modified pipette tip;
   ii) a bottom frit extending across the open channel, said bottom frit having a pore volume of less than one microliter; and
   iii) a bed of resin media positioned inside the open channel and in contact with the bottom frit.

2. The pipette tip extraction column of claim 1, wherein the bottom frit comprises a hydrophilic membrane screen.

3. The pipette tip extraction column of claim 1, wherein the bottom frit is located at the open lower end of the column body.

4. The pipette tip extraction column of claim 3, wherein the open lower end of the extraction column is in contact with the sample solution, the wash solution or the desorption solution.

5. The pipette tip extraction column of claim 1, wherein the upper end of the column body is operatively attached to a pump for aspirating and discharging fluid through the lower end of the column body.

6. The pipette tip extraction column of claim 5, wherein the pump is a pipettor or a syringe.

7. The pipette tip extraction column of claim 1, wherein the resin media comprises an affinity binding group having an affinity for a biological molecule of interest.

8. The pipette tip extraction column of claim 7, wherein the affinity binding group is selected from the group consisting of Protein A, Protein G, Protein L and an immobilized metal.

9. The pipette tip extraction column of claim 7, wherein the biological molecule is an active protein.

10. The pipette tip extraction column of claim 1, wherein the bed of resin media has a volume of between 0.1 ul and 1000 ul.

11. The pipette tip extraction column of claim 10, wherein the bed of resin media is comprised of silica.

12. The pipette tip extraction column of claim 1, further comprising a top frit extending across the open channel between the bed of resin media and the open upper end of the column body.

13. The pipette tip extraction column of claim 12 wherein the top frit has a pore volume of less than one microliter.

14. The pipette tip extraction column of claim 13 wherein the top frit or the bottom frit has a pore volume of less than 0.5 microliters.

15. The pipette tip extraction column of claim 12, wherein the top frit or the bottom frit comprises a membrane screen.

16. The pipette tip extraction column of claim 15, wherein the top frit or the bottom frit is comprised of a material selected from the group consisting of nylon, polyester, polyamide, polycarbonate, cellulose, polyethylene, nitrocellulose, cellulose acetate, polyvinylidene difluoride, polytetrafluoroethylene (PTFE), polypropylene, polysulfone, metal and glass.

17. The pipette tip extraction column of claim 15, wherein the top frit or the bottom frit comprises a nylon or polyester woven membrane.

18. A multiplexed extraction system comprised of:
   a plurality of pipette tip extraction columns of claim 1, wherein each extraction column is controlled by a pump.

19. The multiplexed extraction system of claim 18, wherein the multiplexed extraction system is further comprised of:
   a controller for controlling the pumps; and
   a computer operating said controller, wherein the computer can be programmed to control the movement of the pumps through the controller.

20. The multiplexed extraction system of claim 19, wherein the pipette tip extraction columns are further comprised of a top frit extending across the open channel between the bed of resin media and the open upper end of the column body, wherein the bottom frit is located at the open lower end of the column body, wherein the resin media is further comprised of an affinity binding group selected from the group consisting of Protein A, Protein G, Protein L and an immobilized metal.

21. The multiplexed extraction system of claim 19, wherein the bed of resin media is comprised of silica.

22. A pipette tip extraction column comprising:
   i) a column body having an open upper end, an open lower end, and an open channel between the upper and lower ends of the column body, wherein the column body is comprised of a modified pipette tip;
   ii) a bottom frit extending across the open channel, said bottom frit having a pore volume of less than one microliter, wherein the bottom frit is located at the open lower end of the column body;
   iii) a top frit extending across the open channel between the bottom frit and the open upper end of the column body; and
   iv) a bed of resin media positioned between the bottom frit and the top frit, wherein the resin media is further comprised of an affinity binding group selected from the group consisting of Protein A, Protein G, Protein L and an immobilized metal.

* * * * *

UNITED STATES PATENT AND TRADEMARK OFFICE
CERTIFICATE OF CORRECTION

PATENT NO. : 8,148,168 B2
APPLICATION NO. : 12/837141
DATED : April 3, 2012
INVENTOR(S) : Douglas T. Gjerde et al.

Page 1 of 1

It is certified that error appears in the above-identified patent and that said Letters Patent is hereby corrected as shown below:

In the specification

Column 3, line 48 should read "herein is"

Column 18, line 59 should read "used to aspirate"

Column 20, line 9 should read "cell lysates"

Column 27, line 46 should read "further comprises"

Column 34, line 38 should read "glycoproteins from cells"

Signed and Sealed this
Twenty-eighth Day of June, 2016

Michelle K. Lee
*Director of the United States Patent and Trademark Office*